US012666156B2

(12) United States Patent (10) Patent No.: US 12,666,156 B2
Moore et al. (45) Date of Patent: Jun. 23, 2026

(54) SYSTEMS AND METHODS FOR ILLUMINATION AND IMAGING OF A TARGET

(71) Applicant: Stryker Corporation, Kalamazoo, MI (US)

(72) Inventors: Frederick Allen Moore, Vancouver (CA); Robert Anthony Stead, North Vancouver, CA (US)

(73) Assignee: Stryker Corporation, Portage, MI (US)

( * ) Notice: Subject to any disclaimer, the term of this patent is extended or adjusted under 35 U.S.C. 154(b) by 53 days.

(21) Appl. No.: 18/601,995

(22) Filed: Mar. 11, 2024

(65) Prior Publication Data

US 2024/0298091 A1 Sep. 5, 2024

Related U.S. Application Data

(60) Continuation of application No. 16/933,900, filed on Jul. 20, 2020, now Pat. No. 11,930,278, which is a (Continued)

(51) Int. Cl.
*H04N 23/55* (2023.01)
*A61B 46/10* (2016.01)
(Continued)

(52) U.S. Cl.
CPC ............. *H04N 23/74* (2023.01); *A61B 46/10* (2016.02); *A61B 90/30* (2016.02); *H04N 23/51* (2023.01);
(Continued)

(58) Field of Classification Search
CPC ................ H04N 23/55; A61B 1/00163; A61B 1/00186; A61B 1/042–044;
(Continued)

(56) References Cited

U.S. PATENT DOCUMENTS 1,290,744 A 1/1919 Hollander
2,453,336 A 11/1948 Orser
(Continued)

FOREIGN PATENT DOCUMENTS

CN 2076516 U 5/1991
CN 101242789 A 8/2008
(Continued)

OTHER PUBLICATIONS

US 6,692,429 B1, 02/2004, Imaizumi et al. (withdrawn)
(Continued)

*Primary Examiner* — Anthony J Daniels
(74) *Attorney, Agent, or Firm* — Morrison & Foerster LLP

(57) ABSTRACT

An imaging device for imaging target tissue of a subject is provided. The imaging device includes at least one imaging sensor and a wavelength-dependent aperture upstream of the at least one imaging sensor. The wavelength-dependent aperture includes a first aperture portion configured to permit transmission of visible light and fluorescence light, and a second aperture portion surrounding the first aperture portion and configured to permit transmission of the fluorescence light and block transmission of the visible light, wherein the second aperture portion is configured to block transmission of the visible light through absorption.

22 Claims, 30 Drawing Sheets
(1 of 30 Drawing Sheet(s) Filed in Color)

Related U.S. Application Data continuation of application No. 16/441,493, filed on Jun. 14, 2019, now Pat. No. 10,721,410, which is a division of application No. 15/348,664, filed on Nov. 10, 2016, now Pat. No. 10,356,334.

(60) Provisional application No. 62/255,024, filed on Nov. 13, 2015.

(51) Int. Cl.

| | |
|---|---|
| *A61B 90/30* | (2016.01) |
| *H04N 23/51* | (2023.01) |
| *H04N 23/56* | (2023.01) |
| *H04N 23/71* | (2023.01) |
| *H04N 23/74* | (2023.01) |
| *A61B 17/00* | (2006.01) |
| *A61B 90/00* | (2016.01) |

(52) U.S. Cl.
CPC ............. *H04N 23/56* (2023.01); *H04N 23/71* (2023.01); *A61B 2017/00477* (2013.01); *A61B 2090/306* (2016.02); *A61B 2090/309* (2016.02); *A61B 90/361* (2016.02); *A61B 2090/3941* (2016.02)

(58) Field of Classification Search
CPC ...... A61B 1/00096; G02B 5/005; G03B 9/02; G03B 9/04
USPC ....................................................... 348/335
See application file for complete search history.

(56) References Cited

U.S. PATENT DOCUMENTS

| | | | |
|---|---|---|---|
| 2,857,523 | A | 10/1958 | Corso |
| 3,215,029 | A | 11/1965 | Woodcock |
| 3,582,178 | A | 6/1971 | Boughton et al. |
| 3,671,098 | A | 6/1972 | Rotter |
| 3,749,494 | A | 7/1973 | Hodges |
| 3,762,801 | A | 10/1973 | Baker |
| 3,790,248 | A | 2/1974 | Kellow |
| 3,931,593 | A | 1/1976 | Marshall |
| 3,970,373 | A | 7/1976 | Pledger |
| 3,971,068 | A | 7/1976 | Gerhardt et al. |
| 4,037,866 | A | 7/1977 | Price |
| 4,066,330 | A | 1/1978 | Jones |
| 4,115,812 | A | 9/1978 | Akatsu |
| 4,149,190 | A | 4/1979 | Wessler et al. |
| 4,158,504 | A | 6/1979 | de Ponteves et al. |
| 4,200,801 | A | 4/1980 | Schuresko |
| 4,260,217 | A | 4/1981 | Traeger et al. |
| 4,318,395 | A | 3/1982 | Tawara |
| 4,355,325 | A | 10/1982 | Nakamura et al. |
| 4,378,571 | A | 3/1983 | Handy |
| 4,449,535 | A | 5/1984 | Renault |
| 4,471,766 | A | 9/1984 | Terayama |
| 4,532,918 | A | 8/1985 | Wheeler |
| 4,556,057 | A | 12/1985 | Hiruma et al. |
| 4,575,632 | A | 3/1986 | Lange |
| 4,597,630 | A | 7/1986 | Brandstetter et al. |
| 4,611,888 | A | 9/1986 | Prenovitz et al. |
| 4,638,365 | A | 1/1987 | Kato |
| 4,656,508 | A | 4/1987 | Yokota |
| 4,660,982 | A | 4/1987 | Okada |
| 4,688,905 | A | 8/1987 | Okamura |
| 4,717,952 | A | 1/1988 | Kohayakawa et al. |
| 4,742,388 | A | 5/1988 | Cooper et al. |
| 4,768,513 | A | 9/1988 | Suzuki |
| 4,786,813 | A | 11/1988 | Svanberg et al. |
| 4,799,104 | A | 1/1989 | Hosoya et al. |
| 4,806,005 | A | 2/1989 | Schneider et al. |
| 4,821,117 | A | 4/1989 | Sekiguchi |
| 4,837,625 | A | 6/1989 | Douziech et al. |
| 4,852,985 | A | 8/1989 | Fujihara et al. |

| | | | |
|---|---|---|---|
| 4,856,495 | A | 8/1989 | Tohjoh et al. |
| 4,885,634 | A | 12/1989 | Yabe |
| 4,895,145 | A | 1/1990 | Joffe et al. |
| 4,930,516 | A | 6/1990 | Alfano et al. |
| 4,930,883 | A | 6/1990 | Salzman |
| 4,951,135 | A | 8/1990 | Sasagawa et al. |
| 4,953,539 | A | 9/1990 | Nakamura et al. |
| 4,954,897 | A | 9/1990 | Ejima et al. |
| 4,974,936 | A | 12/1990 | Ams et al. |
| 5,001,556 | A | 3/1991 | Nakamura et al. |
| 5,007,408 | A | 4/1991 | Ieoka |
| 5,028,128 | A | 7/1991 | Onuki |
| 5,034,888 | A | 7/1991 | Uehara et al. |
| 5,041,852 | A | 8/1991 | Misawa et al. |
| 5,115,308 | A | 5/1992 | Onuki |
| 5,121,220 | A | 6/1992 | Nakamoto |
| 5,128,803 | A | 7/1992 | Sprafke |
| 5,132,837 | A | 7/1992 | Kitajima |
| 5,134,662 | A | 7/1992 | Bacus et al. |
| 5,159,398 | A | 10/1992 | Maekewa et al. |
| 5,165,079 | A | 11/1992 | Schulz-Hennig |
| 5,205,280 | A | 4/1993 | Dennison, Jr. et al. |
| 5,208,651 | A | 5/1993 | Buican |
| 5,212,593 | A | 5/1993 | Williamson et al. |
| 5,214,503 | A | 5/1993 | Chiu et al. |
| 5,225,883 | A | 7/1993 | Carter et al. |
| 5,255,087 | A | 10/1993 | Nakamura et al. |
| 5,278,642 | A | 1/1994 | Danna et al. |
| 5,282,082 | A | 1/1994 | Espie et al. |
| 5,295,017 | A | 3/1994 | Brown |
| RE34,622 | E | 5/1994 | Ledley |
| 5,365,057 | A | 11/1994 | Morley et al. |
| 5,371,355 | A | 12/1994 | Wodecki |
| 5,377,686 | A | 1/1995 | O'Rourke et al. |
| 5,379,756 | A | 1/1995 | Pileski et al. |
| 5,408,263 | A | 4/1995 | Kikuchi et al. |
| 5,410,363 | A | 4/1995 | Capen et al. |
| 5,419,323 | A | 5/1995 | Kittrell et al. |
| 5,420,628 | A | 5/1995 | Poulsen et al. |
| 5,421,337 | A | 6/1995 | Richards-Kortum et al. |
| 5,424,841 | A | 6/1995 | Van Gelder et al. |
| 5,426,530 | A | 6/1995 | Copenhaver et al. |
| 5,430,476 | A | 7/1995 | Häfele et al. |
| 5,467,223 | A | 11/1995 | Cleveland, Jr. et al. |
| 5,481,401 | A | 1/1996 | Kita et al. |
| 5,485,203 | A | 1/1996 | Nakamura et al. |
| 5,490,015 | A | 2/1996 | Umeyama et al. |
| 5,507,287 | A | 4/1996 | Palcic et al. |
| 5,515,449 | A | 5/1996 | Tsuruoka et al. |
| 5,535,052 | A | 7/1996 | Jörgens |
| 5,536,236 | A | 7/1996 | Yabe et al. |
| 5,557,451 | A | 9/1996 | Copenhaver et al. |
| 5,582,168 | A | 12/1996 | Samuels et al. |
| 5,585,846 | A | 12/1996 | Kim |
| 5,590,660 | A | 1/1997 | MacAulay et al. |
| 5,591,119 | A | 1/1997 | Adair |
| 5,596,654 | A | 1/1997 | Tanaka |
| 5,630,782 | A | 5/1997 | Adair |
| 5,646,680 | A | 7/1997 | Yajima |
| 5,647,368 | A | 7/1997 | Zeng et al. |
| 5,647,840 | A | 7/1997 | D'Amelio et al. |
| 5,667,472 | A | 9/1997 | Finn et al. |
| 5,677,724 | A | 10/1997 | Takizawa et al. |
| 5,682,567 | A | 10/1997 | Spruck et al. |
| 5,689,354 | A | 11/1997 | Orino |
| 5,695,049 | A | 12/1997 | Bauman |
| 5,697,373 | A | 12/1997 | Richards-Kortum et al. |
| 5,713,364 | A | 2/1998 | DeBaryshe et al. |
| 5,729,382 | A | 3/1998 | Morita et al. |
| 5,749,830 | A | 5/1998 | Kaneko et al. |
| 5,769,792 | A | 6/1998 | Palcic et al. |
| 5,772,355 | A | 6/1998 | Ross et al. |
| 5,772,580 | A | 6/1998 | Utsui et al. |
| 5,803,905 | A | 9/1998 | Allred et al. |
| 5,827,190 | A | 10/1998 | Palcic et al. |
| 5,833,617 | A | 11/1998 | Hayashi |
| 5,838,001 | A | 11/1998 | Minakuchi et al. |
| 5,840,017 | A | 11/1998 | Furuswaba et al. |
| 5,852,498 | A | 12/1998 | Youvan et al. |

(56)                    References Cited

U.S. PATENT DOCUMENTS

| | | | |
|---|---|---|---|
| 5,879,621 A | 3/1999 | Faries, Jr. et al. |
| 5,891,016 A | 4/1999 | Utsui et al. |
| 5,897,269 A | 4/1999 | Ross et al. |
| 5,971,918 A | 10/1999 | Zanger |
| 5,973,315 A | 10/1999 | Saldana et al. |
| 5,984,861 A | 11/1999 | Crowley |
| 5,986,271 A | 11/1999 | Lazarev et al. |
| 5,986,642 A | 11/1999 | Ueda et al. |
| 5,990,996 A | 11/1999 | Sharp |
| 5,999,240 A | 12/1999 | Sharp et al. |
| 6,002,137 A | 12/1999 | Hayashi |
| 6,004,263 A | 12/1999 | Nakaichi et al. |
| 6,008,889 A | 12/1999 | Zeng et al. |
| 6,021,344 A | 2/2000 | Lui et al. |
| 6,028,323 A | 2/2000 | Liu |
| 6,028,622 A | 2/2000 | Suzuki |
| 6,030,339 A | 2/2000 | Tatsuno et al. |
| 6,059,719 A | 5/2000 | Yamamoto et al. |
| 6,059,720 A | 5/2000 | Furusawa et al. |
| 6,061,591 A | 5/2000 | Freitag et al. |
| 6,069,689 A | 5/2000 | Zeng et al. |
| 6,070,096 A | 5/2000 | Hayashi |
| 6,095,982 A | 8/2000 | Richards-Kortum et al. |
| 6,099,466 A | 8/2000 | Sano et al. |
| 6,110,106 A | 8/2000 | MacKinnon et al. |
| 6,120,435 A | 9/2000 | Eino |
| 6,147,705 A | 11/2000 | Krauter et al. |
| 6,148,227 A | 11/2000 | Wagnières et al. |
| 6,161,035 A | 12/2000 | Furusawa |
| 6,181,414 B1 | 1/2001 | Raz et al. |
| 6,192,267 B1 | 2/2001 | Scherninski et al. |
| 6,212,425 B1 | 4/2001 | Irion et al. |
| 6,226,126 B1 | 5/2001 | Conemac |
| 6,258,576 B1 | 7/2001 | Richards-Kortum et al. |
| 6,280,378 B1 | 8/2001 | Kazuhiro et al. |
| 6,293,911 B1 | 9/2001 | Imaizumi et al. |
| 6,315,712 B1 | 11/2001 | Rovegno |
| 6,332,092 B1 | 12/2001 | Deckert et al. |
| 6,364,829 B1 | 4/2002 | Fulghum |
| 6,364,831 B1 | 4/2002 | Crowley |
| 6,377,842 B1 | 4/2002 | Pogue et al. |
| 6,419,628 B1 | 7/2002 | Rudischhauser et al. |
| 6,422,994 B1 | 7/2002 | Kaneko et al. |
| 6,462,770 B1 | 10/2002 | Cline et al. |
| 6,510,338 B1 | 1/2003 | Irion et al. |
| 6,526,213 B1 | 2/2003 | Ilenda et al. |
| 6,529,239 B1 | 3/2003 | Dyck et al. |
| 6,529,768 B1 | 3/2003 | Hakamata |
| 6,537,211 B1 | 3/2003 | Wang et al. |
| 6,544,102 B2 | 4/2003 | Schäfer et al. |
| 6,571,119 B2 | 5/2003 | Hayashi |
| 6,596,996 B1 | 7/2003 | Stone et al. |
| 6,603,552 B1 | 8/2003 | Cline et al. |
| 6,639,664 B2 | 10/2003 | Haan et al. |
| 6,652,452 B1 | 11/2003 | Seifert et al. |
| 6,750,971 B2 | 6/2004 | Overbeck et al. |
| 6,772,003 B2 | 8/2004 | Kaneko et al. |
| 6,773,392 B2 | 8/2004 | Kikuchi et al. |
| 6,786,865 B2 | 9/2004 | Dhindsa |
| 6,821,245 B2 | 11/2004 | Cline et al. |
| 6,826,424 B1 | 11/2004 | Zeng et al. |
| 6,898,458 B2 | 5/2005 | Zeng et al. |
| 6,899,675 B2 | 5/2005 | Cline et al. |
| 6,922,583 B1 | 7/2005 | Perelman et al. |
| 6,958,862 B1 | 10/2005 | Joseph |
| 6,960,165 B2 | 11/2005 | Ueno et al. |
| 7,043,291 B2 | 5/2006 | Sendai |
| 7,123,416 B1 | 10/2006 | Erdogan |
| 7,150,552 B2 | 12/2006 | Weidel |
| 7,179,222 B2 | 2/2007 | Imaizumi et al. |
| 7,235,045 B2 | 6/2007 | Wang et al. |
| 7,236,815 B2 | 6/2007 | Richards-Kortum et al. |
| 7,253,894 B2 | 8/2007 | Zeng et al. |
| 7,268,878 B2 | 9/2007 | Wolf et al. |
| 7,324,674 B2 | 1/2008 | Ozawa et al. |
| 7,333,270 B1 | 2/2008 | Pochapsky et al. |
| 7,341,557 B2 | 3/2008 | Cline et al. |
| 7,385,772 B2 | 6/2008 | Forkey et al. |
| 7,420,151 B2 | 9/2008 | Fengler et al. |
| 7,479,990 B2 | 1/2009 | Imaizumi et al. |
| 7,697,975 B2 | 4/2010 | Zeng |
| 7,704,206 B2 | 4/2010 | Suzuki et al. |
| 7,722,534 B2 | 5/2010 | Cline et al. |
| 7,777,191 B2 | 8/2010 | Olcott et al. |
| 7,798,955 B2 | 9/2010 | Ishihara et al. |
| 7,811,229 B2 | 10/2010 | Sugimoto |
| 7,928,352 B2 | 4/2011 | Toda |
| 8,035,067 B2 | 10/2011 | Toda |
| 8,068,899 B2 | 11/2011 | Llewellyn et al. |
| 8,140,147 B2 | 3/2012 | Maynard et al. |
| 8,285,015 B2 | 10/2012 | Demos |
| 8,294,757 B2 | 10/2012 | Yu et al. |
| 8,294,977 B2 | 10/2012 | Kirby et al. |
| 8,337,400 B2 | 12/2012 | Mizuyoshi |
| 8,361,775 B2 | 1/2013 | Flower |
| 8,408,269 B2 | 4/2013 | Fengler et al. |
| 8,408,772 B2 | 4/2013 | Li |
| 8,448,867 B2 | 5/2013 | Liu et al. |
| 8,473,035 B2 | 6/2013 | Frangioni |
| 8,498,695 B2 | 7/2013 | Westwick et al. |
| 8,630,698 B2 | 1/2014 | Fengler et al. |
| 8,721,532 B2 | 5/2014 | Takei et al. |
| 8,736,748 B2 | 5/2014 | Takita |
| 8,759,243 B2 | 6/2014 | Coffy et al. |
| 8,773,756 B2 | 7/2014 | Tesar et al. |
| 8,788,021 B1 | 7/2014 | Flusberg et al. |
| 8,790,253 B2 | 7/2014 | Sunagawa et al. |
| 8,796,699 B2 | 8/2014 | So et al. |
| 8,830,339 B2 | 9/2014 | Velarde et al. |
| 8,849,380 B2 | 9/2014 | Patwardhan |
| 8,961,403 B2 | 2/2015 | Cline et al. |
| 8,977,331 B2 | 3/2015 | Kim |
| 8,979,301 B2 | 3/2015 | Moore |
| 9,054,262 B2 | 6/2015 | Lewis et al. |
| 9,082,922 B2 | 7/2015 | Ban et al. |
| 9,125,552 B2 | 9/2015 | Dunki-Jacobs et al. |
| 9,143,746 B2 | 9/2015 | Westwick et al. |
| 9,173,554 B2 | 11/2015 | Fengler et al. |
| 9,282,305 B2 | 3/2016 | Kikuchi |
| 9,294,691 B2 | 3/2016 | Ooki |
| 9,295,392 B2 | 3/2016 | Douplik et al. |
| 9,354,370 B1 | 5/2016 | Erdogan |
| 9,357,931 B2 | 6/2016 | Nahm et al. |
| 9,386,909 B2 | 7/2016 | Fengler et al. |
| 9,407,838 B2 | 8/2016 | Butte et al. |
| 9,435,496 B2 | 9/2016 | Moore |
| 9,472,597 B2 | 10/2016 | Mohseni |
| 9,577,012 B2 | 2/2017 | Ooki |
| 9,642,532 B2 | 5/2017 | Fengler et al. |
| 9,814,378 B2 | 11/2017 | Moore |
| 10,134,815 B2 | 11/2018 | So et al. |
| 10,694,151 B2 | 6/2020 | Westwick et al. |
| 10,694,152 B2 | 6/2020 | Westwick et al. |
| 10,779,734 B2 | 9/2020 | Fengler et al. |
| 10,869,645 B2 | 12/2020 | Fengler et al. |
| 10,980,420 B2 | 4/2021 | Fengler et al. |
| 10,992,848 B2 | 4/2021 | Murray et al. |
| 11,025,867 B2 | 6/2021 | Westwick et al. |
| 11,298,024 B2 | 4/2022 | Fengler et al. |
| 2001/0016679 A1 | 8/2001 | Futatsugi et al. |
| 2001/0028458 A1 | 10/2001 | Xiao |
| 2001/0049473 A1 | 12/2001 | Hayashi |
| 2002/0013937 A1 | 1/2002 | Ostanevich et al. |
| 2002/0016533 A1 | 2/2002 | Marchitto et al. |
| 2002/0021355 A1 | 2/2002 | Utsui et al. |
| 2002/0035330 A1 | 3/2002 | Cline et al. |
| 2002/0076480 A1 | 6/2002 | Hsieh et al. |
| 2002/0138008 A1 | 9/2002 | Tsujita et al. |
| 2002/0143243 A1 | 10/2002 | Geordakoudi et al. |
| 2002/0155619 A1 | 10/2002 | Kurihara et al. |
| 2002/0156380 A1 | 10/2002 | Feld et al. |
| 2002/0161282 A1 | 10/2002 | Fulghum |
| 2002/0161283 A1 | 10/2002 | Sendai |
| 2002/0161284 A1 | 10/2002 | Tanaka |

(56) References Cited

U.S. PATENT DOCUMENTS

| | | |
|---|---|---|
| 2002/0168096 A1 | 11/2002 | Hakamata et al. |
| 2002/0175993 A1 | 11/2002 | Ueno et al. |
| 2002/0177778 A1 | 11/2002 | Averback et al. |
| 2002/0186478 A1 | 12/2002 | Watanabe et al. |
| 2002/0196335 A1 | 12/2002 | Ozawa |
| 2003/0001951 A1 | 1/2003 | Tsujita et al. |
| 2003/0002036 A1 | 1/2003 | Haan et al. |
| 2003/0042493 A1 | 3/2003 | Kazakevich |
| 2003/0063398 A1 | 4/2003 | Abe et al. |
| 2003/0080193 A1 | 5/2003 | Ryan et al. |
| 2003/0117491 A1 | 6/2003 | Avni et al. |
| 2003/0135092 A1 | 7/2003 | Cline et al. |
| 2003/0153811 A1 | 8/2003 | Muckner |
| 2003/0158470 A1 | 8/2003 | Wolters et al. |
| 2003/0191368 A1 | 10/2003 | Wang et al. |
| 2003/0216626 A1 | 11/2003 | Tsujita et al. |
| 2003/0229270 A1 | 12/2003 | Suzuki et al. |
| 2004/0006276 A1 | 1/2004 | Demos et al. |
| 2004/0010183 A1 | 1/2004 | Dhindsa |
| 2004/0021859 A1 | 2/2004 | Cunningham |
| 2004/0037454 A1 | 2/2004 | Ozawa et al. |
| 2004/0044275 A1 | 3/2004 | Hakamata |
| 2004/0046865 A1 | 3/2004 | Ueno et al. |
| 2004/0133073 A1 | 7/2004 | Berci et al. |
| 2004/0143162 A1 | 7/2004 | Krattiger et al. |
| 2004/0148141 A1 | 7/2004 | Tsujita et al. |
| 2004/0149998 A1 | 8/2004 | Henson et al. |
| 2004/0156124 A1 | 8/2004 | Okada |
| 2004/0186351 A1 | 9/2004 | Imaizumi et al. |
| 2004/0218115 A1 | 11/2004 | Kawana et al. |
| 2004/0225222 A1 | 11/2004 | Zeng et al. |
| 2004/0245350 A1 | 12/2004 | Zeng |
| 2004/0263643 A1 | 12/2004 | Imaizumi et al. |
| 2005/0011954 A1 | 1/2005 | Hennick et al. |
| 2005/0027166 A1 | 2/2005 | Matsumoto et al. |
| 2005/0051723 A1 | 3/2005 | Neagle et al. |
| 2005/0088763 A1 | 4/2005 | Weaver et al. |
| 2005/0096505 A1 | 5/2005 | Imaizumi et al. |
| 2005/0140270 A1 | 6/2005 | Henson et al. |
| 2005/0143627 A1 | 6/2005 | Cline et al. |
| 2005/0146634 A1* | 7/2005 | Silverstein ............... G02B 5/20 |
| | | 348/360 |
| 2005/0154319 A1 | 7/2005 | Cline et al. |
| 2005/0171440 A1 | 8/2005 | Maki et al. |
| 2005/0182291 A1 | 8/2005 | Hirata |
| 2005/0182321 A1 | 8/2005 | Frangioni |
| 2005/0203421 A1 | 9/2005 | Zeng et al. |
| 2005/0225656 A1 | 10/2005 | Ihama |
| 2005/0256373 A1 | 11/2005 | Bar-Or et al. |
| 2005/0259318 A1 | 11/2005 | Armstrong |
| 2005/0273011 A1 | 12/2005 | Hattery et al. |
| 2005/0280783 A1 | 12/2005 | Yamasaki et al. |
| 2005/0286130 A1 | 12/2005 | Bala |
| 2005/0288593 A1 | 12/2005 | Geordakoudi et al. |
| 2006/0002141 A1 | 1/2006 | Ouderkirk et al. |
| 2006/0004292 A1 | 1/2006 | Beylin |
| 2006/0017913 A1 | 1/2006 | Kawamata et al. |
| 2006/0089554 A1 | 4/2006 | Ishihara et al. |
| 2006/0094109 A1 | 5/2006 | Trainer |
| 2006/0108509 A1 | 5/2006 | Franigioni et al. |
| 2006/0146322 A1 | 7/2006 | Komachi et al. |
| 2006/0149133 A1 | 7/2006 | Sugimoto et al. |
| 2006/0155166 A1 | 7/2006 | Takahashi et al. |
| 2006/0211915 A1 | 9/2006 | Takeuchi et al. |
| 2006/0215406 A1 | 9/2006 | Thrailkill |
| 2006/0217594 A1 | 9/2006 | Ferguson |
| 2006/0241496 A1 | 10/2006 | Fengler et al. |
| 2006/0247537 A1 | 11/2006 | Matsumoto |
| 2006/0250696 A1 | 11/2006 | McGuire |
| 2006/0256373 A1 | 11/2006 | Schaack |
| 2006/0258910 A1 | 11/2006 | Stefanchik et al. |
| 2007/0041195 A1 | 2/2007 | Chen |
| 2007/0091634 A1 | 4/2007 | Sakurada |
| 2007/0152161 A1 | 7/2007 | Olcott et al. |
| 2007/0177152 A1 | 8/2007 | Tearney et al. |
| 2007/0203413 A1 | 8/2007 | Frangioni |
| 2007/0213593 A1 | 9/2007 | Nakaoka |
| 2007/0229309 A1 | 10/2007 | Tomita et al. |
| 2007/0276184 A1 | 11/2007 | Okawa |
| 2007/0276236 A1 | 11/2007 | Jong |
| 2008/0019615 A1 | 1/2008 | Schnee et al. |
| 2008/0021274 A1 | 1/2008 | Bayer et al. |
| 2008/0024868 A1 | 1/2008 | Okamura |
| 2008/0027280 A1 | 1/2008 | Fengler et al. |
| 2008/0039697 A1 | 2/2008 | Morishita |
| 2008/0064925 A1 | 3/2008 | Gill et al. |
| 2008/0074752 A1 | 3/2008 | Chaves et al. |
| 2008/0177140 A1 | 7/2008 | Cline et al. |
| 2008/0208006 A1 | 8/2008 | Farr |
| 2008/0246920 A1 | 10/2008 | Buczek et al. |
| 2008/0249368 A1* | 10/2008 | Takei ................... A61B 1/0655 |
| | | 600/181 |
| 2009/0012361 A1 | 1/2009 | MacKinnon et al. |
| 2009/0021739 A1 | 1/2009 | Tsujita et al. |
| 2009/0036734 A1 | 2/2009 | Dunki-Jacobs et al. |
| 2009/0040754 A1 | 2/2009 | Brukilacchio et al. |
| 2009/0052185 A1 | 2/2009 | Toriyama et al. |
| 2009/0114799 A1 | 5/2009 | Maeda |
| 2009/0114803 A1 | 5/2009 | Yamaguchi |
| 2009/0122135 A1 | 5/2009 | Matsui |
| 2009/0122152 A1 | 5/2009 | Yamaguchi et al. |
| 2009/0124854 A1 | 5/2009 | Yamaguchi et al. |
| 2009/0153797 A1 | 6/2009 | Allon et al. |
| 2009/0181339 A1 | 7/2009 | Liang et al. |
| 2009/0201577 A1 | 8/2009 | LaPlante et al. |
| 2009/0236541 A1 | 9/2009 | Lommes et al. |
| 2009/0285762 A1 | 11/2009 | Flower |
| 2009/0290149 A1 | 11/2009 | Roth |
| 2010/0061604 A1 | 3/2010 | Nahm et al. |
| 2010/0065641 A1 | 3/2010 | Liu et al. |
| 2010/0079884 A1* | 4/2010 | Gere ...................... G02B 5/201 |
| | | 359/887 |
| 2010/0087741 A1 | 4/2010 | Douplik et al. |
| 2010/0094136 A1 | 4/2010 | Nakaoka et al. |
| 2010/0110168 A1 | 5/2010 | Avni et al. |
| 2010/0110393 A1 | 5/2010 | Chen et al. |
| 2010/0111361 A1 | 5/2010 | Tan et al. |
| 2010/0121146 A1 | 5/2010 | Sugimoto |
| 2010/0125164 A1 | 5/2010 | LaBombard |
| 2010/0155487 A1 | 6/2010 | Liu et al. |
| 2010/0157039 A1 | 6/2010 | Sugai |
| 2010/0168588 A1 | 7/2010 | Matsumoto et al. |
| 2010/0177180 A1 | 7/2010 | Yamaguchi et al. |
| 2010/0198010 A1 | 8/2010 | Cline et al. |
| 2010/0206731 A1 | 8/2010 | Lau et al. |
| 2010/0208487 A1 | 8/2010 | Li |
| 2010/0277817 A1 | 11/2010 | Durell |
| 2011/0019992 A1 | 1/2011 | Orf |
| 2011/0025843 A1 | 2/2011 | Oggier et al. |
| 2011/0032350 A1 | 2/2011 | Kikuchi et al. |
| 2011/0071403 A1 | 3/2011 | Sevick-Muraca et al. |
| 2011/0073658 A1 | 3/2011 | Vassura et al. |
| 2011/0158914 A1 | 6/2011 | Yamada et al. |
| 2011/0235017 A1 | 9/2011 | Iwasaki |
| 2011/0270092 A1 | 11/2011 | Kang et al. |
| 2011/0279679 A1 | 11/2011 | Samuel et al. |
| 2011/0306877 A1 | 12/2011 | Dvorsky et al. |
| 2011/0309275 A1 | 12/2011 | Azimi et al. |
| 2012/0013773 A1 | 1/2012 | Yoshino et al. |
| 2012/0026325 A1 | 2/2012 | Bunker et al. |
| 2012/0044462 A1 | 2/2012 | Kaji |
| 2012/0150046 A1 | 6/2012 | Watson et al. |
| 2012/0292530 A1 | 11/2012 | Ono et al. |
| 2012/0305650 A1 | 12/2012 | Prpa |
| 2013/0237762 A1 | 9/2013 | Fengler et al. |
| 2013/0306880 A1* | 11/2013 | Yamano ................... G03B 9/02 |
| | | 362/293 |
| 2014/0071328 A1 | 3/2014 | Miesak |
| 2014/0078378 A1 | 3/2014 | Demers et al. |
| 2014/0111652 A1 | 4/2014 | So et al. |
| 2014/0139893 A1 | 5/2014 | Sugiyama et al. |
| 2014/0171764 A1 | 6/2014 | Kim |
| 2014/0184769 A1 | 7/2014 | Ishihara et al. |
| 2014/0186351 A1 | 7/2014 | Britta et al. |

(56) References Cited

U.S. PATENT DOCUMENTS

| | | | |
|---|---|---|---|
| 2014/0187967 A1 | 7/2014 | Wood et al. | |
| 2014/0192258 A1 | 7/2014 | Yang et al. | |
| 2014/0194687 A1 | 7/2014 | Fengler et al. | |
| 2014/0217284 A1 | 8/2014 | So et al. | |
| 2014/0261456 A1 | 9/2014 | Malackowski et al. | |
| 2014/0264025 A1 | 9/2014 | Mohseni | |
| 2015/0008390 A1 | 1/2015 | Lewis et al. | |
| 2015/0018690 A1 | 1/2015 | Kang et al. | |
| 2015/0083932 A1 | 3/2015 | Rizo et al. | |
| 2015/0230698 A1 | 8/2015 | Cline et al. | |
| 2015/0320296 A1 | 11/2015 | Morita | |
| 2015/0341551 A1 | 11/2015 | Perrin et al. | |
| 2015/0381909 A1 | 12/2015 | Butte et al. | |
| 2016/0035104 A1 | 2/2016 | Bigioi et al. | |
| 2016/0041098 A1 | 2/2016 | Hirawake et al. | |
| 2016/0044253 A1 | 2/2016 | Dainty et al. | |
| 2016/0100763 A1 | 4/2016 | Fengler et al. | |
| 2016/0173802 A1 | 6/2016 | Matsuo et al. | |
| 2016/0245750 A1 | 8/2016 | Jiang et al. | |
| 2016/0249019 A1 | 8/2016 | Westwick et al. | |
| 2016/0360956 A1 | 12/2016 | Moore | |
| 2017/0064257 A1 | 3/2017 | Westwick et al. | |
| 2017/0064258 A1 | 3/2017 | Westwick et al. | |
| 2017/0112369 A1* | 4/2017 | Czupalla | A61B 1/00193 |
| 2017/0167980 A1 | 6/2017 | Dimitriadis et al. | |
| 2017/0196527 A1 | 7/2017 | Kokubun | |
| 2017/0245803 A1 | 8/2017 | Ahmed et al. | |
| 2017/0307355 A1 | 10/2017 | Seitz et al. | |
| 2018/0199801 A1 | 7/2018 | Tsuruta | |
| 2018/0234603 A1 | 8/2018 | Moore et al. | |
| 2019/0298471 A1 | 10/2019 | Holop | |
| 2021/0166806 A1 | 6/2021 | Fengler et al. | |
| 2021/0274131 A1 | 9/2021 | Westwick et al. | |
| 2022/0030149 A1 | 1/2022 | Moore et al. | |
| 2023/0031797 A1 | 2/2023 | Fengler et al. | |
| 2023/0172444 A1* | 6/2023 | Bauer | A61B 1/0638 600/178 |
| 2024/0029869 A1 | 1/2024 | Fengler et al. | |
| 2024/0366089 A1 | 11/2024 | Fengler et al. | |
| 2024/0373115 A1 | 11/2024 | Moore et al. | |

FOREIGN PATENT DOCUMENTS

| | | | |
|---|---|---|---|
| CN | 101631508 A | 1/2010 | |
| CN | 101726980 A | 6/2010 | |
| CN | 101828139 A | 9/2010 | |
| CN | 102026668 A | 4/2011 | |
| CN | 201974160 U | 9/2011 | |
| CN | 102257510 A | 11/2011 | |
| CN | 102711652 A | 10/2012 | |
| CN | 103543609 A | 1/2014 | |
| CN | 104958111 A | 10/2015 | |
| DE | 19535114 A1 | 3/1996 | |
| DE | 19608027 A1 | 9/1996 | |
| DE | 10028233 A1 | 1/2002 | |
| DE | 20 2005 021 111 U1 | 5/2007 | |
| EP | 0512965 A1 | 11/1992 | |
| EP | 0672379 A1 | 9/1995 | |
| EP | 0774865 A2 | 5/1997 | |
| EP | 0792618 A1 | 9/1997 | |
| EP | 0671706 B1 | 6/1999 | |
| EP | 1374755 A1 | 1/2004 | |
| EP | 1 496 690 A2 | 1/2005 | |
| EP | 1883337 A1 | 2/2008 | |
| EP | 2051603 A1 | 4/2009 | |
| EP | 2859837 A1 | 4/2015 | |
| EP | 2 988 654 B1 | 6/2020 | |
| FR | 2671405 A1 | 7/1992 | |
| JP | S60-246733 A | 12/1985 | |
| JP | S61-159936 A | 7/1986 | |
| JP | H1-135349 A | 5/1989 | |
| JP | 3-97439 A | 4/1991 | |
| JP | 03-97441 A | 4/1991 | |
| JP | 03-97442 A | 4/1991 | |
| JP | 05-115435 A | 5/1993 | |
| JP | 6-125911 A | 5/1994 | |
| JP | H7-155285 A | 6/1995 | |
| JP | H7-155286 A | 6/1995 | |
| JP | H7-155290 A | 6/1995 | |
| JP | H7-155291 A | 6/1995 | |
| JP | H7-155292 A | 6/1995 | |
| JP | H7-204156 A | 8/1995 | |
| JP | H7-222712 A | 8/1995 | |
| JP | H7-250804 A | 10/1995 | |
| JP | H7-250812 A | 10/1995 | |
| JP | H7-327913 A | 12/1995 | |
| JP | H8-126605 A | 5/1996 | |
| JP | H8-140928 A | 6/1996 | |
| JP | H8-140929 A | 6/1996 | |
| JP | H8-224208 A | 9/1996 | |
| JP | H8-224209 A | 9/1996 | |
| JP | H8-224210 A | 9/1996 | |
| JP | H8-224240 A | 9/1996 | |
| JP | H8-252218 A | 10/1996 | |
| JP | H9-19408 A | 1/1997 | |
| JP | H9-66023 A | 3/1997 | |
| JP | H9-70384 A | 3/1997 | |
| JP | H9-294706 | 11/1997 | |
| JP | H9-294707 | 11/1997 | |
| JP | H10-14926 A | 1/1998 | |
| JP | H10-127563 A | 5/1998 | |
| JP | H10-151104 A | 6/1998 | |
| JP | H10-201700 A | 8/1998 | |
| JP | H10-201707 A | 8/1998 | |
| JP | H10-225426 A | 8/1998 | |
| JP | H10-225427 A | 8/1998 | |
| JP | H10-243915 A | 9/1998 | |
| JP | H10-243920 A | 9/1998 | |
| JP | H10-308114 A | 11/1998 | |
| JP | H10-309281 A | 11/1998 | |
| JP | H10-309282 A | 11/1998 | |
| JP | H10-321005 A | 12/1998 | |
| JP | H10-328129 A | 12/1998 | |
| JP | H11-47079 A | 2/1999 | |
| JP | H11-89789 A | 4/1999 | |
| JP | H11-104059 A | 4/1999 | |
| JP | H11-104060 A | 4/1999 | |
| JP | H11-104061 A | 4/1999 | |
| JP | H11-104070 A | 4/1999 | |
| JP | H11-113839 A | 4/1999 | |
| JP | H1195120 A * | 4/1999 | G01N 21/6428 |
| JP | H11-155812 A | 6/1999 | |
| JP | H11-244220 A | 9/1999 | |
| JP | H11-332819 A | 12/1999 | |
| JP | 2000-504968 A | 4/2000 | |
| JP | 2000-230903 A | 8/2000 | |
| JP | 2000-245693 A | 9/2000 | |
| JP | 2000-354583 A | 12/2000 | |
| JP | 2001-78205 A | 3/2001 | |
| JP | 2001-518241 A | 10/2001 | |
| JP | 2002-560 A | 1/2002 | |
| JP | 2002-49302 A | 2/2002 | |
| JP | 2002-244122 A | 8/2002 | |
| JP | 2003-45210 A | 2/2003 | |
| JP | 2004-24611 A | 1/2004 | |
| JP | 2004-94043 A | 3/2004 | |
| JP | 2004-163902 A | 6/2004 | |
| JP | 2004-520105 A | 7/2004 | |
| JP | 2004-247156 A | 9/2004 | |
| JP | 2004-289545 A | 10/2004 | |
| JP | 2004-292722 A | 10/2004 | |
| JP | 2005-10315 A | 1/2005 | |
| JP | 2005-58618 A | 3/2005 | |
| JP | 2005-58619 A | 3/2005 | |
| JP | 2005-58620 A | 3/2005 | |
| JP | 2005-80819 A | 3/2005 | |
| JP | 2005-81079 A | 3/2005 | |
| JP | 2005-149996 A | 6/2005 | |
| JP | 2005-292404 A | 10/2005 | |
| JP | 2005-326777 A | 11/2005 | |
| JP | 2006-3103 A | 1/2006 | |
| JP | 2006-61376 | 3/2006 | |
| JP | 2006-73767 A | 3/2006 | |

(56)  References Cited

FOREIGN PATENT DOCUMENTS

| JP | 2006-87764 A | 4/2006 |
| JP | 2006-525494 A | 11/2006 |
| JP | 2006-326153 A | 12/2006 |
| JP | 2007-29453 A | 2/2007 |
| JP | 2007-72392 A | 3/2007 |
| JP | 2007-79528 A | 3/2007 |
| JP | 2007-89840 A | 4/2007 |
| JP | 2008-48787 A | 3/2008 |
| JP | 2009-259703 A | 11/2009 |
| JP | 2010-107751 A | 5/2010 |
| JP | 2010-117442 A | 5/2010 |
| JP | 2010-524194 A | 7/2010 |
| JP | 2011-500921 A | 1/2011 |
| JP | 2011-72424 A | 4/2011 |
| JP | 2011-110272 A | 6/2011 |
| JP | 2011-161046 A | 8/2011 |
| JP | 2011-169819 A | 9/2011 |
| JP | 2011-528918 A | 12/2011 |
| JP | 2013-113858 A | 6/2013 |
| JP | 5231625 B2 | 7/2013 |
| JP | 2013-541370 A | 11/2013 |
| JP | 2014-123941 A | 7/2014 |
| JP | 2015-16332 A | 1/2015 |
| JP | 2016-7234 A | 1/2016 |
| JP | 5859578 B2 | 2/2016 |
| RU | 99592 U1 | 11/2010 |
| WO | WO-1993/04648 A1 | 3/1993 |
| WO | WO-1994/13191 A1 | 6/1994 |
| WO | WO-1995/26673 A2 | 10/1995 |
| WO | WO-1998/24360 A1 | 6/1998 |
| WO | WO-1999/01749 A1 | 1/1999 |
| WO | WO-1999/53832 A1 | 10/1999 |
| WO | WO-2000/42910 A1 | 7/2000 |
| WO | WO-2000/54652 A1 | 9/2000 |
| WO | WO-2002/007587 A2 | 1/2002 |
| WO | WO-2002/050518 A2 | 6/2002 |
| WO | WO-2003/059159 A2 | 7/2003 |
| WO | WO-2006/116847 A1 | 11/2006 |
| WO | WO-2007070382 A2 * | 6/2007 | ............. G02B 21/10 |
| WO | WO-2007/081707 A2 | 7/2007 |
| WO | WO-2008/011722 A1 | 1/2008 |
| WO | WO-2008/071240 A1 | 6/2008 |
| WO | WO-2009/033021 A2 | 3/2009 |
| WO | WO-2011120688 A1 * | 10/2011 | ........... A61B 1/0646 |
| WO | WO-2013/160279 A1 | 10/2013 |
| WO | WO-2014/066906 A1 | 5/2014 |
| WO | WO-2014/176375 A2 | 10/2014 |
| WO | WO-2015/164774 A1 | 10/2015 |
| WO | WO-2016/055837 A1 | 4/2016 |

OTHER PUBLICATIONS

Alfano, R.R. et al. (Oct. 1987). "Fluorescence Spectra From Cancerous and Normal Human Breast and Lung Tissues," IEEE Journal of Quantum Electronics QE-23(10):1806-1811.

Andersson-Engels, S. et al. (Mar. 1989). "Tissue Diagnostics Using Laser Induced Fluorescence," Ber. Bunsenges Physical Chemistry 93(3):335-342.

Australian Notice of Acceptance for Patent Application mailed on Jun. 26, 2019 for Patent Application No. 2016351730 filed on Nov. 10, 2016, three pages.

Australian Office Action mailed on Jun. 28, 2018 for Australian Patent Application No. 2016351730 filed on Nov. 10, 2016, five pages.

Australian Office Action mailed on May 10, 2019 for Australian Patent Application No. 2016351730 filed on Nov. 10, 2016, ten pages.

Bhunchet, E. et al. (Apr. 2002). "Fluorescein Electronic Endoscopy: A Novel Method for Detection of Early Stage Gastric Cancer Not Evident to Routine Endoscopy," Gastrointestinal Endoscopy 55(4):562-571.

Brazilian Office Action mailed Aug. 5, 2019, for Patent Application No. BR112013022997-7, filed Mar. 8, 2012, 4 pages.

Canadian Office Action mailed on Feb. 1, 2017 for Canadian Patent Application No. 171282, filed on Oct. 27, 2016, two pages.

Canadian Office Action mailed on Feb. 19, 2019 for CA Patent Application No. 2,998,920 filed on Mar. 16, 2018, four pages.

Canadian Office Action mailed on Nov. 5, 2019, for Canadian Patent Application No. 3,027,592, filed on Jun. 14, 2017, four pages.

Chinese Notice of Allowance mailed on Jun. 19, 2017 for Chinese Patent Application No. 201280022284.3, filed on Nov. 7, 2013, four pages.

Chinese Office Action mailed on Jul. 29, 2016 for Chinese Patent Application No. 201280022284.3 filed on Mar. 8, 2012, eight pages.

Chinese Office Action mailed on Mar. 14, 2017 for Chinese Patent Application No. 201280022284.3, filed on Nov. 7, 2013, seven pages.

Chinese Office Action mailed on Nov. 24, 2015 for Chinese Patent Application No. 201280022284.3 filed on Mar. 8, 2012, sixteen pages.

Chinese Office Action mailed on Sep. 26, 2018 for Chinese Patent Application No. 2018092001857100, filed on Sep. 4, 2017, nineteen pages.

Dawson, J.B et al. (Jul. 1980). "A Theoretical and Experimental Study of Light Absorption and Scattering by In Vivo Skin," Phys. Med. Biol. 25(4):695-709.

Decision to Grant a Patent dated Jun. 29, 2020, directed to JP Application No. 2018-516161; 6 pages.

Decision to Grant a Patent mailed Jul. 16, 2021, directed to JP Application No. 2019-540067; 6 pages.

Decision to Grant dated Jul. 18, 2019, directed to EP Application No. 09819758.5; 2 pages.

European Extended Search Report dated Jan. 14, 2020, for Patent Application No. 17812362.6, filed Jun. 14, 2017, 8 pages.

European Extended Search Report mailed May 7, 2019, for Patent Application No. 16 863 277.6, filed Nov. 10, 2016, seven pages.

European Extended Search Report mailed Oct. 16, 2019, for Patent Application No. 17743524.5, filed Jan. 26, 2017, four pages.

European Notice of Allowance mailed on Feb. 28, 2018 for EP Patent Application No. 12754208.2 filed Oct. 4, 2013, six pages.

European Notice of Allowance mailed on Jul. 12, 2018 for EP Patent Application No. 12754208.2 filed Oct. 4, 2013, two pages.

European Notice of Allowance mailed on Jun. 22, 2017 for EP Patent Application No. 08706262.6 filed on Aug. 21, 2009, two pages.

European Notice of Allowance mailed on Mar. 18, 2019 for EP Patent Application No. 09819758.5, filed on May 4, 2011, seven pages.

European Notice of Allowance mailed on Mar. 6, 2018 for EP Patent Application No. 13180297.7 filed Aug. 13, 2013, seven pages.

European Notice of Allowance mailed on May 25, 2018 for EP Patent Application No. 13180297.7 filed Aug. 13, 2013, two pages.

European Notice of Allowance mailed on Nov. 25, 2016 for EP Patent Application No. 08706262.6 filed on Aug. 21, 2009, eight pages.

European Office Action mailed on Apr. 13, 2017, for EP Patent Application No. 12754208.2 filed on Oct. 4, 2013, five pages.

European Office Action mailed on Apr. 6, 2017, for EP Patent Application No. 09819758.5, filed on May 4, 2011, five pages.

European Office Action mailed on Dec. 3, 2015 for EP Patent Application No. 08706262.6 filed on Jan. 23, 2008, fifteen pages.

European Office Action mailed on Jan. 23, 2017 for EP Patent Application No. 16186321.2 filed on Aug. 30, 2016, two pages.

European Office Action mailed on Nov. 19, 2015 for EP Patent Application No. 07 785 001.4, filed on Jul. 30, 2007, four pages.

European Office Action mailed on Nov. 3, 2015 for EP Patent Application No. 12754208.2 filed Oct. 4, 2013, four pages.

European Office Action mailed on Sep. 29, 2015, for EP Patent Application No. 09721252.6 filed Mar. 18, 2009; five pages.

European Search Report mailed on Dec. 21, 2016 for EP Patent Application No. 16186321.2 filed on Aug. 30, 2016, nine pages.

European Search Report mailed on Feb. 18, 2019 for EP Patent Application No. 18178620.3 filed on Jun. 19, 2018, eight pages.

European Search Report mailed on Jan. 24, 2012 for EP Patent Application No. 07785001.4 filed on Jul. 30, 2007, seven pages.

(56) References Cited

OTHER PUBLICATIONS

European Search Report mailed on Jul. 17, 2014 for EP Patent Application No. 09721252.6 filed Mar. 18, 2009, eleven pages.

European Search Report mailed on Oct. 1, 2014 for EP Patent Application No. 12754208.2 filed on Mar. 8, 2012, five pages.

European Search Report mailed on Oct. 9, 2013, for European Patent Application No. 06721854.5, filed on May 4, 2005, seven pages.

European Search Report mailed on Sep. 20, 2013 for EP Patent Application No. 08706262.6 filed on Jan. 23, 2008, five pages.

Extended European Search Report dated Oct. 14, 2020, directed to EP Application No. 17895908.6; 8 pages.

Fengler et al., U.S. Advisory Action dated Dec. 20, 2019, directed to U.S. Appl. No. 15/416,876; 5 pages.

Fengler et al., U.S. Advisory Action dated Nov. 2, 2020, directed to U.S. Appl. No. 15/416,876; 5 pages.

Fengler et al., U.S. Notice of Allowance and Fee(s) Due mailed Aug. 18, 2020, directed to U.S. Appl. No. 15/623,100; 7 pages.

Fengler et al., U.S. Notice of Allowance and Fee(s) Due mailed Dec. 2, 2021, directed to U.S. Appl. No. 17/234,461; 8 pages.

Fengler et al., U.S. Notice of Allowance and Fee(s) Due mailed Dec. 4, 2020, directed to U.S. Appl. No. 15/416,876; 9 pages.

Fengler et al., U.S. Office Action dated Feb. 24, 2022, directed to U.S. Appl. No. 16/951,684; 12 pages.

Fengler et al., U.S. Office Action dated Jul. 15, 2020, directed to U.S. Appl. No. 15/416,876; 20 pages.

Fengler et al., U.S. Restriction Requirement dated Oct. 13, 2021, directed to U.S. Appl. No. 16/951,684; 7 pages.

Fengler et al., U.S. Restriction Requirement dated Oct. 17, 2018, directed to U.S. Appl. No. 15/623,100; 7 pages.

First Office Action mailed Jul. 30, 2021, directed to JP Application No. 2020-128414; 8 pages.

Georgakoudi, I et al. (2003). "Quantitative Characterization of Biological Tissue Using Optical Spectroscopy," in Chapter 31 of *Biomedical Photonics Handbook*, Tuan Vo-Dinh (ed.), CRC Press, New York, thirty three pages.

Georgakoudi, I et al. (Apr. 2005). "Characterization of Dysplastic Tissue Morphology and Biochemistry in Barrett's Esophagus using Diffuse Reflectance and Light Scattering Spectroscopy," Techniques in Gastrointestinal Endoscopy 7(2):100-105.

Hubel, P.M. et al. (2004). "Spatial Frequency Response of Color Image Sensors: Bayer Color Filters and Foveon X3," Proceedings of SPIE 5301:402-406.

Hung, J. et al. (1991). "Autofluorescence of Normal and Malignant Bronchial Tissue," Lasers in Surgery and Medicine 11(2):99-105.

Indian Office Action dated Jan. 31, 2018 for Indian Patent Application No. 6532/DELNP/2010 filed on Sep. 16, 2010, five pages.

Indian Office Action dated Jun. 26, 2018 for Indian Patent Application No. 8678/DELNP/2013 filed on Mar. 8, 2012, five pages.

Intention to Grant dated Feb. 25, 2022, directed to EP Application No. 17 743 524.5; 7 pages.

Intention to Grant dated May 17, 2021, directed to EP Application No. 16 186 321.2; 7 pages.

International Preliminary Report on Patentability mailed Aug. 22, 2019, directed to International Application No. PCT/CA2017/050564; 9 pages.

International Preliminary Report on Patentability mailed on Dec. 27, 2018 for International Patent Application No. PCT/CA2017/050734 filed on Jun. 14, 2017, six pages.

International Preliminary Report on Patentability mailed on Feb. 3, 2009 for International Patent Application No. PCT/CA2007/001335 filed on Jul. 30, 2007, five pages.

International Preliminary Report on Patentability mailed on May 24, 2018 for International Patent Application No. PCT/CA2016/051315 filed on Nov. 10, 2016, nine pages.

International Preliminary Report on Patentability mailed on Nov. 6, 2007 for International Patent Application No. PCT/CA2006/000669, filed on Apr. 27, 2006, nine pages.

International Preliminary Report on Patentability mailed on Sep. 21, 2010 for International Patent Application No. PCT/US2009/037506, filed on Mar. 18, 2009, seven pages.

International Search Report and Written Opinion mailed on Apr. 24, 2017 for International Patent Application No. PCT/CA2017/050083, filed on Jan. 26, 2017, seven pages.

International Search Report and written Opinion mailed on Feb. 10, 2017 for International Patent Application No. PCT/CA2016/051315 filed on Nov. 10, 2016, thirteen pages.

International Search Report and Written Opinion mailed on Sep. 18, 2017 for International Patent Application No. PCT/CA2017/050734, filed on Jun. 14, 2017, eight pages.

International Search Report mailed Oct. 24, 2017, for Patent Application No. PCT/CA2017/050564, mailed May 10, 2017, six pages.

International Search Report mailed on Aug. 3, 2006, for International Patent Application No. PCT/CA2006/000669, filed on Apr. 27, 2006, three pages.

International Search Report mailed on Aug. 3, 2012, for International Patent Application No. PCT/IB2012/000601, filed on Mar. 8, 2012, three pages.

International Search Report mailed on Dec. 7, 2007, for International Patent Application No. PCT/CA2007/001335, filed on Jul. 30, 2007, two pages.

International Search Report mailed on Jan. 21, 2002 for International Patent Application No. PCT/US2001/022198, filed on Jul. 13, 2001, three pages.

International Search Report mailed on Jul. 22, 2009 for International Patent Application No. PCT/US09/37506, filed on Mar. 18, 2009, two pages.

International Search Report mailed on May 13, 2008 for Intentional Patent Application No. PCT/CA2008/00015, filed on Jan. 8, 2008, one page.

Invitation to Pay additional Fees and, where Applicable, Protest Fee, mailed Jul. 4, 2017, for Patent Application No. PCT/CA2017/050564, filed May 10, 2017, two pages.

Invitation to Pay additional Fees and, where Applicable, Protest Fee, mailed on Dec. 22, 2016 for International Patent Application No. PCT/CA2016/051315, filed on Nov. 10, 2016, two pages.

Japanese Final Office Action mailed on Aug. 2, 2013 for Japanese Application No. 2008-509275, filed on Apr. 27, 2006, four pages.

Japanese Notice of Allowance mailed on Apr. 2, 2018 for Japanese Patent Application No. 2017-018858 filed on Feb. 3, 2017, six pages.

Japanese Notice of Allowance mailed on Jan. 5, 2017 for Japanese Patent Application No. 2015-238784, filed on Dec. 7, 2015, six pages.

Japanese Notice of Allowance mailed on Nov. 17, 2017 for Japanese Application No. 2016-253736 filed on Dec. 27, 2016, six pages.

Japanese Notice of Allowance mailed on Nov. 28, 2016 for Japanese Patent Application No. 2015-245598, filed on Mar. 8, 2012, six pages.

Japanese Office Action mailed on Apr. 20, 2012 for Japanese Patent Application No. 2011-500921, filed Mar. 18, 2009, four pages.

Japanese Office Action mailed on Apr. 3, 2015 for Japanese Patent Application No. 2013-058356, filed Mar. 18, 2009, four pages.

Japanese Office Action mailed on Dec. 8, 2017 for Japanese Patent Application No. 2017-018858 filed on Feb. 3, 2017, six pages.

Japanese Office Action mailed on Feb. 17, 2012 for Japanese Application No. 2008-509275, filed on Apr. 27, 2006, six pages.

Japanese Office Action mailed on Jul. 12, 2019, for Patent Application No. 2018-516161, filed Nov. 10, 2016, twenty-one pages.

Japanese Office Action mailed on Jul. 22, 2014 for Japanese Patent Application No. 2013-557187 filed Mar. 8, 2012, seven pages.

Japanese Office Action mailed on Mar. 9, 2015 for Japanese Patent Application No. 2013-557187, filed Mar. 8, 2012, five pages.

Japanese Office Action mailed on May 26, 2014 in Japanese Patent Application No. 2013-058356, filed on Mar. 18, 2009, three pages.

Japanese Office Action mailed on Nov. 11, 2011 for Japanese Application No. 2009-521077, filed on Jul. 30, 2007, four pages.

Japanese Office Action mailed on Sep. 14, 2012 for Japanese Application No. 2008-509275, filed on Apr. 27, 2006, seven pages.

Japanese Office Action mailed on Sep. 19, 2014 for Japanese Application No. 2013-246636, filed on Apr. 27, 2006, six pages.

(56)　　　　　References Cited

OTHER PUBLICATIONS

Japanese Office mailed on Dec. 26, 2012 for Japanese Patent Application No. 2011-500921, filed on Mar. 18, 2009, two pages.
Kolaman, A. et al. (2016). "Amplitude Modulated Video Camera— Light Separation in Dynamic Scenes," IEEE Conference on Computer Vision and Pattern Recognition (CVPR), located at https://www.cv-foundation.org/openaccess/content_cvpr_2016/app/S15-50. pdf last visited on Jun. 8, 2020, nine pages.
Korean Decision on the Trial Against Final Rejection from the Intellectual Property Tribunal (IPT) mailed on Sep. 25, 2017 for Korean Patent Application No. 2013-7026479, filed on Oct. 7, 2013, seventeen pages.
Korean Notice of Allowance mailed on Dec. 13, 2017 for Korean Patent Application No. 10-2017-7008654, filed on Mar. 29, 2017, three pages.
Korean Notice of Allowance mailed on Jan. 2, 2017 for Korean Patent Application No. 10-2015-7033310, filed on Nov. 20, 2015, three pages.
Korean Office Action mailed on Aug. 20, 2015 for Korean Patent Application No. 2013-7026479 filed on Mar. 8, 2012, three pages.
Korean Office Action mailed on Aug. 30, 2016 for Korean Patent Application No. 10-2015-7033310 filed on Mar. 8, 2012, seven pages.
Korean Office Action mailed on Dec. 8, 2015 for Korean Patent Application No. 20157033310 filed on Mar. 8, 2012, seven pages.
Korean Office Action mailed on Jun. 27, 2017 for Korean Patent Application No. 2017-7008654, filed on Mar. 29, 2017, ten pages.
Lyon, R.E. et al. (2002). "Eyeing the Camera: Into the Next Century," 10 Color and Imaging Conference Final Program & Proceedings 349-355.
Moore et al., U.S. Advisory Action dated May 19, 2020, directed to U.S. Appl. No. 15/591,909; 3 pages.
Moore et al., U.S. Notice of Allowance and Fee(s) due mailed Jun. 1, 2021, directed to U.S. Appl. No. 15/591,909; 6 pages.
Moore et al., U.S. Notice of Allowance and Fee(s) due mailed Mar. 5, 2019, directed to U.S. Appl. No. 15/348,664; 10 pages.
Moore et al., U.S. Office Action dated Nov. 19, 2020, directed to U.S. Appl. No. 15/591,909; 13 pages.
Moore et al., U.S. Office Action dated Oct. 17, 2019, directed to U.S. Appl. No. 16/441,493; 8 pages.
Murray et al., U.S. Office Action dated Aug. 31, 2020, directed to U.S. Appl. No. 16/746,539; 16 pages.
Murray et al., U.S. Notice of Allowance and Fee(s) Due mailed Dec. 22, 2020, directed to U.S. Appl. No. 16/746,539; 7 pages.
Notice of Allowance and Fee(s) Due mailed May 19, 2020, directed to U.S. Appl. No. 15/584,405; 9 pages.
Notice of Allowance dated Jan. 13, 2020, directed to CN Application No. ZL201710785223.7, 6 pages.
Notice of Allowance dated Oct. 29, 2019, directed to CA Application No. 2,998,920, 1 page.
Notice of Reasons for Refusal dated Apr. 1, 2022, directed to JP Application No. 2020-128414; 11 pages.
Notice of Reasons for Refusal dated Feb. 12, 2021, directed to JP Application No. 2019-540067; 13 pages.
Notification to Grant Patent Right for Invention dated Mar. 31, 2021, directed to CN Application No. 201680066060.0; 8 pages.
Notification to Pay Restoration Fee for Unity dated Apr. 7, 2020, directed to CN Application No. 201680066060.0, 2 pages.
Office Action dated Feb. 25, 2022, directed to EP Application No. 18 178 620.3; 4 pages.
Office Action dated Jan. 10, 2020, directed to JP Application No. 2018-516161; 5 pages.
Office Action dated Jul. 2, 2020, directed to CN Application No. 201680066060.0; 30 pages.
Office Action dated Jul. 6, 2020, directed to CA Application No. 3,009,419; 3 pages.
Office Action dated Jun. 16, 2021, directed to EP Application No. 16 863 277.6; 5 pages.
Office Action dated Mar. 16, 2020, directed to BR Application No. 112013022997-7, 6 pages.

Office Action dated Nov. 18, 2020, directed to CA Application No. 3,027,592; 3 pages.
Office Action dated Oct. 1, 2021, directed to EP Application No. 17 895 908.6; 4 pages.
Office Action dated Sep. 16, 2020, directed to EP Application No. 16 186 321.2; 4 pages.
Russian Notice of Allowance mailed on Aug. 19, 2016 for Russian Patent Application No. 2013144845/07, filed on Mar. 8, 2012, thirteen pages.
Sensitization (photography), definition from Wikipedia, original language German, 6 pages.
Török, B. et al. (May 1996). "Simultane digitale Indocyaningrün— und Fluoreszeinangiographie (Simultaneous Digital ICG and Fluorescein Angiography)," Klin Monatsbl Augenheilkd 208(5):333-336.
U.S. Ex Parte Quayle Action mailed on Mar. 23, 2020, directed to U.S. Appl. No. 15/584,405; 5 pages.
U.S. Final Office Action mailed Feb. 4, 2020, directed to U.S. Appl. No. 15/591,909; 13 pages.
U.S. Final Office Action mailed Feb. 7, 2020, directed to U.S. Appl. No. 15/343,038; 16 pages.
U.S. Final Office Action mailed on Apr. 24, 2015 for U.S. Appl. No. 12/933,512, filed Nov. 24, 2010, nineteen pages.
U.S. Final Office Action mailed on Aug. 10, 2017 for U.S. Appl. No. 15/343,034, filed Nov. 3, 2016, twelve pages.
U.S. Final Office Action mailed on Aug. 11, 2017 for U.S. Appl. No. 14/860,687, filed Sep. 21, 2015, seventeen pages.
U.S. Final Office Action mailed on Aug. 7, 2017 for U.S. Appl. No. 15/343,038, filed Nov. 3, 2016, eleven pages.
U.S. Final Office Action mailed on Dec. 14, 2018 for U.S. Appl. No. 15/584,405, filed May 2, 2017, seven pages.
U.S. Final Office Action mailed on Feb. 1, 2018 for U.S. Appl. No. 15/584,405, filed May 2, 2017, ten pages.
U.S. Final Office Action mailed on Feb. 27, 2017 for U.S. Appl. No. 15/247,419, filed Aug. 25, 2016, ten pages.
U.S. Final Office Action mailed on Jan. 11, 2019 for U.S. Appl. No. 15/343,038, filed Nov. 3, 2016, twelve pages.
U.S. Final Office Action mailed on Jan. 14, 2019 for U.S. Appl. No. 14/860,687, filed Sep. 21, 2015, sixteen pages.
U.S. Final Office Action mailed on Jan. 22, 2019 for U.S. Appl. No. 15/343,034, filed Nov. 3, 2016, twelve pages.
U.S. Final Office Action mailed on Jul. 23, 2008 for U.S. Appl. No. 11/122,267, filed May 4, 2016, six pages.
U.S. Final Office Action mailed on Jul. 25, 2019, directed to U.S. Appl. No. 15/416,876; 13 pages.
U.S. Final Office Action mailed on Jun. 18, 2015 for U.S. Appl. No. 14/154,177, filed Jan. 13, 2014, eight pages.
U.S. Final Office Action mailed on Jun. 5, 2014 for U.S. Appl. No. 12/761,462, filed Apr. 16, 2010, fourteen pages.
U.S. Final Office Action mailed on Mar. 22, 2016 for U.S. Appl. No. 14/873,842, filed Oct. 2, 2015, eighteen pages.
U.S. Final Office Action mailed on May 11, 2011 for U.S. Appl. No. 11/412,715, filed Apr. 26, 2006, eight pages.
U.S. Final Office Action mailed on May 21, 2012 for U.S. Appl. No. 11/964,330, filed Dec. 26, 2007, twelve pages.
U.S. Final Office Action mailed on Nov. 24, 2009 for U.S. Appl. No. 11/009,965, filed Dec. 10, 2004, fourteen pages.
U.S. Non-Final Office Action mailed on Apr. 2, 2009 for U.S. Appl. No. 11/009,965, filed Dec. 10, 2004, thirteen pages.
U.S. Non-Final Office Action mailed on Apr. 3, 2019 for U.S. Appl. No. 15/416,876, filed Jan. 26, 2017, thirteen pages.
U.S. Non-Final Office Action mailed on Aug. 15, 2018 for U.S. Appl. No. 15/348,664, filed Nov. 10, 2016, twelve pages.
U.S. Non-Final Office Action mailed on Aug. 16, 2013 for U.S. Appl. No. 12/761,462, filed Apr. 16, 2010, ten pages.
U.S. Non-Final Office Action mailed on Aug. 16, 2013 for U.S. Appl. No. 12/761,523, filed Apr. 16, 2010, nine pages.
U.S. Non-Final Office Action mailed on Aug. 2, 2019 for U.S. Appl. No. 15/623,100, filed Jun. 14, 2017, twelve pages.
U.S. Non-Final Office Action mailed on Aug. 21, 2019 for U.S. Appl. No. 15/584,405, filed May 2, 2017, six pages.
U.S. Non-Final Office Action mailed on Aug. 23, 2019 for U.S. Appl. No. 14/860,687, filed Sep. 21, 2015, fourteen pages.

(56) References Cited

OTHER PUBLICATIONS

U.S. Non-Final Office Action mailed on Aug. 23, 2019 for U.S. Appl. No. 15/343,034, filed Nov. 3, 2016, eighteen pages.
U.S. Non-Final Office Action mailed on Aug. 23, 2019 for U.S. Appl. No. 15/343,038, filed Nov. 3, 2016, fourteen pages.
U.S. Non-Final Office Action mailed on Aug. 6, 2019, for U.S. Appl. No. 15/591,909, filed May 10, 2017, 9 pages.
U.S. Non-Final Office Action mailed on Dec. 10, 2010 for U.S. Appl. No. 11/412,715, filed Apr. 26, 2006, ten pages.
U.S. Non-Final Office Action mailed on Dec. 14, 2011 for U.S. Appl. No. 11/412,715, filed Apr. 26, 2006, eight pages.
U.S. Non-Final Office Action mailed on Feb. 1, 2017 for U.S. Appl. No. 14/860,687, filed Sep. 21, 2015, fifteen pages.
U.S. Non-Final Office Action mailed on Feb. 3, 2010 for U.S. Appl. No. 11/626,308, filed Jan. 23, 2007, eleven pages.
U.S. Non-Final Office Action mailed on Feb. 5, 2019 for U.S. Appl. No. 15/623,100, filed Jun. 14, 2017, eleven pages.
U.S. Non-Final Office Action mailed on Jan. 16, 2020, for U.S. Appl. No. 15/416,876, filed Jan. 26, 2017, thirteen pages.
U.S. Non-Final Office Action mailed on Jan. 2, 2008 for U.S. Appl. No. 11/122,267, filed May 4, 2005, five pages.
U.S. Non-Final Office Action mailed on Jan. 20, 2016 for U.S. Appl. No. 14/629,473, filed Feb. 23, 2015, fifteen pages.
U.S. Non-Final Office Action mailed on Jan. 26, 2017 for U.S. Appl. No. 15/343,034, filed Nov. 3, 2016, seventeen pages.
U.S. Non-Final Office Action mailed on Jan. 27, 2017 for U.S. Appl. No. 15/343,038, filed Nov. 3, 2016, fifteen pages.
U.S. Non-Final Office Action mailed on Jul. 17, 2003 for U.S. Appl. No. 09/905,642, filed Jul. 13, 2001, six pages.
U.S. Non-Final Office Action mailed on Jul. 2, 2013 for U.S. Appl. No. 12/933,512, filed Nov. 24, 2010, twelve pages.
U.S. Non-Final Office Action mailed on Jun. 1, 2007 for U.S. Appl. No. 10/899,648, filed Jul. 26, 2004, seven pages.
U.S. Non-Final Office Action mailed on Jun. 20, 2008 for U.S. Appl. No. 11/009,398, filed Dec. 10, 2004, fifteen pages.
U.S. Non-Final Office Action mailed on Jun. 23, 2010 for U.S. Appl. No. 11/009,965, filed Dec. 10, 2004, fifteen pages.
U.S. Non-Final Office Action mailed on Jun. 27, 2014 for U.S. Appl. No. 13/415,561, filed Mar. 3, 2012, fourteen pages.
U.S. Non-Final Office Action mailed on Jun. 5, 2018 for U.S. Appl. No. 14/860,687, filed Sep. 21, 2015, eighteen pages.
U.S. Non-Final Office Action mailed on Jun. 8, 2018 for U.S. Appl. No. 15/343,034, filed Nov. 3, 2016, thirteen pages.
U.S. Non-Final Office Action mailed on Jun. 8, 2018 for U.S. Appl. No. 15/584,405, filed May 2, 2017, eight pages.
U.S. Non-Final Office Action mailed on Jun. 9, 2011 for U.S. Appl. No. 11/830,323, filed Jul. 30, 2007, five pages.
U.S. Non-Final Office Action mailed on May 18, 2004 for U.S. Appl. No. 10/050,601, filed Jan. 15, 2002, eight pages.
U.S. Non-Final Office Action mailed on May 25, 2018 for U.S. Appl. No. 15/343,038, filed Nov. 3, 2016, eleven pages.
U.S. Non-Final Office Action mailed on May 5, 2020, for U.S. Appl. No. 15/623,100, filed Jun. 14, 2017, twelve pages.
U.S. Non-Final Office Action mailed on Nov. 5, 2014 for U.S. Appl. No. 13/930,225, filed Jun. 28, 2013, six pages.
U.S. Non-Final Office Action mailed on Nov. 23, 2009 for U.S. Appl. No. 11/969,974, filed Jan. 7, 2008, seven pages.
U.S. Non-Final Office Action mailed on Oct. 23, 2013 for U.S. Appl. No. 13/415,561, filed Mar. 8, 2012, ten pages.
U.S. Non-Final Office Action mailed on Oct. 5, 2016 for U.S. Appl. No. 15/247,419, filed Aug. 25, 2016, eight pages.
U.S. Non-Final Office Action mailed on Oct. 7, 2011 for U.S. Appl. No. 11/964,330, filed Dec. 26, 2007; ten pages.
U.S. Non-Final Office Action mailed on Sep. 12, 2014 for U.S. Appl. No. 14/154,177, filed Jan. 13, 2014, four pages.
U.S. Non-Final Office Action mailed on Sep. 25, 2017 for U.S. Appl. No. 15/584,405, filed May 2, 2017, eight pages.
U.S. Non-Final Office Action mailed on Sep. 6, 2016 for U.S. Appl. No. 14/873,842, filed Oct. 2, 2015, seven pages.

U.S. Non-Final Office Action with Restriction Requirement mailed on Mar. 4, 2011 for U.S. Appl. No. 11/830,323, filed Jul. 30, 2007, nine pages.
U.S. Notice of Allowance mailed on Apr. 7, 2004 for U.S. Appl. No. 09/905,642, filed Jul. 13, 2001, six pages.
U.S. Notice of Allowance mailed on Aug. 26, 2004 for U.S. Appl. No. 10/050,601, filed Jan. 15, 2002, eight pages.
U.S. Notice of Allowance mailed on Aug. 6, 2015 for U.S. Appl. No. 13/853,656, filed Mar. 29, 2013, seven pages.
U.S. Notice of Allowance mailed on Dec. 10, 2012 for U.S. Appl. No. 11/964,330, filed Dec. 26, 2007, seven pages.
U.S. Notice of Allowance mailed on Dec. 30, 2016 for U.S. Appl. No. 14/873,842, filed Oct. 2, 2015, eleven pages.
U.S. Notice of Allowance mailed on Feb. 14, 2020, for U.S. Appl. No. 14/860,687, filed Sep. 21, 2015, eight pages.
U.S. Notice of Allowance mailed on Feb. 14, 2020, for U.S. Appl. No. 15/343,034, filed Nov. 3, 2016, seven pages.
U.S. Notice of Allowance mailed on Feb. 25, 2010 for U.S. Appl. No. 11/969,974, filed Jan. 7, 2008, four pages.
U.S. Notice of Allowance mailed on Jan. 2, 2008 for U.S. Appl. No. 10/899,648, filed Jul. 26, 2004, three pages.
U.S. Notice of Allowance mailed on Jul. 10, 2017 for U.S. Appl. No. 15/247,419, filed Aug. 25, 2016, eight pages.
U.S. Notice of Allowance mailed on Jun. 25, 2015 for U.S. Appl. No. 12/933,512, filed Nov. 24, 2010 fourteen pages.
U.S. Notice of Allowance mailed on Mar. 10, 2005 for U.S. Appl. No. 10/050,601, filed Jan. 15, 2002, five pages.
U.S. Notice of Allowance mailed on Mar. 12, 2020, for U.S. Appl. No. 16/441,493, filed Jun. 14, 2019, 8 pages.
U.S. Notice of Allowance mailed on Mar. 22, 2013 for U.S. Appl. No. 11/964,330, filed Dec. 26, 2007, eight pages.
U.S. Notice of Allowance mailed on Mar. 28, 2016 for U.S. Appl. No. 13/853,656, filed Mar. 29, 2013, eight pages.
U.S. Notice of Allowance mailed on May 18, 2015 for U.S. Appl. No. 13/930,225, filed Jun. 28, 2013, nine pages.
U.S. Notice of Allowance mailed on Nov. 23, 2015 for U.S. Appl. No. 13/853,656, filed Mar. 29, 2013, seven pages.
U.S. Notice of Allowance mailed on Oct. 10, 2014 for U.S. Appl. No. 12/761,462, filed Apr. 16, 2010, ten pages.
U.S. Notice of Allowance mailed on Oct. 5, 2007 for U.S. Appl. No. 10/899,648, filed Jul. 26, 2004, six pages.
U.S. Notice of Allowance mailed on Sep. 10, 2013 for U.S. Appl. No. 11/412,715, filed Apr. 26, 2006, eight pages.
U.S. Notice of Allowance mailed on Sep. 14, 2012 for U.S. Appl. No. 11/830,323, filed Jul. 30, 2007, eight pages.
U.S. Office Action dated Apr. 3, 2020, directed to U.S. Appl. No. 16/746,539; 15 pages.
U.S. Appl. No. 15/810,911, filed Nov. 13, 2017.
U.S. Restriction Requirement mailed Jan. 17, 2019, for U.S. Appl. No. 15/591,909, filed May 10, 2017, 7 pages.
Westwick et al., U.S. Office Action dated Aug. 27, 2020, directed to U.S. Appl. No. 15/343,038; 16 pages.
Westwick et al., U.S. Office Action dated Dec. 16, 2021, directed to U.S. Appl. No. 17/243,002; 19 pages.
Written Opinion of the International Searching Authority mailed Oct. 24, 2017, for Patent Application No. PCT/CA2017/050564, seven pages.
Written Opinion of the International Searching Authority mailed on Aug. 3, 2006 for International Patent Application No. PCT/CA2006/000669, filed on Apr. 27, 2006, eight pages.
Written Opinion of the International Searching Authority mailed on Dec. 7, 2007 for International Patent Application No. PCT/CA2007/001335, filed on Jul. 30, 2007, four pages.
Moore et al., U.S. Restriction Requirement dated May 3, 2018, directed to U.S. Appl. No. 15/348,664; 5 pages.
Decision of Refusal dated Nov. 11, 2022, directed to JP Application No. 2020-128414; 5 pages.
Decision to Grant a Patent dated Jun. 23, 2023, directed to JP Application No. 2021-132340; 6 pages.
European Extended Search Report dated Sep. 18, 2023, directed to EP Application No. 23174549.8; 11 pages.
Extended European Search Report dated Feb. 10, 2023, directed to EP Application No. 22187529.7; 10 pages.

(56)　　　References Cited

OTHER PUBLICATIONS

Fengler et al., U.S. Notice of Allowance and Fee(s) Due mailed Jan. 10, 2024, directed to U.S. Appl. No. 17/658,815; 7 pages.

Fengler et al., U.S. Notice of Allowance and Fee(s) Due mailed May 1, 2023, directed to U.S. Appl. No. 16/951,684; 7 pages.

Fengler et al., U.S. Office Action dated Aug. 25, 2023, directed to U.S. Appl. No. 17/658,815; 13 pages.

Fengler et al., U.S. Office Action dated Jan. 12, 2023, directed to U.S. Appl. No. 17/658,815; 14 pages.

Fengler et al., U.S. Office Action dated Sep. 14, 2022, directed to U.S. Appl. No. 16/951,684; 14 pages.

First Office Action dated Jun. 6, 2024, directed to CN Application No. 202110658728.3; 17 pages.

Intention to Grant dated Dec. 6, 2022, directed to EP Application No. 17 895 908.6.

Intention to Grant dated Mar. 18, 2024, directed to EP Application No. 16 863 277.6; 7 pages.

Intention to Grant dated May 10, 2024, directed to EP Application No. 18 178 620.3; 8 pages.

Intention to Grant dated Oct. 30, 2023, directed to EP Application No. 16 863 277.6; 8 pages.

Kim et al., (Aug. 5, 2014). "Multi-spectral imaging with infrared sensitive organic light emitting diode," Scientific Reports 4(5946): 1-5.

Moore et al., U.S. Advisory Action dated Jan. 5, 2024, directed to U.S. Appl. No. 17/493,799; 5 pages.

Moore et al., U.S. Advisory Action dated Oct. 11, 2022, directed to U.S. Appl. No. 16/933,900; 3 pages.

Moore et al., U.S. Notice of Allowance and Fee(s) due mailed Feb. 29, 2024, directed to U.S. Appl. No. 17/493,799; 5 pages.

Moore et al., U.S. Office Action dated Apr. 13, 2023, directed to U.S. Appl. No. 17/493,799; 13 pages.

Moore et al., U.S. Office Action dated Aug. 25, 2023, directed to U.S. Appl. No. 17/493,799; 5 pages.

Moore et al., U.S. Office Action dated Dec. 13, 2022, directed to U.S. Appl. No. 16/933,900; 15 pages.

Moore et al., U.S. Office Action dated Jun. 16, 2023, directed to U.S. Appl. No. 16/933,900; 14 pages.

Moore et al., U.S. Office Action dated May 16, 2022, directed to U.S. Appl. No. 16/933,900; 13 pages.

Moore et al., U.S. Office Action dated Nov. 9, 2021, directed to U.S. Appl. No. 16/933,900; 14 pages.

Moore et al., U.S. Restriction Requirement dated Jan. 10, 2023, directed to U.S. Appl. No. 17/493,799; 5 pages.

Notice of Filing Divisional Application (s) dated Oct. 27, 2023, directed to CN Application No. 202110658728.3; 4 pages.

Notice of Reasons for Refusal dated Jan. 12, 2024, directed to JP Application No. 2020-128414; 6 pages.

Notice of Reasons for Refusal dated Mar. 4, 2024, directed to JP Application No. 2023-037764; 12 pages.

Notice of Reasons for Refusal dated Sep. 9, 2022, directed to JP Application No. 2021-132340; 8 pages.

Office Action dated Dec. 1, 2022, directed to EP Application No. 16 863 277.6; 6 pages.

Office Action dated Jun. 7, 2022, directed to EP Application No. 17 812 362.6; 5 pages.

Trial and Appeal Decision dated Jun. 10, 2024, directed to JP Application No. 2020-128414; 4 pages.

Westwick et al., U.S. Notice of Allowance and Fee(s) Due mailed May 12, 2023, directed to U.S. Appl. No. 17/243,002; 7 pages.

Westwick et al., U.S. Office Action dated Nov. 16, 2022, directed to U.S. Appl. No. 17/243,002; 11 pages.

Notice of Reasons for Refusal dated Jun. 24, 2024, directed to JP Application No. 2023-118437; 20 pages.

Decision to Grant dated Apr. 28, 2023, directed to EP Application No. 17 895 908.6; 2 pages.

Decision to Grant dated Jul. 25, 2024, directed to EP Application No. 16 863 277.6; 2 pages.

Decision of Refusal dated Jan. 24, 2025, directed to JP Application No. 2023-118437; 12 pages.

Decision of Refusal dated Oct. 4, 2024, directed to JP Application No. 2023-037764; 6 pages.

Decision on Rejection dated Mar. 26, 2025, directed to CN Application No. 202110658728.3; 12 pages.

Examiner's Pre-Review Report dated Sep. 16, 2025, directed to JP Application No. 2023-118437; 8 pages.

Extended European Search Report dated Nov. 19, 2024, directed to EP Application No. 24195477.5; 11 pages.

Fengler et al., U.S. Advisory Action dated Aug. 15, 2025, directed to U.S. Appl. No. 18/662,484; 3 pages.

Fengler et al., U.S. Notice of Allowance and Fee(s) Due mailed Sep. 11, 2025, directed to U.S. Appl. No. 18/364,462; 7 pages.

Fengler et al., U.S. Office Action dated Jun. 26, 2025, directed to U.S. Appl. No. 18/662,484; 20 pages.

Fengler et al., U.S. Office Action dated Mar. 12, 2025, directed to U.S. Appl. No. 18/364,462; 21 pages.

Fengler et al., U.S. Office Action dated Oct. 23, 2025, directed to U.S. Appl. No. 18/662,484; 20 pages.

Fengler et al., U.S. Restriction Requirement dated Nov. 29, 2024, directed to U.S. Appl. No. 18/364,462; 7 pages.

Intention to Grant dated Sep. 26, 2024, directed to EP Application No. 18 178 620.3; 7 pages.

Murray et al., U.S. Notice of Allowance and Fee(s) due mailed Jul. 3, 2025, directed to U.S. Appl. No. 18/761,256; 5 pages.

Murray et al., U.S. Office Action dated Mar. 12, 2025, directed to U.S. Appl. No. 18/761,256; 12 pages.

Office Action dated Apr. 24, 2025, directed to EP Application No. 17 812 362.6; 3 pages.

Office Action dated Feb. 28, 2025, directed to EP Application No. 22 187 529.7 ; 4 pages.

Office Action dated May 21, 2025, directed to EP Application No. 23174549.8; 5 pages.

Second Office Action dated Oct. 28, 2024, directed to CN Application No. 202110658728.3; 13 pages.

U.S. Office Action mailed Dec. 30, 2024, directed to U.S. Appl. No. 18/662,484; 19 pages.

Westwick et al., U.S. Office Action dated May 18, 2022, directed to U.S. Appl. No. 17/243,002; 13 pages.

Notice of Reasons for Refusal dated Mar. 6, 2026, directed to JP Application No. 2025-016251; 10 pages.

Fengler et al., U.S. Notice of Allowance and Fee(s) Due mailed Mar. 4, 2026, directed to U.S. Appl. No. 18/662,484; 7 pages.

Office Action dated Mar. 19, 2026, directed to EP Application No. 22 187 529.7; 8 pages.

Intention to Grant dated Mar. 6, 2026, directed to EP Application No. 23174549.8; 8 pages.

* cited by examiner

$$11 \begin{cases} 20 \begin{cases} 20a \\ 20b \end{cases} \\ 21 \\ 22 \end{cases}$$

$$13 \begin{cases} 51 \\ 52 \\ 53 \end{cases}$$

SYSTEMS AND METHODS FOR ILLUMINATION AND IMAGING OF A TARGET

CROSS-REFERENCE TO RELATED APPLICATIONS

This application is a continuation of U.S. patent application Ser. No. 16/933,900, filed Jul. 20, 2020, which is a continuation of U.S. patent application Ser. No. 16/441,493, filed Jun. 14, 2019, now U.S. Pat. No. 10,721,410, which is a divisional of U.S. patent application Ser. No. 15/348,664, filed Nov. 10, 2016, now U.S. Pat. No. 10,356,334, which claims the benefit of U.S. Provisional Application No. 62/255,024, filed Nov. 13, 2015, the entire contents of each of which are incorporated by reference herein.

TECHNICAL FIELD

The present disclosure relates generally to the field of illumination and imaging. More specifically, the disclosure relates to illumination and imaging of a target material.

BACKGROUND

Illumination is an important component of imaging systems such as, for example, broadband imaging systems with self-contained illumination. In many applications of imaging systems, such as in medical imaging, it may be challenging to achieve even, full field illumination of the imaging field of view, and also to provide a sufficient intensity of illumination to yield a sufficiently strong imaging signal. Conforming the illumination profile to match the imaging field of view is one method of conserving illumination power, while multiple illumination ports may be used to provide even illumination across the field of view. Conventional illumination projection in imaging systems may feature anamorphic projection to match the imaging field of view, but typically only feature a single illumination port and are not configured for close working distances. Single port illumination systems result in substantial shadowed regions obscuring vision when illuminating complex topography such as, for example, human anatomical structures or other biological materials. Existing designs for field surgical imaging and illumination devices may make use of multiple illumination ports to minimize shadowed regions, such as a ring light surrounding the imaging optics, but these designs waste excess illumination outside of the field of view and fail to achieve even illumination of the field of view over a range of working distances.

SUMMARY

One or more embodiments are directed to an illumination module for use in an imaging system having an imaging field of view for imaging a target, the illumination module including a first illumination port to output a first light beam having a first illumination distribution at the target to illuminate the target and a second illumination port to output a second light beam having a second illumination distribution at the target to illuminate the target. The second illumination distribution may be substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view.

Light from the first and second illumination ports may respectively overlap to provide uniform illumination over a target field of view.

The illumination module may include a steering driver to simultaneously steer the first and second illumination ports through different fields of view.

Each of the first and second illumination ports may include a lens module having at least one fixed lens, a steerable housing, and at least one lens mounted in the steerable housing, the steerable housing being in communication with the steering driver.

The illumination module may include an enclosure, the enclosure housing the first and second illumination ports and the steering driver.

The enclosure may be a hand held enclosure and may include a control surface including activation devices to control the steering driver.

Each of the first and second illumination distributions may be a rectangular illumination distribution.

Each of the first and second illumination ports may include a lens module having two pairs of cylindrical lenses.

The first and second illumination ports may be symmetrically offset from a long dimension midline of the rectangular illumination distribution.

One or more embodiments are directed to an imaging device having an imaging field of view, the imaging device including a first illumination port to output first light having a first illumination distribution at a target to illuminate the target, a second illumination port to output second light having a second illumination distribution at the target to illuminate the target, the second illumination distribution being substantially similar to the first illumination distribution at the target, the second illumination port being spaced apart from the first illumination port, the first and second illumination distributions being simultaneously provided to the target and overlapping at the target, wherein the illumination from the first and second ports is matched to a same aspect ratio and field of view coverage as the imaging field of view, and a sensor to detect light from the target.

The imaging device may include an enclosure, the enclosure housing the first and second illumination ports, and the sensor.

The imaging device may include a steering driver to simultaneously steer the first and second illumination ports through different fields of view.

The imaging device may include an imaging element to focus light onto the sensor, wherein the steering driver is to move the imaging element in synchrony with steering of the first and second illumination ports.

The steering driver may be in the enclosure and the enclosure may include a control surface including activation devices to control the steering driver.

The enclosure may have a hand held enclosure having a form factor that allows a single hand to control the control surface and illumination of the target from multiple orientations.

The imaging device may include an illumination source to output light to the first and second illumination ports, the illumination source being outside the enclosure.

The illumination source may output visible light and/or excitation light to the first and second illumination ports.

The sensor may be a single sensor that is to detect light from the target resulting from illumination by visible light and excitation light.

The imaging device may include a wavelength-dependent aperture upstream of the sensor, the wavelength-dependent aperture to block visible light outside a central region.

The imaging device may include a video processor box, the video processor box being outside the enclosure.

The illumination source may be integral with the video processor box.

One or more embodiments are directed to a method of examining a target, the method including simultaneously illuminating the target with a first light output having a first illumination distribution at the target and with a second light output having a second illumination distribution at the target, the second illumination distribution being substantially similar to the first illumination distribution, the first and second illumination distributions overlapping at the target, wherein the illumination on the target is matched to the same aspect ratio and field of view coverage as an imaging field of view.

The method may include simultaneously steering the first and second light outputs through different fields of view.

The method may include receiving light from the target and focusing light onto a sensor using an imaging element, the imaging element being moved in synchrony with simultaneous steering of the first and second light outputs.

One or more embodiments are directed to a drape for use with an imaging device, the drape including a barrier material enveloping the imaging device, a drape window frame defining an opening in the barrier material, a drape lens in the opening in the barrier material, and an interface integral with the drape window frame to secure the drape lens to a window frame of the imaging device.

The drape may be insertable into the window frame of the imaging device.

The interface may include two clamps integrated symmetrically on respective opposing sides of the drape window frame.

The two clamps are on a top and a bottom of the drape window frame.

One or more embodiments are directed to a processor to image a target, the processor to, within a period, turn on an excitation light source to generate an excitation pulse to illuminate the target, turn on a white light source to generate a white pulse to illuminate the target such that the white pulse does not overlap the excitation pulse and the white pulse is generated at least twice within the period, expose an image sensor for a fluorescent exposure time during the excitation pulse, expose the image sensor for a visible exposure time during at least one white pulse, detect outputs from the image sensor, compensate for ambient light, and output a resultant image.

To compensate for ambient light, the processor may expose a first set of sensor pixel rows of the image sensor for a fraction of the fluorescent exposure time for a first set of sensor pixel rows; and expose a second set of sensor pixel rows of the image sensor for all of the fluorescent exposure time, the first and second sets to detect at least one different color from the other.

The fraction may be ½.

The processor may determine the fluorescent signal F using the following equation:

$$F=2*Exp2-Exp1,$$

where Exp1 is a signal output during the fraction of fluorescent exposure time and Exp2 is a signal output during all of the fluorescent exposure time.

The fraction of the exposure time may equal a width of the excitation pulse.

The visible exposure time may be longer than a width of the at least one white pulse.

The visible exposure time may be for one white pulse within the period.

The visible exposure time may be for two white pulses within the period.

To compensate for ambient light, the processor may expose the image sensor for background exposure time when target is not illuminated at least once within the period.

One or more embodiments are directed a method for imaging a target, within a period, the method including generating an excitation pulse to illuminate the target, generating a white pulse to illuminate the target such that the white pulse does not overlap the excitation pulse and the white pulse is generated at least twice within the period, exposing an image sensor for a fluorescent exposure time during the excitation pulse, exposing the image sensor for a visible exposure time during at least one white pulse, detecting outputs from the image sensor, compensating for ambient light, and outputting a resultant image.

Compensating for ambient light may include exposing a first set of sensor pixel rows of the image sensor for a fraction of the fluorescent exposure time and exposing a second set of sensor pixel rows of the image sensor for all of the fluorescent exposure time, the first and second sets to detect at least one different color from the other.

Compensating for ambient light may include exposing the image sensor for a background exposure time when target is not illuminated at least once within the period.

Generating the excitation pulse may include providing uniform, anamorphic illumination to the target.

Providing uniform, anamorphic illumination to the target includes overlapping illumination from at least two illumination ports.

One or more embodiments are directed to a method of displaying fluorescence intensity in an image, the method including displaying a target reticle covering a region of the image, calculating a normalized fluorescence intensity within the target reticle, and displaying the normalized fluorescence intensity in a display region associated with the target.

The display region may be projected onto the target.

The normalized fluorescence intensity may include a single numerical value and/or a historical plot of normalized fluorescence intensities.

One or more embodiments are directed to a kit, including an illumination module including at least two illumination ports spaced apart from one another, first and second illumination distributions to being simultaneously provided to a target and to overlap at the target, and an imaging module including a sensor to detect light from the target.

The kit may include an enclosure to enclose the illumination module and the imaging module.

One or more embodiments are directed to a fluorescence imaging agent for use in the imaging device and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

BRIEF DESCRIPTION OF THE DRAWINGS

The patent or application file contains at least one drawing executed in color. Copies of this patent or patent application publication with color drawings(s) will be provided by the Office upon request and payment of the necessary fee.

Features will become apparent to those of ordinary skill in the art by describing in detail exemplary embodiments with reference to the attached drawings in which:

FIGS. 3A and 3B illustrate schematic side view and plan view, respectively, of an exemplary lens module in a steerable housing according to an embodiment;

FIG. 15 illustrates an exemplary light source of an exemplary illumination source of the system for illumination shown in FIG. 1.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Figure 1:
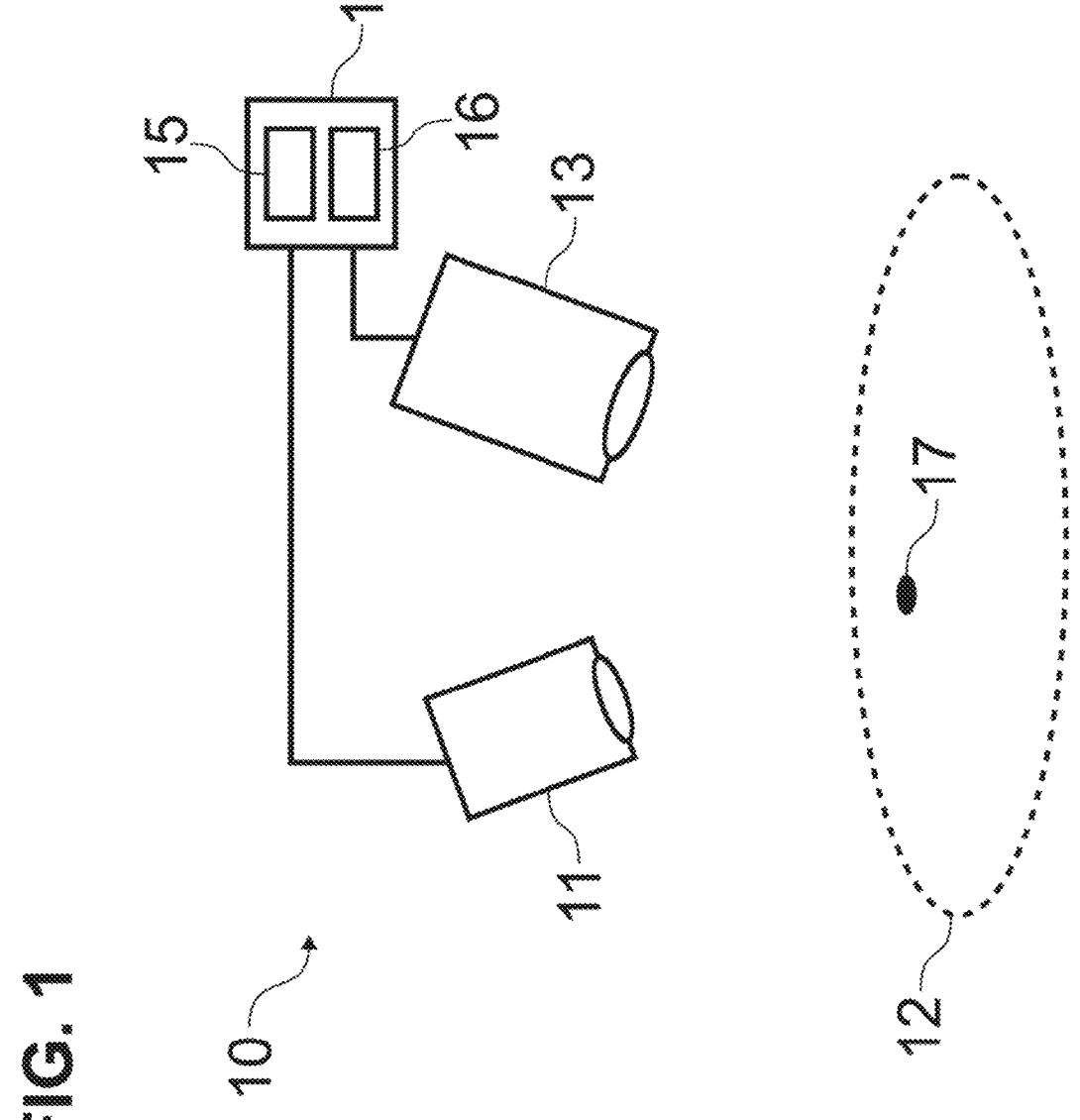
FIG. 1 illustrates a schematic view of a system for illumination and imaging according to an embodiment.

FIG. 1 illustrates a schematic view of an illumination and imaging system 10 according to an embodiment. As may be seen therein, the system 10 may include an illumination module 11, an imaging module 13, and a video processor/illuminator (VPI) 14. The VPI 14 may include an illumination source 15 to provide illumination to the illumination module 11 and a processor assembly 16 to send control signals and to receive data about light detected by the imaging module 13 from a target 12 illuminated by light output by the illumination module 11. The illumination source 15 may output light at different waveband regions, e.g., white (RGB) light, excitation light to induce fluorescence in the target 12, and so forth, depending on characteristics to be examined and the material of the target 12. Light at different wavebands may be output by the illumination source simultaneously or sequentially. The illumination and imaging system 10 may be used, for example, to facilitate a surgical procedure. The target 12 may be a topographically complex target, e.g., a biological material including tissue, an anatomical structure, other objects with contours and shapes resulting in shadowing when illuminated, and so forth. The VPI 14 may record, process, display, and so forth, the resulting images and associated information.

Figure 2:
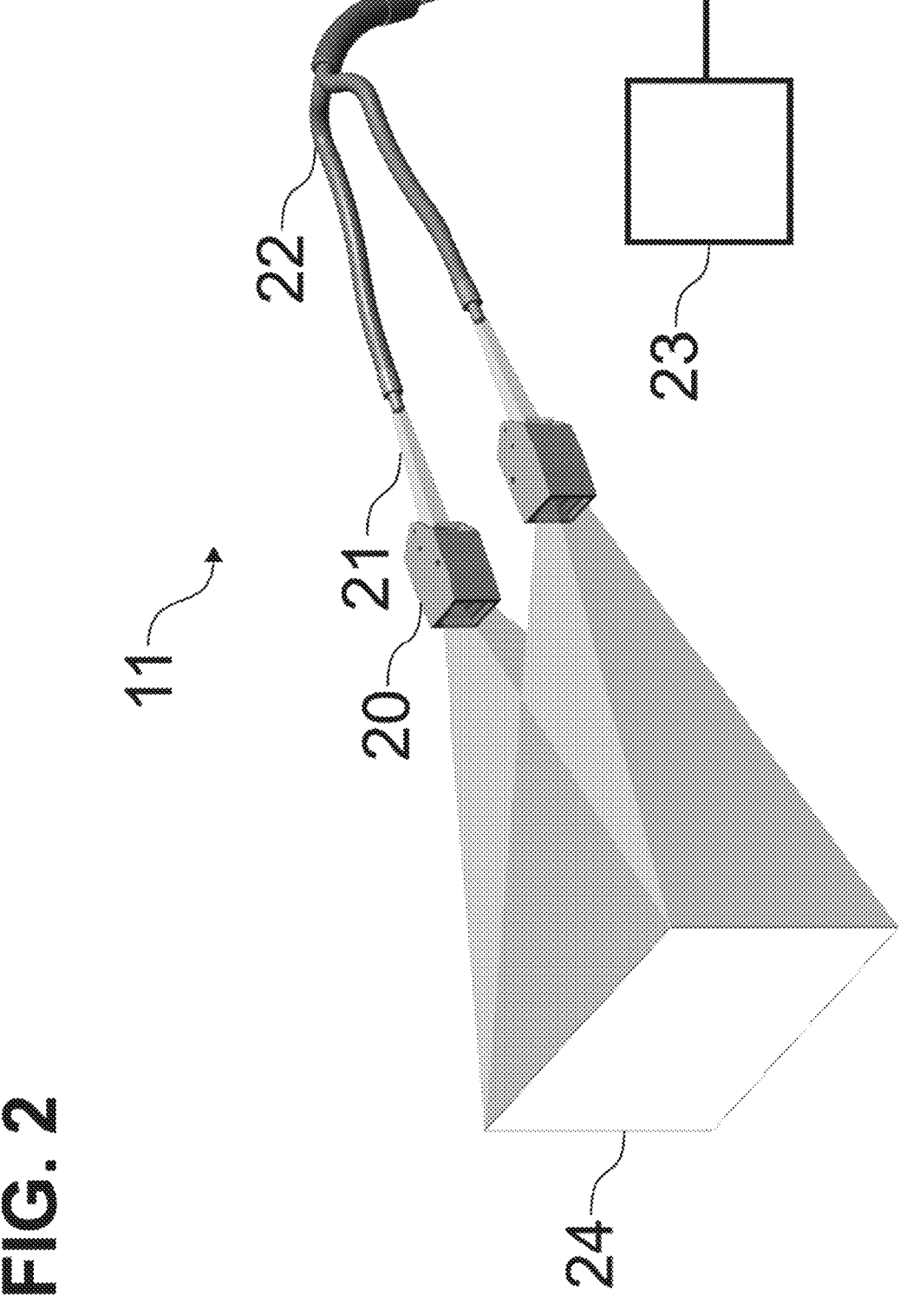
FIG. 2 illustrates a schematic view of an illumination module according to an embodiment.

FIG. 2 illustrates a schematic perspective view of the illumination module 11 of FIG. 1 according to an embodiment. As may be seen therein, the illumination module 11 may include at least two illumination ports directing illumination from an illumination source 23, which may be included in the VPI box 14, to for example a rectangular target field 24. Each illumination port is to provide illumination over the target field 24, such that the light overlaps, e.g., substantially or completely, at the target material 12 (shown in FIG. 1). More than two illumination ports may be used. The illumination distributions are substantially similar and substantially overlap at the target 12 to provide uniform illumination of the target 12. The use of at least two illumination ports reduces the effect of shadowing due to anatomical topography, and aids in providing uniform illumination over the target field 24. Directing illumination from the illumination module 11 to a rectangular target field 24 allows matching the region of illumination to a rectangular imaging field of view, which aids in providing uniform illumination and enhances efficiency of the illumination module by reducing extraneous illumination. Matching the illumination field to the imaging field of view also provides a useful indication of the location and extent of the anatomical region currently being imaged.

In some embodiments, a light pipe may be used to achieve mixing of the illumination light in order to yield a uniform illumination profile. Mixing of the illumination light by a light pipe may remove the influence of the structure of the light source on the illumination profile, which could otherwise adversely affect uniformity of the illumination profile. For example, using a light pipe to mix the illumination light output from a fiber optic light guide may remove images of the structure of the individual optical fibers from the illumination profile. In some embodiments, a rectangular light pipe may be used to conserve illumination power while matching the illumination profile to a rectangular imaging field of view. In some embodiments, a light pipe material with a high index of refraction for both visible light and near infrared light, such as optical glass material N-SF11, may be used for high efficiency of illumination power transmission.

According to some embodiments, a rectangular light pipe with an aspect ratio matching the aspect ratio of the imaging field of view (e.g., both aspect ratios being 16:9) may be used in conjunction with rotationally symmetric illumination optic elements.

According to some embodiments, a rectangular light pipe with a different aspect ratio than the imaging field of view (e.g., a square light pipe along with a 16:9 imaging field of view aspect ratio) may be used in conjunction with cylindrical illumination optic elements. Cylindrical optic elements may be used to separately conform one or both dimensions of the rectangular illumination profile to match the aspect ratio of the imaging field of view.

Depending on the desired system requirements for range of working distance and illumination uniformity various approaches may be used for matching the illumination to a rectangular imaging field of view. For example, applications with high requirements for range working distance and illumination uniformity may necessitate use of illumination optics that are steered dynamically to adequately match the illumination to the imaging field of view, while applications with lower requirements may be served with fixed illumination optics to match the illumination to the field of view.

In some embodiments, one or more illumination optic elements may be rotated by a driver in order to steer the illumination.

In some embodiments, one or more illumination optic elements may be translated perpendicular to the imaging optic axis by a driver in order to steer the illumination.

In some embodiments, one or more illumination optic elements may be configured to provide some distortion in the illumination profile, in order to account for distortion inherent to the accompanying imaging system.

In some embodiments, uniform illumination of the imaging field of view over a specified range of working distances may be achieved with a fixed location and orientation of the illumination optics. The offset distance of the illumination optics from the imaging optic axis may be configured, along with the orientation of the of the illumination optics, in order to optimize matching of the illumination profile to the imaging field of view at a working distance within the specified range of working distances while also maintaining substantial matching of the illumination profile to the imaging field of view at other working distances within the specified range.

As is illustrated in FIG. 2, each illumination port may include a lens module 20, a connecting cable 22 connected to the illumination light source 23, and a light pipe 21 adapting a high numerical aperture of the connecting cable 22 to a lower numerical aperture of the lens module 20. The lens module 20 may be steerable, as described in detail below. In some scenarios, acceptable performance may be achievable without steering. In other words, an illumination module, and imaging device having the same, that provides a illumination having a rectangular form factor that matches the field of view of the imaging system using at least two illumination ports in which each port produces a gradient of illumination such that the sum illumination flux in the object plane is reasonably the same at each point in the illumination field, e.g., provides uniform illumination over the imaging field of view, alone may be sufficient.

Figure 3A:
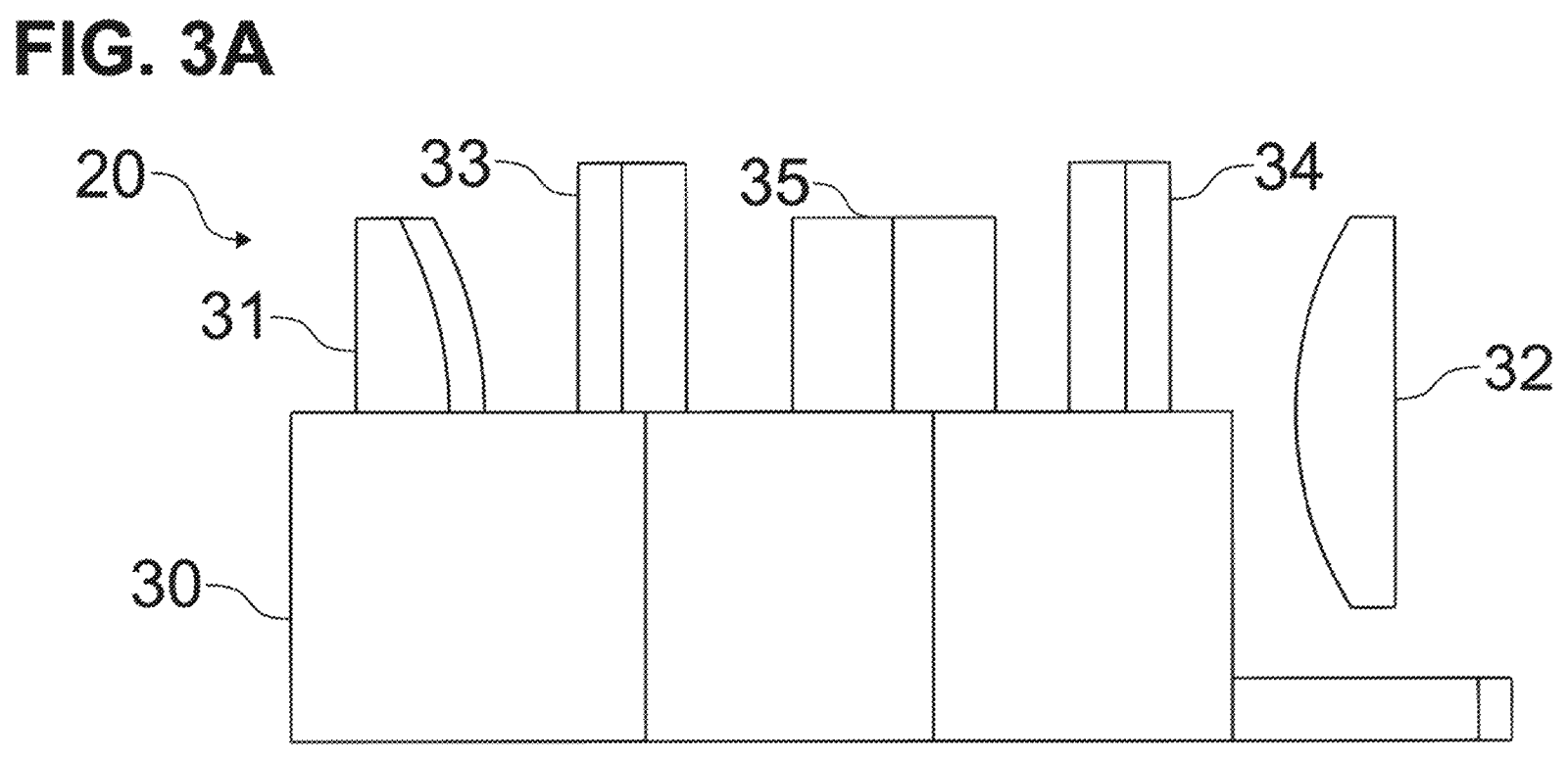
Figure 3B:
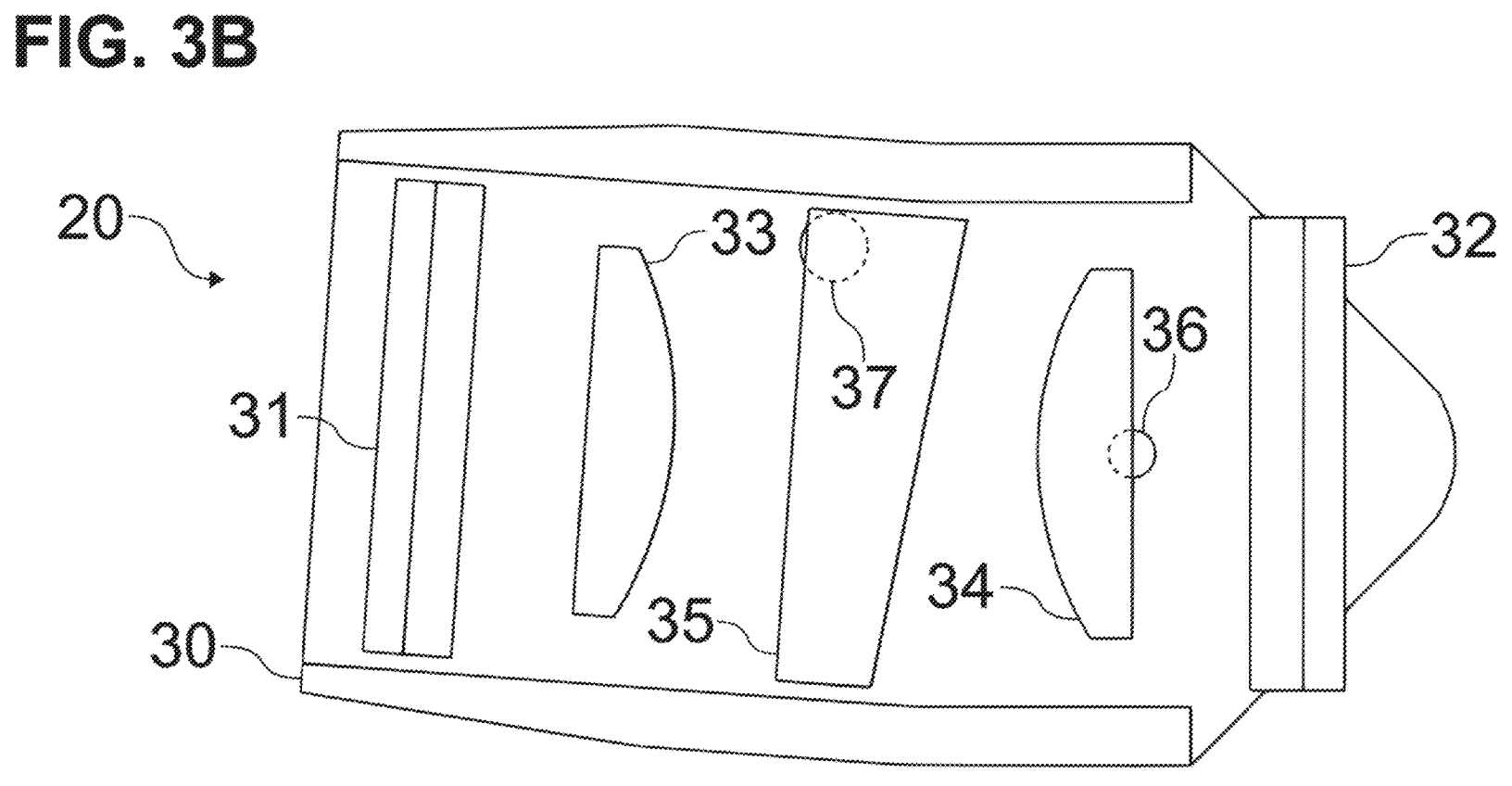

FIGS. 3A and 3B illustrate a side view and a plan view, respectively, of the lens module 20. The lens module 20 may include lenses mounted in a steerable lens housing 30. As used herein, a lens is any optical element having optical power, whether implemented by a refractive or diffractive element. Other elements not essential to understanding, such as a cover enclosing the lens module (see FIG. 2), are not shown for ease of illustration.

In the particular example shown herein, the lenses may include a pair of horizontal-axis cylindrical lenses 31-32 and a pair of vertical-axis cylindrical lenses 33-34. A prism element 35 is also shown which may align illumination light with the intended outgoing optical axis. In particular, the prism element 35 corrects for an angle introduced by the light pipe 21 for increased device compactness in accordance with an embodiment. The mounting design for each lens element 31-35 may allow for tuning of the magnification and focus of the illumination optical system. In accordance with this embodiment, the steerable lens housing 30 encloses and steers three of the cylindrical lenses 31, 33, 34 and the prism lens element 35, e.g., collectively as a group. This example of lenses is merely illustrative, and the lenses in the lens module 20 may be modified as appropriate.

In this particular embodiment, a base portion of the steerable housing 30 is pinned, e.g., using a pin 46 (see FIG. 6B) inserted into housing hole 37, about a pivot point 36, respectively to a fixed chassis frame 90 (see FIG. 6A) and a mechanical linkage 40 (see FIGS. 4A to 4C) described in detail below, while lens 32 is rigidly connected the chassis 90, i.e. not to the housing 30 (see FIG. 6B).

Figure 4A:
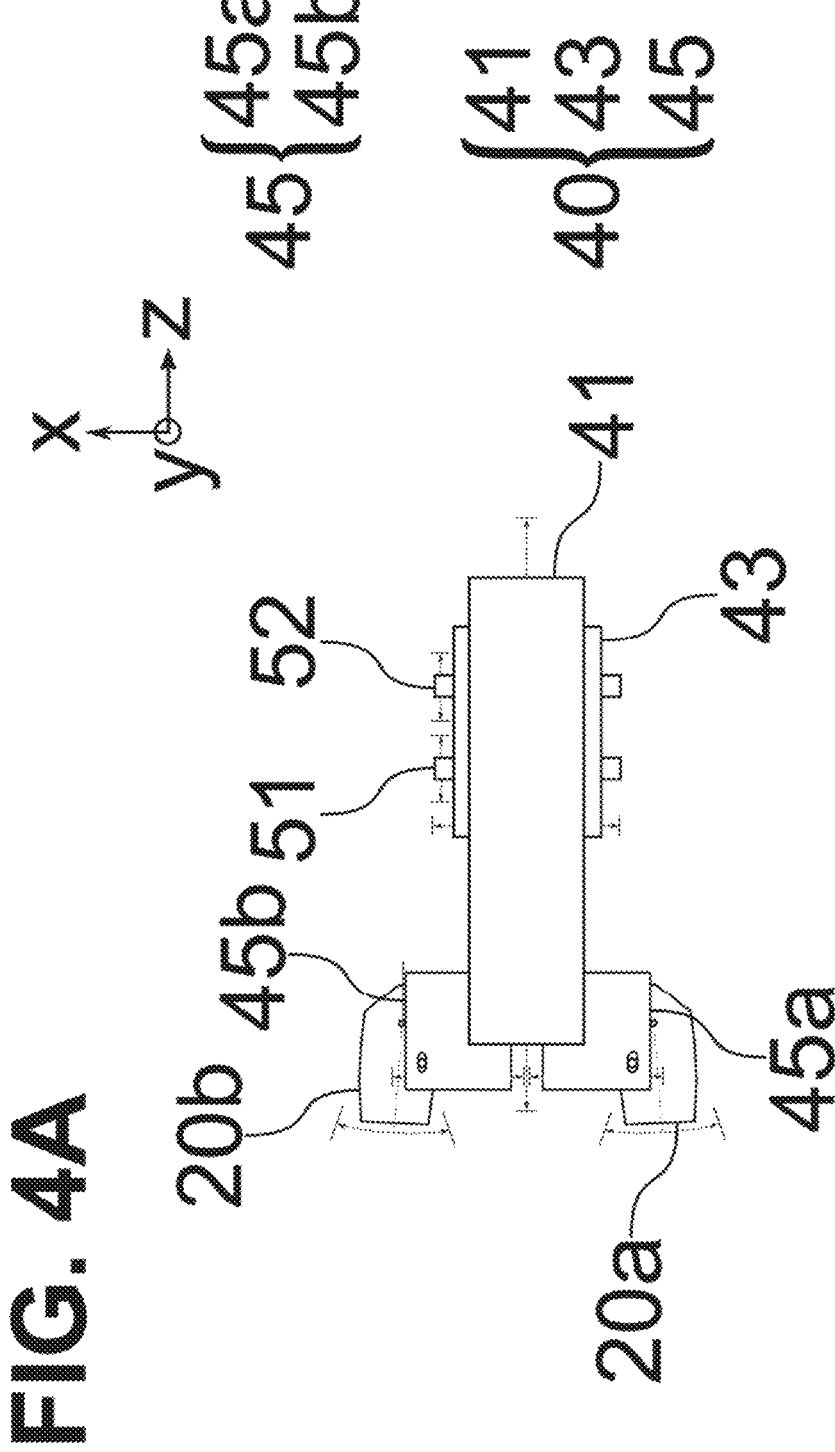
FIG. 4A illustrates a schematic view of a linkage for synchronous focusing of the imaging system and steering of the illumination system according to embodiments.

FIG. 4A illustrates a schematic view showing directions of motion provided by various components of the linkage 40. The linkage 40 may include a drive cam 41, illumination cams 45a, 45b (one for each illumination port), and an imaging cam 43. The drive cam 41 receives an input from a user (see FIG. 6), and translates that to synchronous motion of the lens module 20a, 20b, attached to a corresponding illumination cam 45a, 45b, via a respective housing 30 and a pin 46, and an imaging lens 51 and an imaging sensor 52 (see FIGS. 5A and 5B), attached to the imaging cam 43 via cam follower pins. Here, the imaging lens 51 is shown as a single field lens, but additional and/or alternative lenses for focusing light from the target 20 onto the imaging sensor 52 may be employed. Each port has its own associated illumination cam 45A and 45B, here shown as being to a left and right of an input window to receive light from the target 12.

In particular, translation of the drive cam 41 may translate the imaging cam 43 along the x-axis, which, in turn, may result in the imaging cam 43 to translate the imaging lens 51 and the imaging sensor 52 along the z-axis, as well as translate the illumination cams 45a, 45b, which, in turn, simultaneously steer corresponding lens modules 20a, 20b about respective pivot points 36, such that steering of the lens modules 20a, 20b is synchronously performed with the position adjustment of the imaging lens 51 and the imaging sensor 52 to insure proper focus of light from the target onto the sensor 52. Alternatively, the imaging cam 43 may translate only the imaging lens 51 along the z-axis, or any other combination of imaging optical elements in order to insure proper focus of light from the target onto the sensor 52.

Figure 4B:
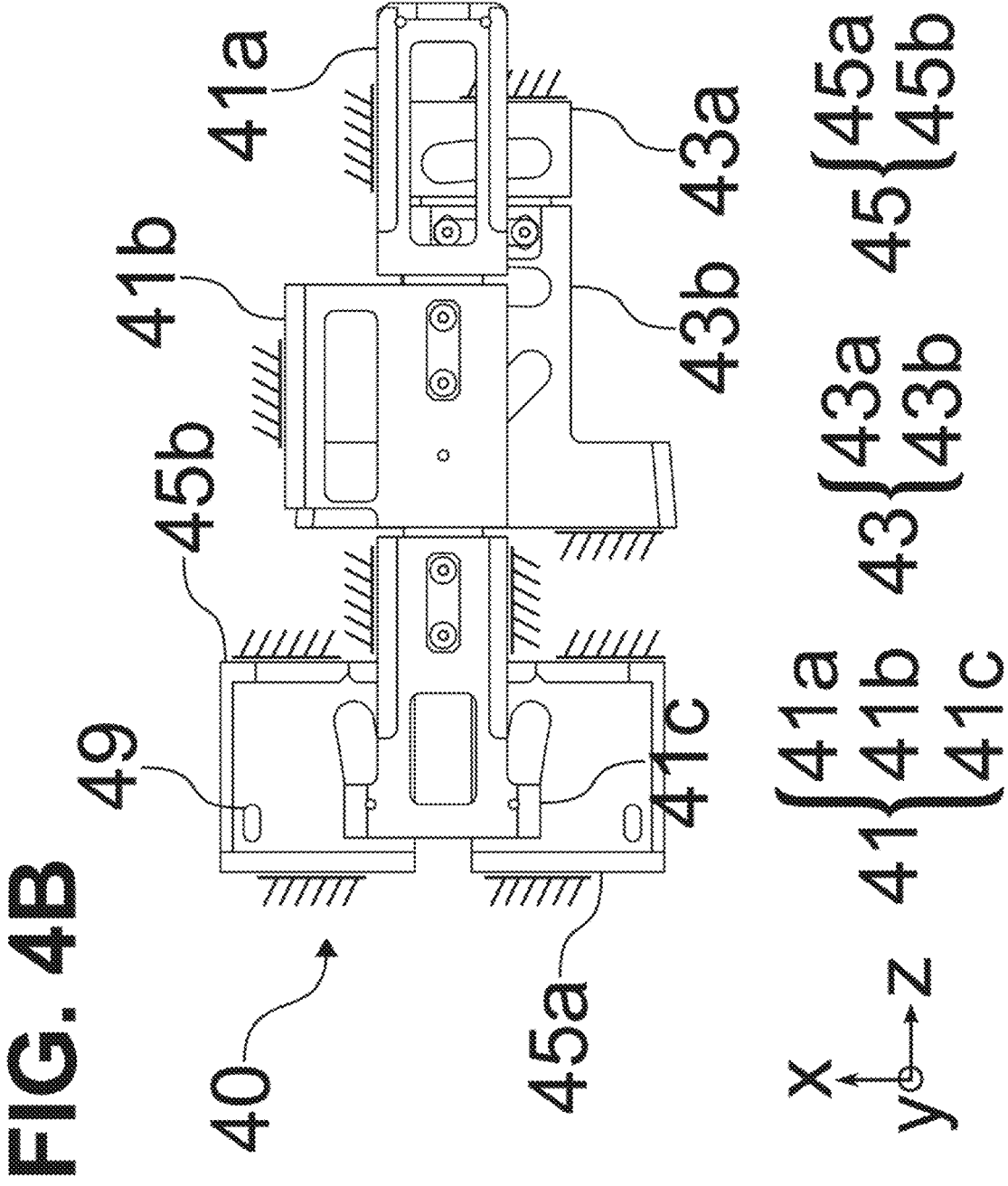
FIGS. 4B and 4C illustrate a bottom view and a top view, respectively, of a linkage for synchronous focusing of the imaging system and steering of the illumination system according to embodiments.
Figure 4C:
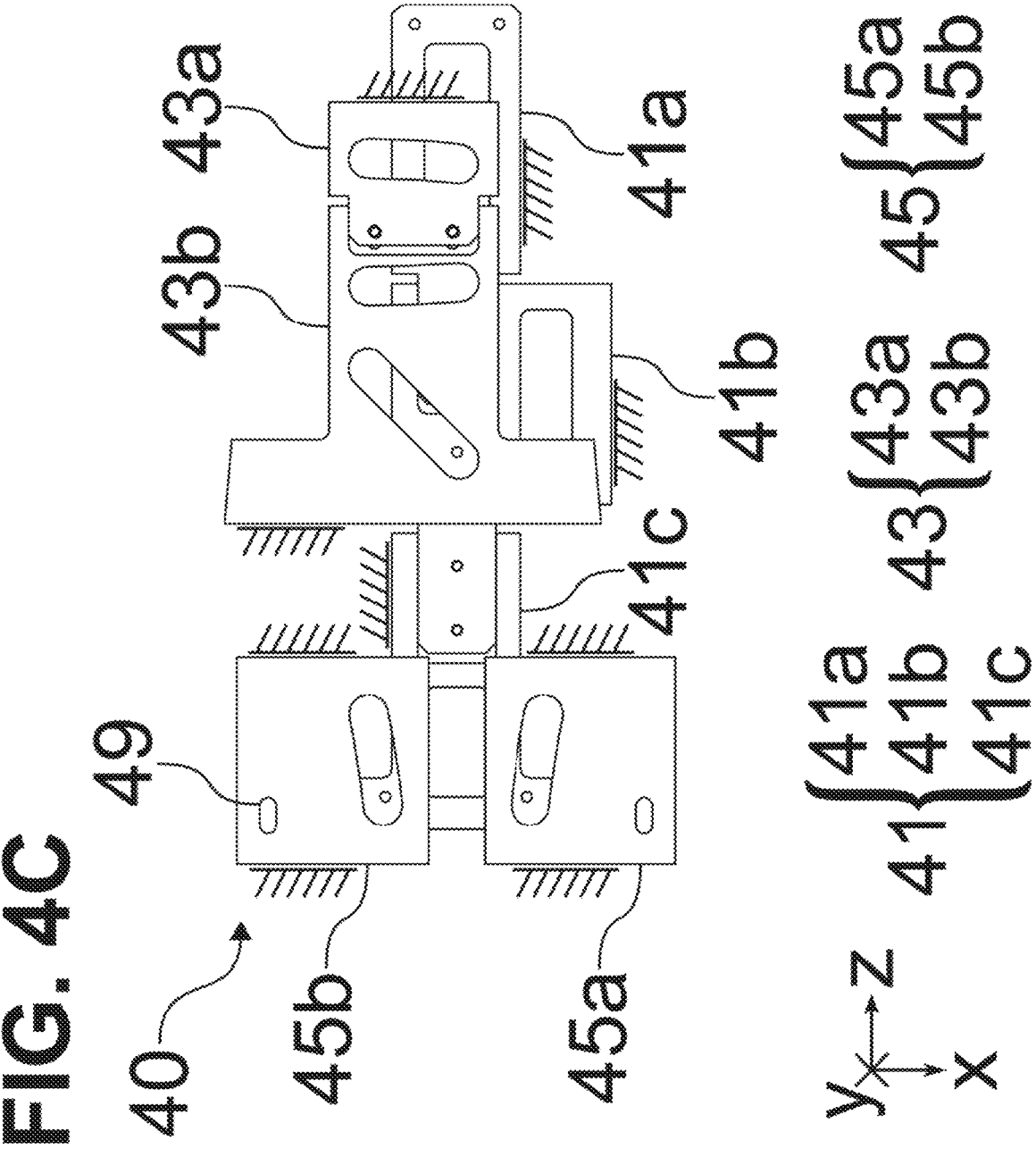

FIG. 4B illustrates a bottom view and FIG. 4C illustrates a top view of the linkage 40 according to an embodiment. The drive cam 41 may include two drive parts 41a and 41b, and, if steering is included, a third drive part 41c, all of which are shown here as being rigidly attached to form a rigid drive cam 41. Similarly, the imaging cam 43 may include two imaging parts 43a and 43b. The drive cam 41 receives the input from a user (via control surface 62) via the first drive part 41a and translates the imaging cam 43 via a cam follower pin in drive part 41b, resulting in the imaging cam part 43a translating the sensor 52 and the imaging cam part 43b translating the imaging lens 51. If steering is included in the linkage, the third drive part 41c simultaneously steers (rotates) the lens modules 20a, 20b using the pin 46 (see FIG. 6B) associated with each of the illumination cam parts 45a and 45b, by translating the illumination cam parts 45a and 45b. The pin 46 may be inserted through a through a slot 49 in each of the illumination cams 45a, 45b and the corresponding housing hole 37 in the lens modules 20a, 20b. The drive part 41c steers the lens modules 20a, 20b simultaneously such that they both still illuminate a same field of view as one another at the target field of view of the target 12.

Figure 5A:
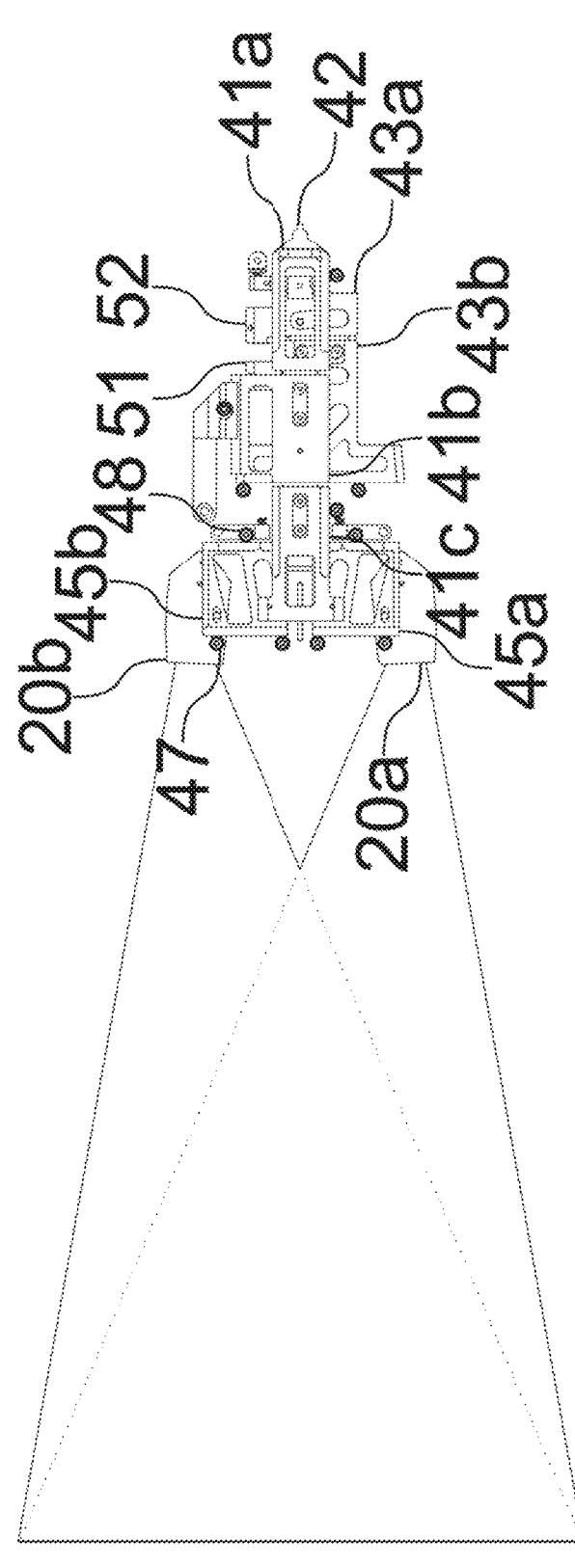
FIGS. 5A and 5B illustrate bottom views of the linkage at a far working distance and a near working distance, respectively, according to an embodiment.
Figure 5B:
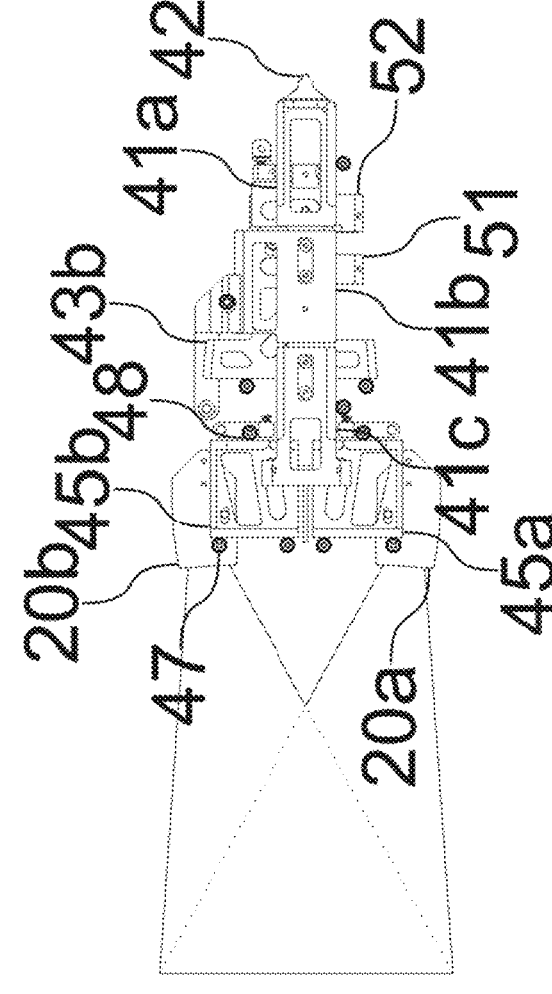

FIGS. 5A and 5B illustrate bottom views of the linkage combined with the lens modules 20a, 20b, the imaging field lens 51, and the sensor 52, at a far working distance and a near working distance, respectively, according to an embodiment. As can be seen therein, the linkage 40 synchronizes steering of the illumination sources with focusing of the imaging system at two sample working distance illumination steering settings. FIGS. 5A-5B show the positions of lens modules 20a, 20b (rotated about the pivot pint 37) and the lens 51 and sensor 52 (translated along an optical axis 55 of the imaging system and along the x-axis) at two focus positions resulting from user input.

As illustrated in FIGS. 5A and 5B, each part that moves axially within the linkage mechanism 40 may be guided by two fixed rolling elements 47, and one spring-loaded rolling element 48, in order to reduce or minimize friction during motion. The linkage 40 also may include a drive cam input connection point 42.

Figure 6A:
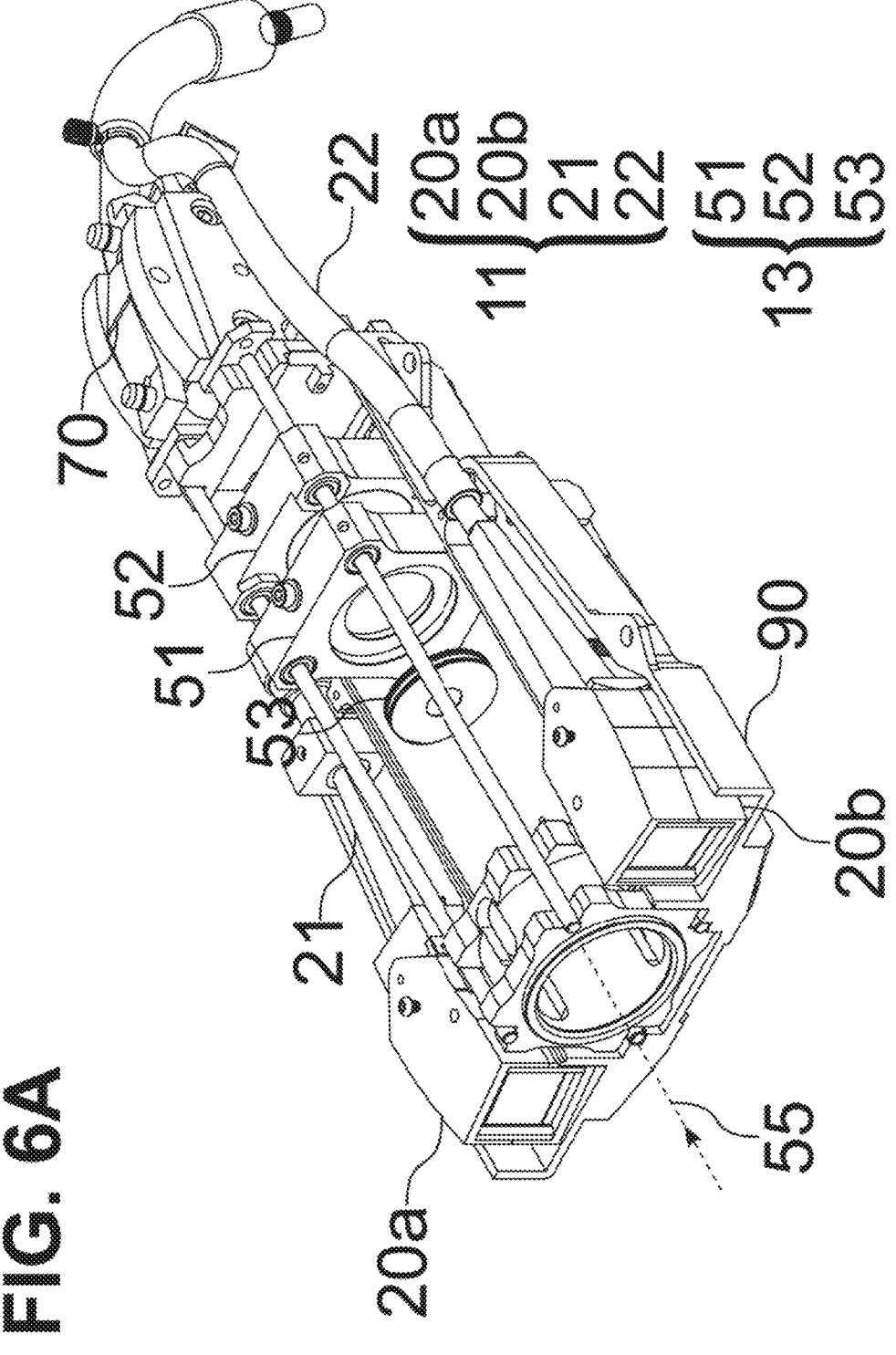
FIGS. 6A and 6B illustrate a perspective top view and a perspective bottom view of an illumination and imaging system according to an embodiment.
Figure 6B:
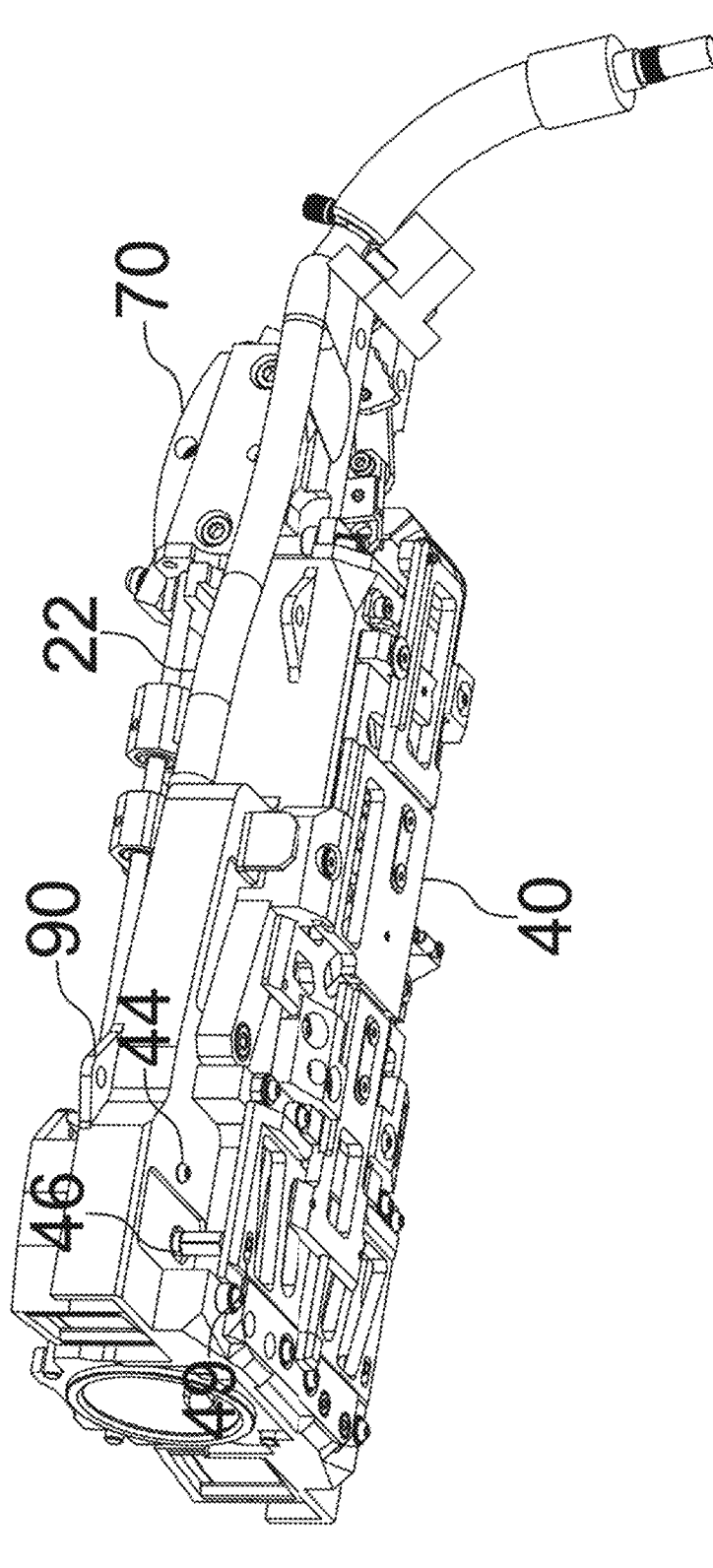

FIGS. 6A and 6B illustrate a perspective top view and a perspective bottom top view of the device 10 in accordance with an embodiment. In FIGS. 6A and 6B, the illumination module 11 and the imaging module 13 are mounted on the chassis 90, the top portion of which is removed in for clarity. Also, a focus actuation mechanism 70 is illustrated, which translates motion from user input to motion of the drive cam 41 via the drive cam input connection point 42.

As can be seen in FIG. 6A, an optical axis 55 of the imaging module 13 runs through a center of the imaging module, with the lens modules 20a, 20b being arranged symmetrically relative to the imaging optical axis 55. The light to be imaged from the target 12 travels along the optical axis 55 to be incident on the lens 51 and sensor 52. A wavelength-dependent aperture 53 that includes a smaller central aperture that permits transmission of all visible and fluoresced light, e.g., near infrared (NIR) light, and a surrounding larger aperture that blocks visible light but permits transmission of fluoresced light, may be provided upstream of the lens 51.

Referring to FIGS. 6B and 4A-4B, the pin 46 connects the lens module 20, via the housing hole 37 in the housing 30, slot 49 of the linkage 40. Also, a pivot point pin 44 connects the lens module 20 to the chassis 90.

Figure 7:
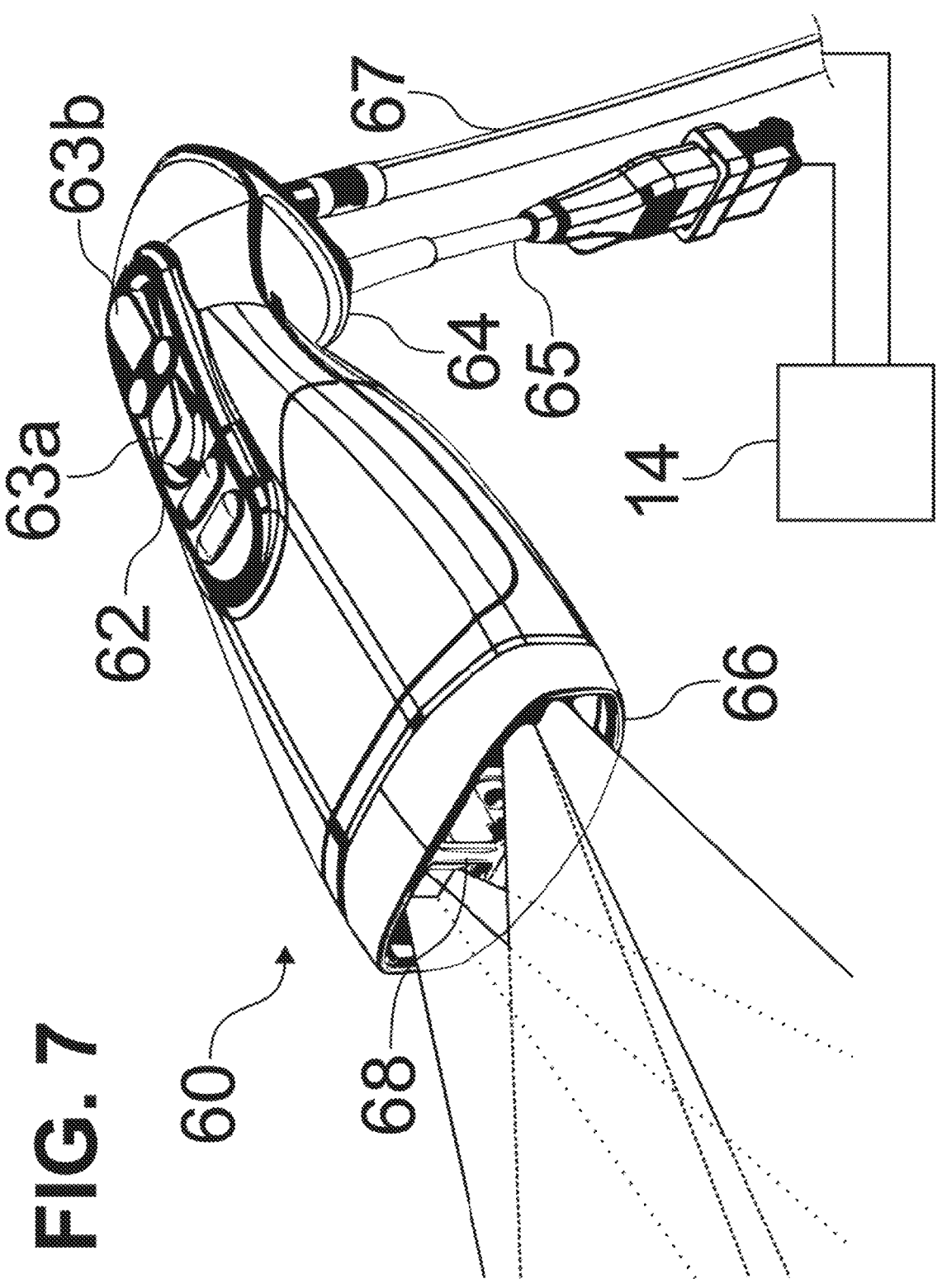
FIG. 7 illustrates an enclosure according to an embodiment.

FIG. 7 illustrates an embodiment of an ergonomic enclosure 60 enclosing the illumination module 11 and the imaging module 13. The ergonomic enclosure 60 is designed to be held in different use-modes/configurations, for example, a pistol-style grip for forward imaging in a scanning-imaging orientation (FIG. 8A), and a vertical-orientation grip for use when imaging downward in an overhead imaging orientation (FIG. 8B). As may be seen in FIG. 7, the enclosure 60 includes a control surface 62, a grip detail 64, a window frame 68 and a nosepiece 66. The ergonomic enclosure 60 is connectable to the VPI box 14 via a light guide cable 67, through which the light is provided to the illumination ports 20a, 20b, and a data cable 65 that transmits power, sensor data, and any other (non-light) connections.

The control surface 62 includes focus buttons 63a (decreasing the working distance) and 63b (increasing the working distance) that control the linkage 40. Other buttons on the control surface 62 may be programmable and may be used for various other functions, e.g., excitation laser power on/off, display mode selection, white light imaging white balance, saving a screenshot, and so forth. Alternatively or additionally to the focus buttons, a proximity sensor may be provided on the enclosure and may be employed to automatically adjust the linkage 40.

Figure 8A:
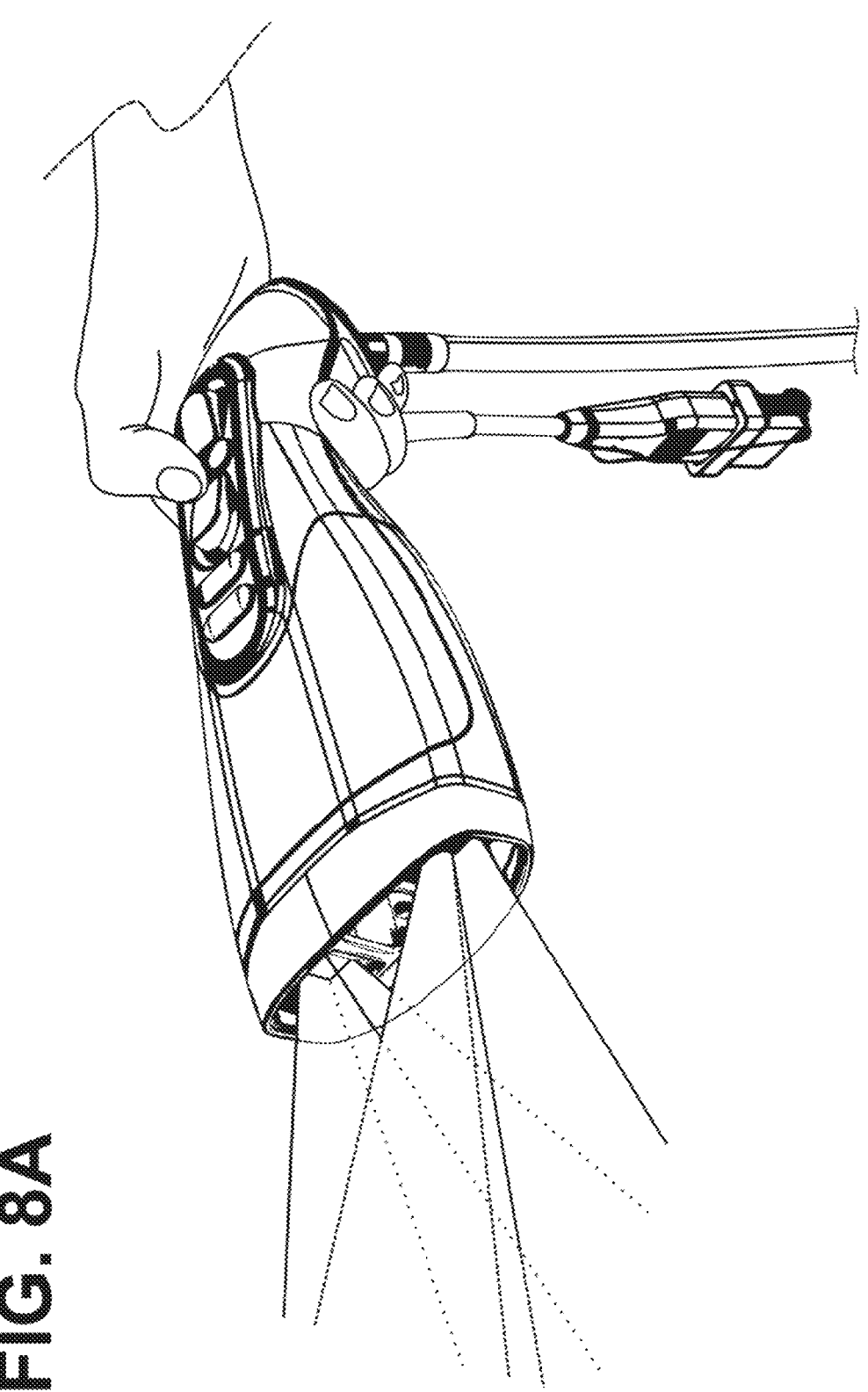
FIGS. 8A and 8B illustrate perspective views of different exemplary positions in which the system may be used.
Figure 8B:
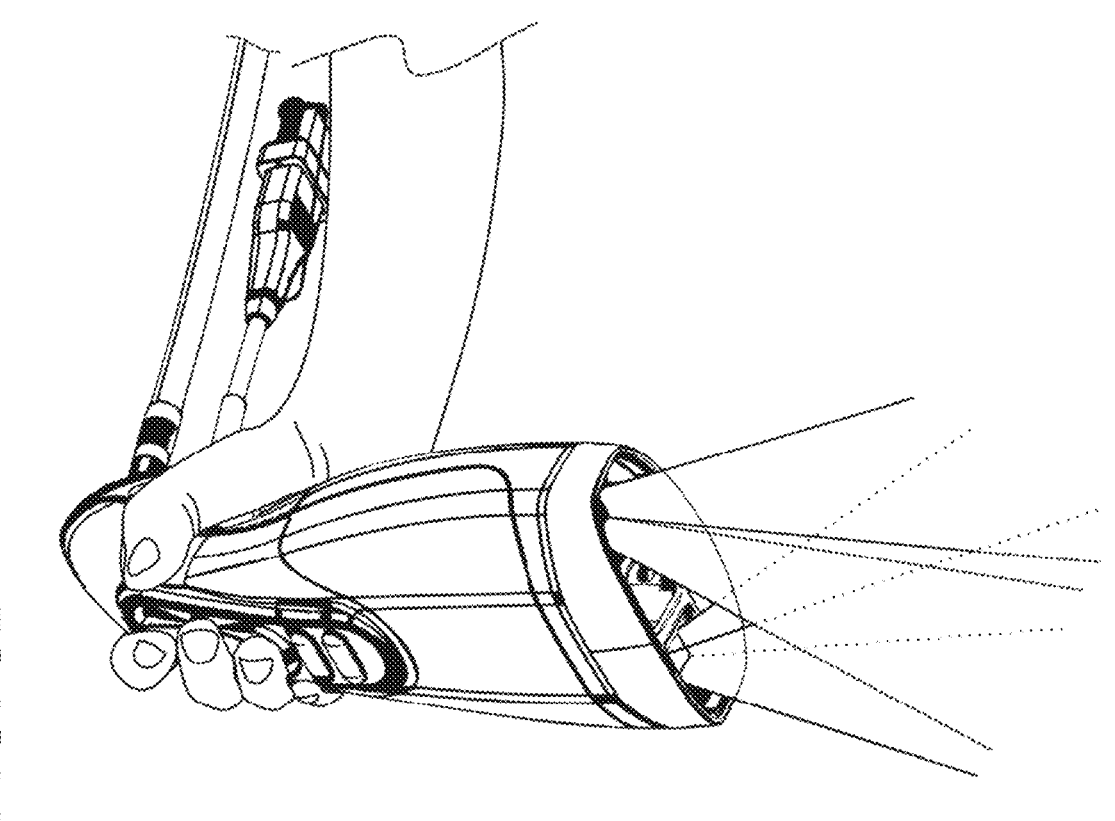

As can be seen in FIG. 8A, when the enclosure 60 is held with the imaging window facing forward, the thumb rests on the control surface 62 while the other fingers on the operator's hand are wrapped loosely around the bottom of the grip detail 64. As can be seen in FIG. 8B, when the enclosure 60 is held with the imaging window facing downward, the grip detail 64 is between the thumb and index finger and the fingers are wrapped around to access the control buttons or switches on the control surface 62. The grip detail 64 is sculpted so as to provide for partial support of the device weight on the top of the wrist in the vertical-orientation grip, such that the enclosure 60 can hang loosely and without the need for a tight grip of the enclosure 60. Thus, the enclosure 60 may be operated by a single hand in multiple orientations. In various other embodiments, the enclosure 60 may be supported on a support (e.g., a moveable support).

The window frame 68 (see also FIG. 9), defines the different windows for the enclosure 60. In other words, the window frame 68 defines windows 68a and 68b, corresponding to the two lens modules 20a and 20b, as well as window 68c, which serves as an input window for light from the target to be incident on the sensor 52.

Figure 9:
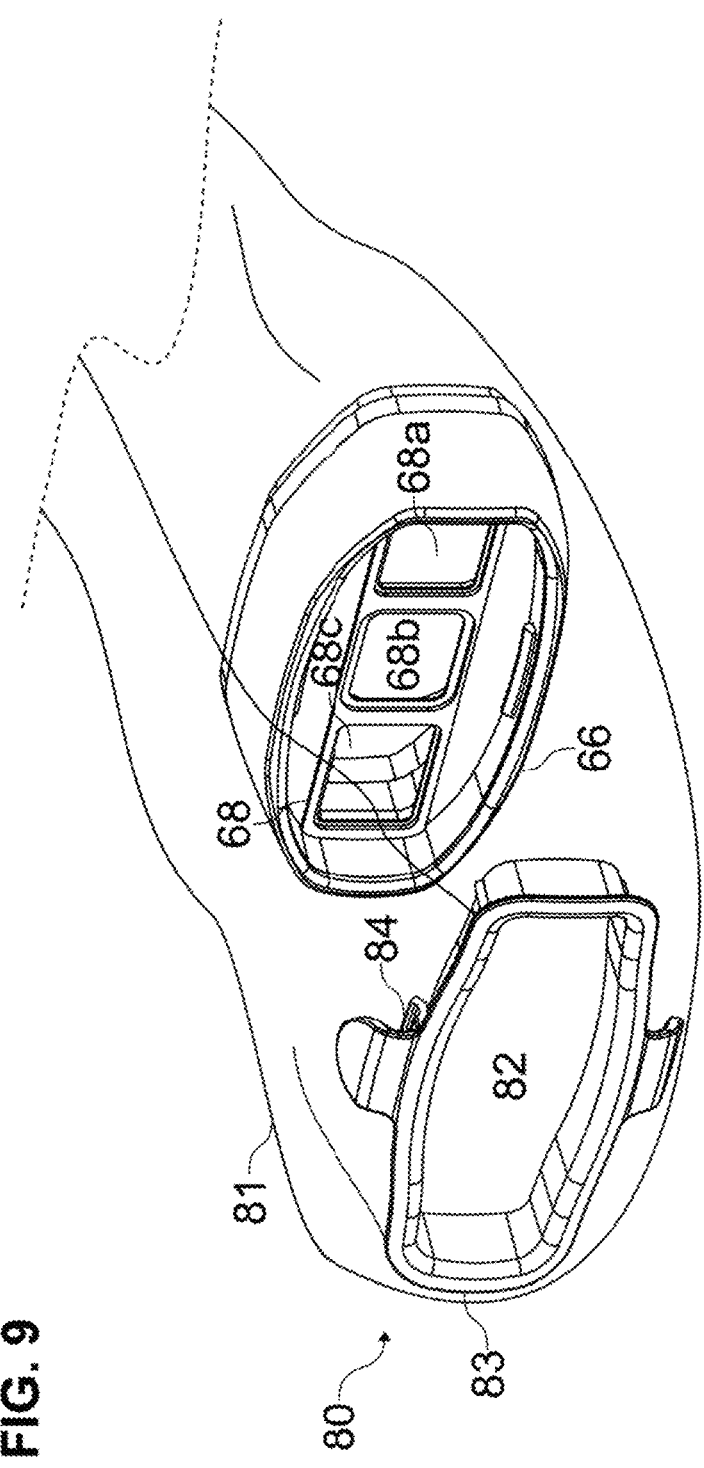
FIG. 9 illustrates a drape for use with the system according to an embodiment.

As illustrated in FIG. 9, the enclosure 60 may be used in concert with a drape 80. The drape 80 may be a surgical drape suitable for use during a surgical procedure. The drape includes drape material 81, a drape lens 82, a drape window frame 83 surrounding the drape lens, and an interlock interface 84 that is integral with the drape window frame 83. The drape material 81 is to envelope the device in the enclosure 60, as well as to cover anything else as required. The drape window frame 83 may follow a shape of the enclosure nosepiece 66 such that the drape window frame 83 may be inserted therein without obstructing the windows 68a to 68c. The drape 80 is designed to minimize reflections and imaging ghosting by ensuring the drape lens 82 is flush, e.g., to within 0.5 mm, with the imaging and illumination window frame 68. The drape 80 may use the interlock interface 84, which may fit into a recess on the inner surface of the enclosure nosepiece 66, to be secured flush thereto.

One or more interlock interfaces 84 may be used on the inner or outer surface of the enclosure nosepiece 66, in order to ensure a secure and close fit of the drape lens 82 against the window frame 68. In the particular embodiment shown, two interfaces 84, here one on the top and one on the bottom of the drape window frame 83 to engage with an inner surface of the enclosure nosepiece 66, are used.

Figure 10A:
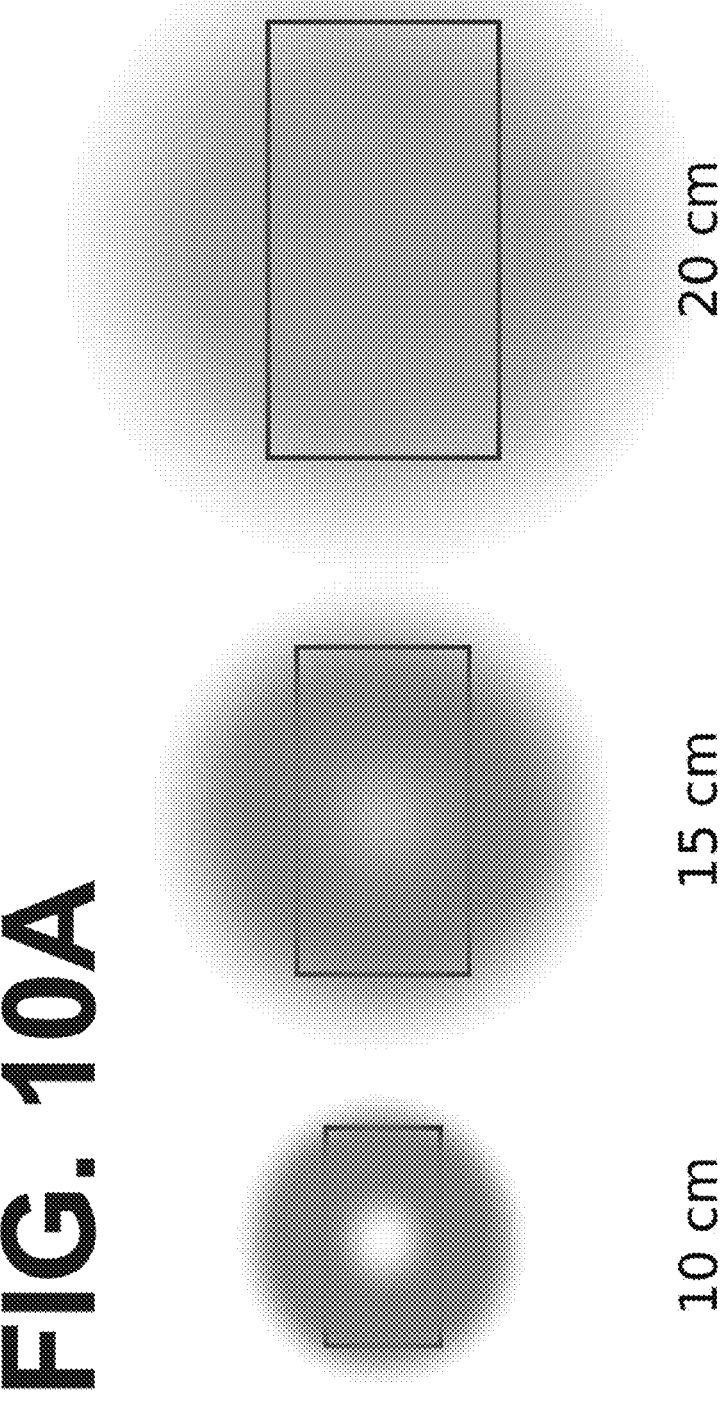
FIGS. 10A to 10C illustrate illumination distributions for different illumination configurations.
Figure 10B:
Figure 10B:
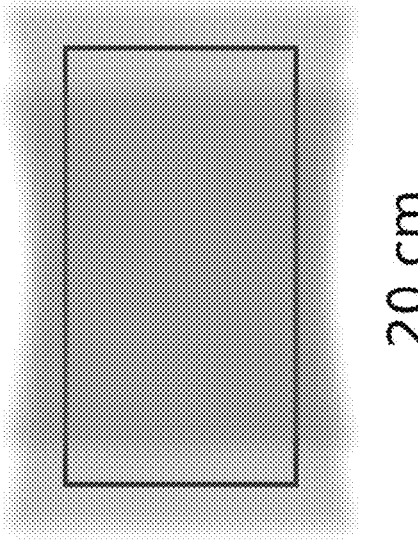
Figure 10B:
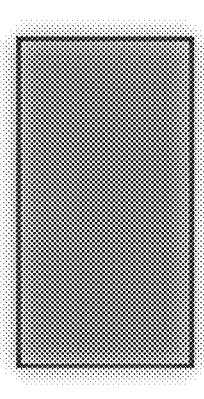
Figure 10B:
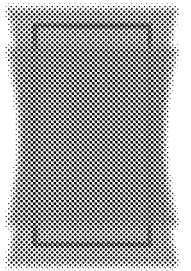
Figure 10C:
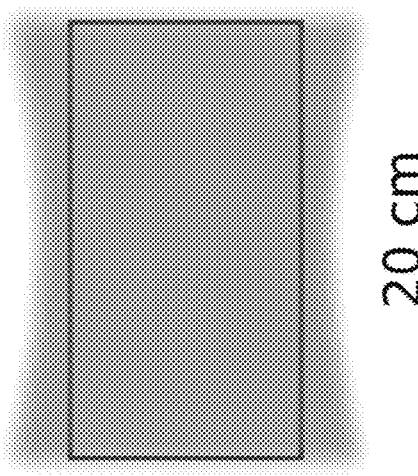
Figure 10C:
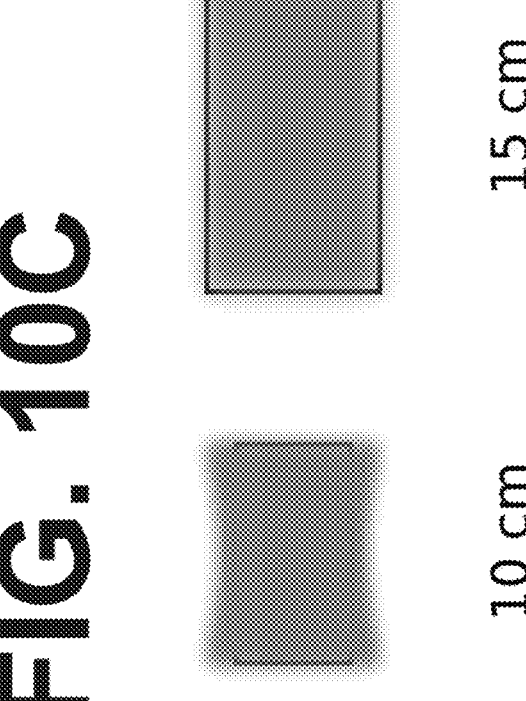

FIGS. 10A to 10C illustrate typical illumination distributions (fill) relative to a rectangular imaging field of view (outline) for an illumination ring (FIG. 10A), a pair of fixed anamorphic projection illumination sources (FIG. 10B), and a pair of steered anamorphic projection illumination sources in accordance with an embodiment (FIG. 10C) at working distances of 10 cm (left column), 15 cm (center column), and 20 cm (right column). FIG. 10A illustrates use of a ring of illumination ports to minimize shadowing, but does not match illumination to the imaging field of view and may not provide even illumination at all working distances (e.g. varied distributions in accordance with distance). FIG. 10B illustrates anamorphic projection from two illumination sources (using, e.g., an illumination lens arrangement featuring cylindrical lenses or an engineered diffuser) that are fixed, thus they are well calibrated for even illumination that matches the imaging field of view at a fixed working distance, e.g., 15 cm, but not as even or well matched at other distances, whether smaller or greater. As noted above, such illumination is often acceptable on its own. FIG. 10C illustrates the ability to better maintain even illumination and constrain illumination to the field of view by steering illumination when changing the working distance (and imaging focus) in accordance with an embodiment.

As noted above, the illumination used may include both white light and fluorescence excitation illumination, e.g., from a laser, to excite near infrared (NIR) light from the target. However, ambient light may interfere with the light from the target.

Figure 11A:
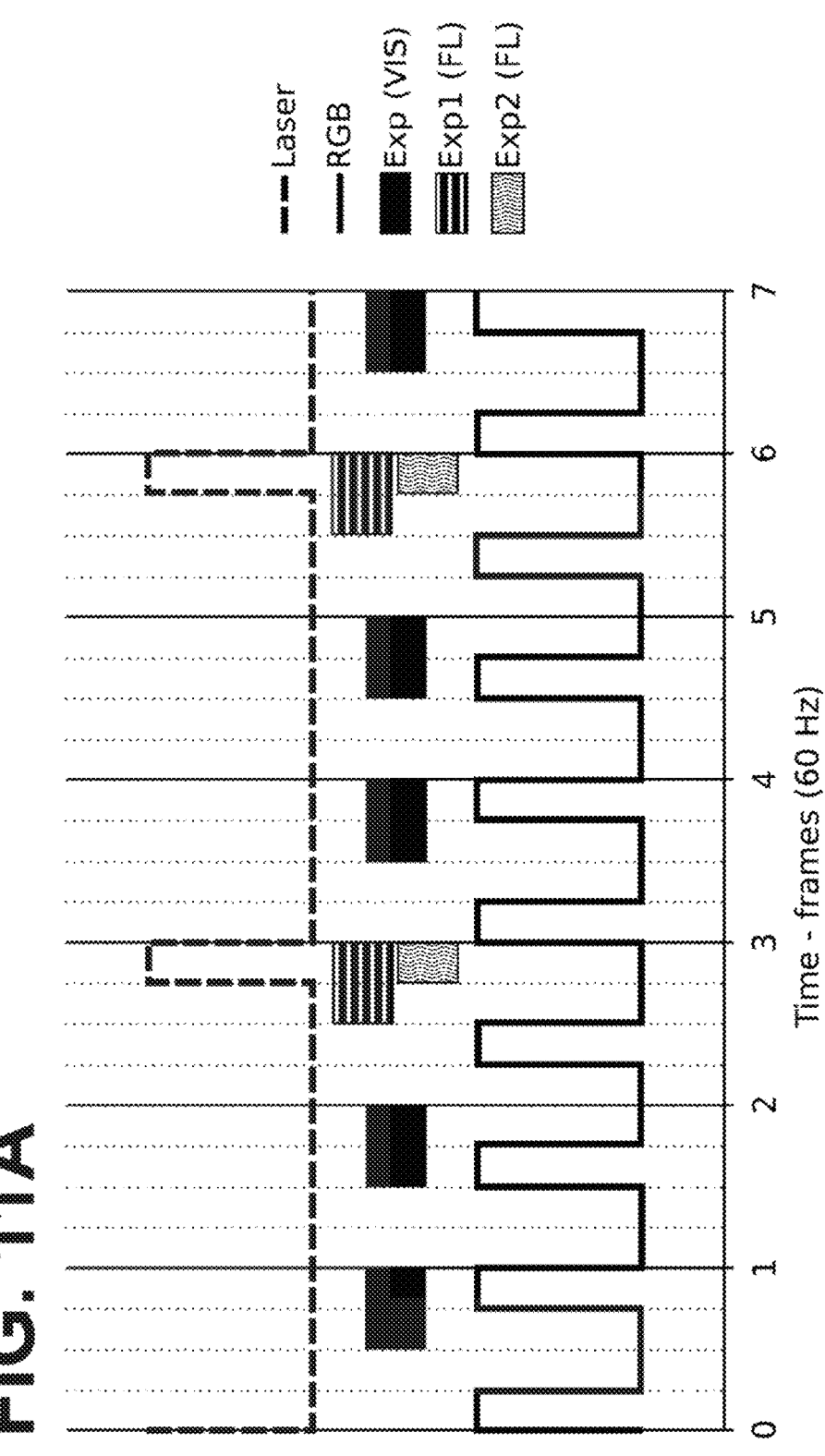
FIG. 11A illustrates a timing diagram for visible and excitation illumination according to an embodiment.

FIG. 11A illustrates a timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. As used herein, a white pulse will indicate that the white light (RGB) is illuminating the target and an excitation pulse will indicate that the laser is illuminating the target.

Exposures of even (Exp 1) and odd (Exp 2) sensor pixel rows are shown interleaved with differing exposure times to facilitate isolation of an estimate of the ambient room light signal component. Such an interleaved exposure read-out mode is offered on some imaging sensors, such as the 'High Dynamic Range Interleaved Read-out' mode offered on the CMOSIS CMV2000 sensor.

Pulsing the white light illumination at 80 Hz brings the frequency of the flashing light above that which is perceptible by the human eye or which may trigger epileptic seizures. The visible light image exposure may be longer than, e.g., twice, the RGB illumination to ensure overlap between the 60 Hz exposure frame rate and the 80 Hz RGB illumination pulse. Extra ambient light captured during the visible exposure may be ignored, due to the much greater intensity of the RGB illumination pulse and signal from the target 12.

By setting the NIR fluorescence image exposure times Exp 1 and Exp 2 to acquire for one half frame and one quarter frame periods, respectively, while running the excitation laser only in the last one quarter of every third frame, the even rows (Exp 1) record one half frame of ambient room light in addition to one quarter frame of NIR fluorescence, while the odd rows (Exp 2) record one quarter frame of ambient room light plus one quarter frame of NIR fluorescence. Performing these fractional exposures within each visible or NIR fluorescence frame minimizes motion artifacts which would otherwise be caused by inserting additional exposure frames into the frame sequence for the purpose of ambient room light subtraction.

With such an acquisition design, an estimate of the ambient room light contribution to the image signals can be isolated by subtracting the Exp 2 sensor rows of the NIR fluorescence image from the Exp 1 sensor rows (interpolated to match Exp 2 pixel positions), yielding an estimate of one quarter frame of ambient room light signal. The estimate of one quarter frame of ambient room light signal can then be subtracted from the Exp 2 sensor rows of the NIR fluorescence image to yield an estimate of the NIR fluorescence signal with the one quarter frame of ambient room light removed. The control of the illumination and the exposure may be performed by the VPI box 14.

Figures 12A, 12B, 12C:
FIGS. 12A to 12C illustrate pixel layout and an interpolation scheme according to an embodiment.

In one embodiment, the above room light subtraction method may be altered in order to accommodate use of a Bayer-pattern color sensor. FIG. 12A illustrates a Bayer pattern arrangement of colored sensor pixels, wherein the even sensor rows and odd sensor rows have different filter arrangements (e.g., no red pixels in the even sensor rows and no blue pixels in the odd sensor rows), so the ambient light recorded on even rows will not be a good estimate of what reached the odd rows over the same period. However, every row does include green pixel signals, which are also sensitive to NIR fluorescence. Using only the green pixels, and performing a two-dimensional interpolation from the green pixel signals to the other pixel locations can yield an estimate of the ambient light signal component, and thus also of the NIR fluorescence or visible light components for the NIR and visible light images, respectively.

In order to calculate the NIR signal value at a given location, calculate the Exp 1 (even row) and Exp 2 (odd row) green pixel values near that location, with one or both of those values needing to be interpolated. FIG. 12B demonstrates an example wherein at a red pixel location, the best estimate of the Exp 1 (even row) green value is the average of the immediately neighboring green values above and below, while the best estimate of the Exp 2 (odd row) green value is the average of the immediately neighboring green values to the left and right.

The following mathematical example serves to illustrate an embodiment of the ambient room light subtraction method. If A=ambient light incident in one quarter frame period, and F=fluorescence incident in one quarter frame period, then:

$$Exp\ 1 = 2A + F$$

$$Exp\ 2 = A + F$$

Solving for F yields:

$$F = 2 * Exp2 - Exp1$$

In the particular example illustrated in FIG. 11A, a period for the sensing is three frames, the white light pulse and the excitation pulse have a same duration or width, but different frequencies, the visible light is sensed during two frames, e.g., the first two frames, and the fluorescence is sensed for during one frame, e.g., the third or final frame, for two different exposure times. As shown therein, the visible exposure time may be twice the duration of the white light pulse, a first fluorescent exposure times may be equal to the duration of the excitation pulse, and a second fluorescent exposure time may be pulse longer, e.g., twice, than the excitation pulse. Further, the visible exposure may have a different frequency than the white light pulse, e.g., visible exposure does not occur with every white light pulse, while the fluorescent exposure may have a same frequency as the excitation pulse.

Alternative timing and exposure diagrams are discussed below, in which a sensor having rows that are all active for a common exposure duration may be used while still compensating for ambient light using a single sensor. For example, background light may be directly detected by the sensor when the target is not illuminated. Other variations on pulsing, exposing, and sensing may be apparent to those of skill in the art.

Figure 11B:
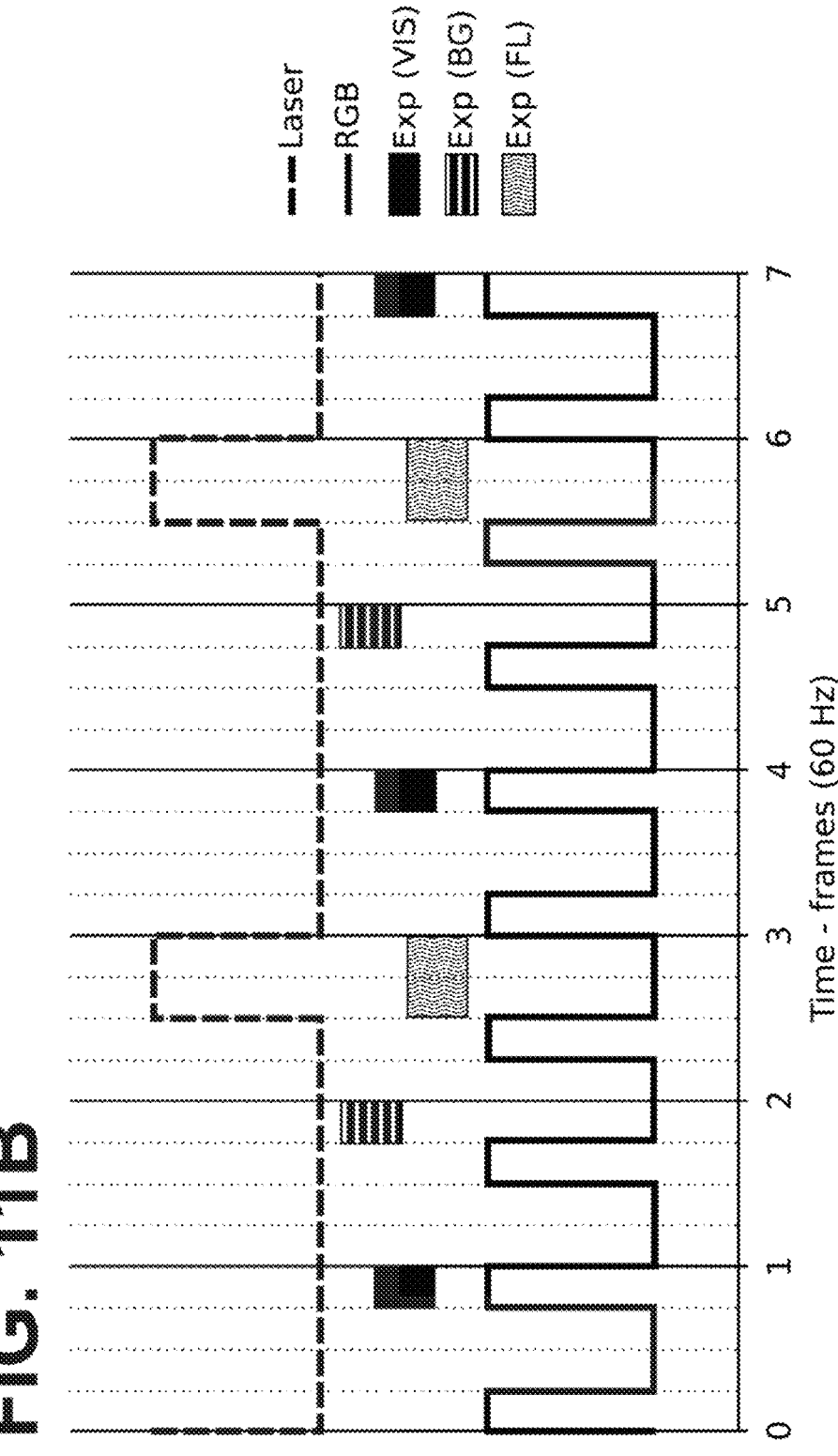
FIG. 11B illustrates a timing diagram for visible and excitation illumination according to an embodiment.

FIG. 11B illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor. Exposures for visible light and for fluorescence are shown in sequence along with an exposure to capture the background (BG) image signal due to ambient light. The white light illumination may be pulsed at 80 Hz as described above. The fluorescence excitation illumination may be pulsed at 20 Hz and the pulse duration or width may be increased, e.g., up to double the white light pulse duration, to enable a longer corresponding fluorescence exposure. If using an imaging sensor with a global shutter, each sensor exposure must terminate with the read-out period at the end of an imaging frame. An exposure to capture the ambient light background image signal may be performed at the end portion of a frame in the absence of any pulsed white light or excitation light. In the case of acquiring video at a frame rate of 60 Hz, as shown in the example in FIG. 11B, a white light illumination pulse width of one quarter frame duration may be used, along with a one quarter frame duration visible light exposure occurring in frames when the end of a white light illumination pulse is aligned with the end of the frame.

A scaled image signal recorded during one or more background exposures can be subtracted from each fluorescence exposure image to remove the contribution of ambient light from the fluorescence image. For example, the image signal from a one quarter frame duration background exposure may be scaled up by two times and subtracted from a subsequent image signal from a one half frame duration fluorescence exposure. As another example, a one quarter frame duration background exposure image signal prior to a one half frame duration fluorescence exposure image signal, and a second one quarter frame background image signal subsequent to the fluorescence exposure, may both be subtracted from the fluorescence image signal. Scaling of the image signals from a first and a second background exposure can include interpolation of pixel values from the first exposure time point and the second exposure time point to estimate pixel values corresponding to an intermediate time point.

Use of an imaging sensor with high speed read-out that enables higher video frame acquisition rates may allow for additional exposure periods to be allocated within an illumination and exposure timing scheme for a given white light pulse frequency. For example, maintaining an 80 Hz white light illumination pulse as above and using a sensor with a higher video frame acquisition rate such as 120 Hz may allow additional white light, ambient background, or fluorescence exposures within a given time period, compared to when using a slower video frame acquisition rate such as 60 Hz.

In the particular example illustrated in FIG. 11B, a period for the sensing is three frames, the excitation pulse has twice the width of the white light pulse, the visible light is sensed during one frame, e.g., the first frame, the background light is sensed during one frame, e.g., the second frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

Figure 11C:
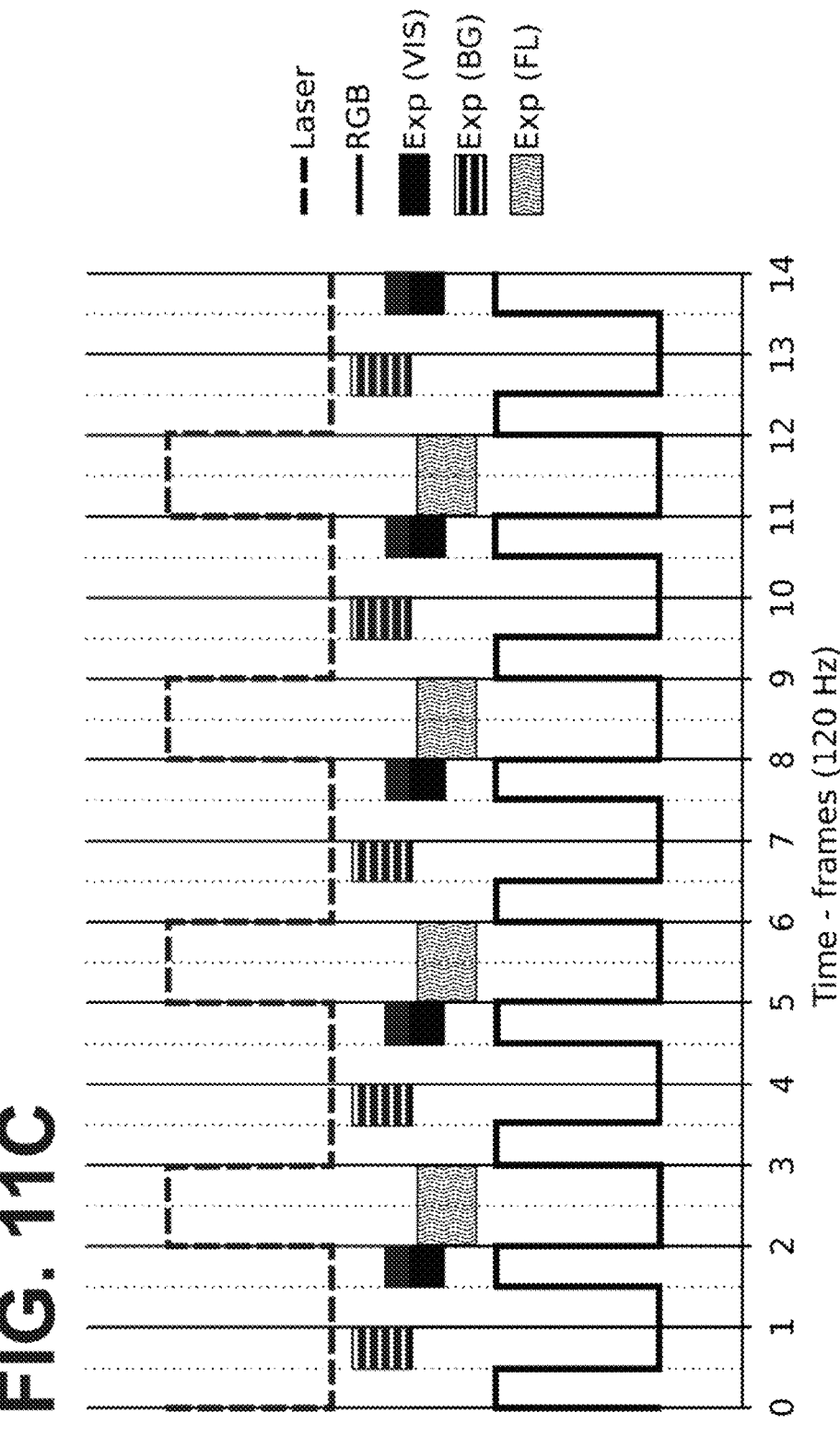
FIG. 11C illustrates a timing diagram for visible and excitation illumination according to an embodiment.

FIG. 11C illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one half frame duration may be used, along with a one half frame duration visible light exposure occurring in frames when the end of a white light illumination pulse is aligned with the end of the frame. The fluorescence excitation illumination is shown pulsed at 40 Hz with a pulse duration of one frame, to enable a higher frequency of corresponding fluorescence exposures. An exposure to capture the ambient light background image signal may be performed at the end portion of a frame in the absence of any pulsed white light or excitation light, such as an exposure of one half frame duration occurring in the frame between a fluorescence exposure and a successive white light exposure as shown in this example embodiment.

In the particular example illustrated in FIG. 11C, a period for the sensing is three frames, the excitation pulse has twice the width of the white light pulse, the visible light is sensed during one frame, e.g., the second frame, the background light is sensed during one frame, e.g., the first frame, and the fluorescence is sensed during one frame, e.g., the third or final frame. Here, a visible exposure time may be equal to the duration of the white light pulse, the background exposure time may be equal to the duration of the white light pulse, and the fluorescence exposure time may be equal to the duration of the excitation pulse. Further, the visible exposure may have a different frequency than the white light pulse, e.g., visible exposure does not occur with every white light pulse, while the fluorescent exposure may have a same frequency as the excitation pulse. Finally, the background exposure may occur only once within the period.

Depending on the intensity of the fluorescence excitation light used, there may be safety considerations limiting the duration and frequency of excitation light pulses. One approach to reduce the excitation light intensity applied is to reduce the duration of the excitation light pulses and the corresponding fluorescence exposures. Additionally or alternatively, the frequency of excitation light pulses (and corresponding fluorescence exposures) may be reduced, and the read-out periods which could otherwise be used for fluorescence exposures may instead be used for background exposures to improve measurement of the ambient light.

Figure 11D:
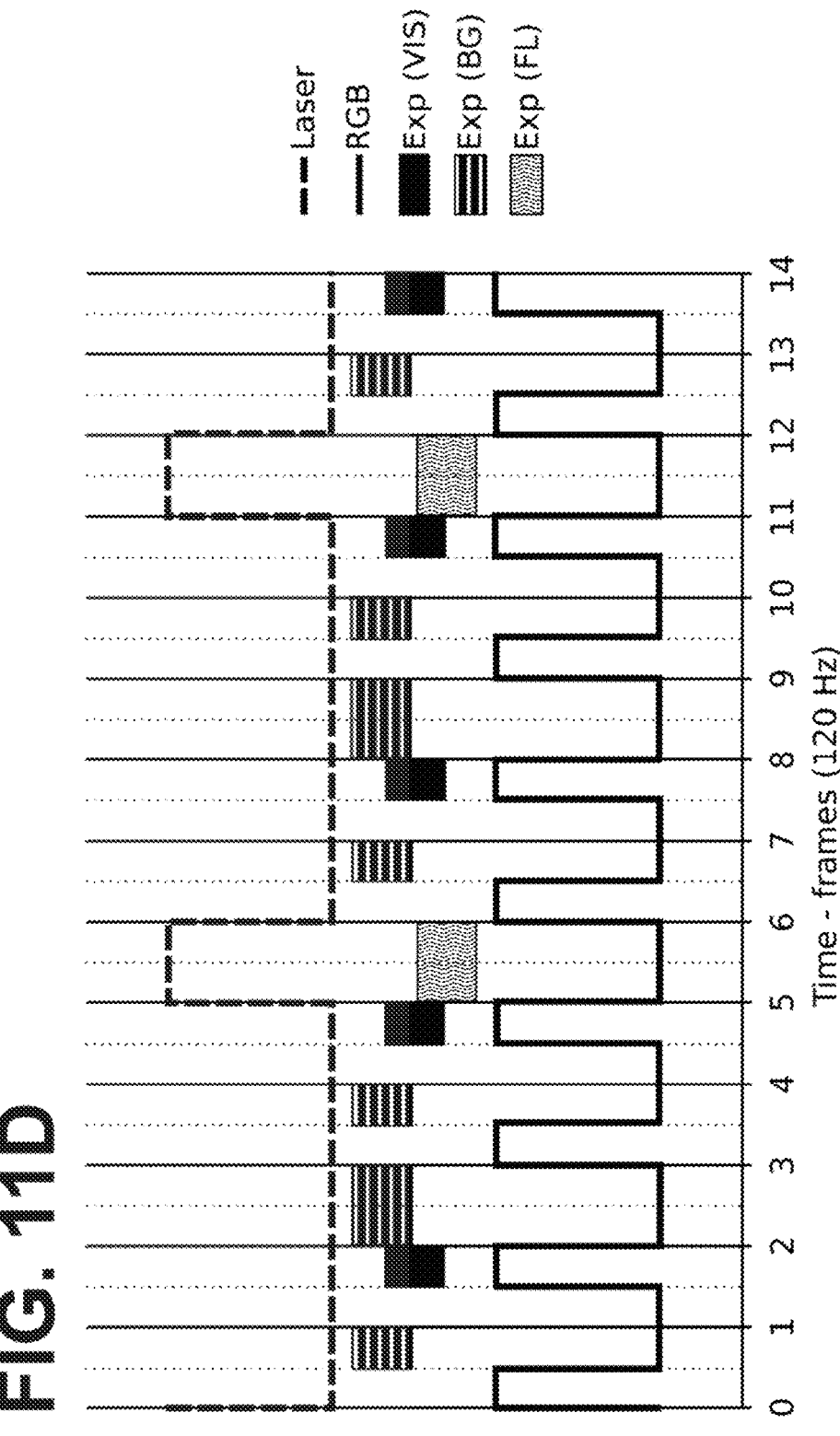
FIG. 11D illustrates a timing diagram for visible and excitation illumination according to an embodiment.

FIG. 11D illustrates an alternative timing diagram for white light (RGB) and fluorescence excitation (Laser) illumination, and visible (VIS) and NIR fluorescence (FL) imaging sensor exposures configured to allow ambient room light subtraction from the fluorescence signal with a single sensor with a 120 Hz video frame acquisition rate. A white light pulse frequency of 80 Hz is used, and a white light illumination pulse width of one half frame duration may be used, along with a one half frame duration visible light exposure occurring in frames when the end of a white light illumination pulse is aligned with the end of the frame. The fluorescence excitation illumination is shown pulsed at 20 Hz with a pulse duration of one frame. An exposure to capture the ambient light background image signal may be performed at the end portion of a frame in the absence of any pulsed white light or excitation light, such as a background exposure of one half frame duration occurring in the frame between a fluorescence exposure and a successive first white light exposure, and a first background exposure of one frame duration and a second background exposure of one half frame duration both occurring in the frames between the first white light exposure and a successive second white light exposure, as shown in this example embodiment.

In the particular example illustrated in FIG. 11D, a period for the sensing is six frames, the excitation pulse has twice the width of the white light pulse, the visible light is sensed during two frames, e.g., the second and fifth frames, the background light is sensed during three frames, e.g., the first, third, and fourth frames, and the fluorescence is sensed for during one frame, e.g., the sixth or final frame. Here, a visible exposure time may be equal to the duration of the white light pulse, the background exposure time may be equal to or twice the duration of the white light pulse, and the fluorescence exposure time may be equal to the duration of the excitation pulse. Further, the visible exposure may have a different frequency than the white light pulse, e.g., visible exposure does not occur with every white light pulse, e.g., only twice within the period, while the fluorescent exposure may have a same frequency as the excitation pulse. Finally, the background exposure may occur three times within the period for a total duration equal to four times the duration of the white light pulse.

To improve performance of such ambient room light compensation methods as described above, a wavelength-dependent aperture (e.g., element 55 in FIG. 6A) may be used that includes a smaller central aperture that permits transmission of all visible and NIR light, and a surrounding larger aperture that blocks visible light but permits transmission of NIR light. Use of such a wavelength-dependent aperture allows a larger proportion of NIR signal to be collected relative to the visible light signal, which improves performance of the image signal subtraction for estimation and removal of the ambient room light component. A wavelength-dependent aperture may also feature a third, larger aperture, surrounding the other smaller apertures, that blocks both visible and NIR light. As an example, a wavelength-dependent aperture may comprise a film aperture, wherein a film (e.g., a plastic or glass film) of material that blocks transmission of visible light but permits transmission of NIR light has a central opening (e.g., a hole) that permits transmission of both visible and NIR light. Such a film aperture may comprise material that blocks transmission of visible light through reflection and/or material that blocks transmission of visible light through absorption. As another example, a wavelength-dependent aperture may comprise a dichroic aperture which is formed by masked thin-film deposition on a single substrate, wherein a thin-film that permits transmission of visible and NIR light is deposited on a smaller central aperture, and a second thin-film that blocks transmission of visible light but permits transmission of NIR light is deposited on a surrounding larger aperture. The respective aperture sizes of the smaller central aperture and the surrounding larger aperture of a wavelength-dependent aperture may be set in order to make the depth of field for visible light and for NIR light appear substantially similar when imaged by the imaging system. One or more wavelength-dependent filters may be placed in different positions throughout the device, where rejection of the visible and passage of the NIR signal may be optimized. For example, such a wavelength-dependent filter may be positioned just before the lens 51. As another example, one or more wavelength-dependent filters may be placed in a pupil plane of the imaging lens.

It may be useful, e.g., to facilitate comparison of the fluorescence signal of different regions, to display a target reticle around a region within the imaged field of view, and to calculate and display the normalized fluorescence intensity within that region. Normalization of the measured fluorescence intensity values may allow for meaningful comparison of multiple images and corresponding values. To correct for the variation of measured fluorescence intensity with working distance (e.g., distance of the imaging system to the imaged anatomy), normalized fluorescence intensity values may be based on a ratio between the measured fluorescence intensity values and a reflected light value within the target reticle region.

A numerical representation of the normalized fluorescence intensity value within the target reticle region may be displayed on or near the image frame, to facilitate comparing values when aiming the target reticle at different locations on the imaged anatomy. For example, the numerical represen-
tation may be the mean value of the normalized fluorescence
intensity values for all of the image pixels in the target reticle
region.

Additionally or alternatively, a time history plot of the
numerical representation of the normalized fluorescence
intensity value within the target reticle region may be
displayed on or near the image frame, to facilitate comparing
values when aiming the target reticle at different locations on
the imaged anatomy or at the same location over a series of
time points. Such a time history plot may further assist the
user in assessing the fluorescence profile in the imaged
tissue surface by scanning across the anatomy region of
interest and viewing the relative normalized fluorescence
intensity profile plot.

Figure 13A:
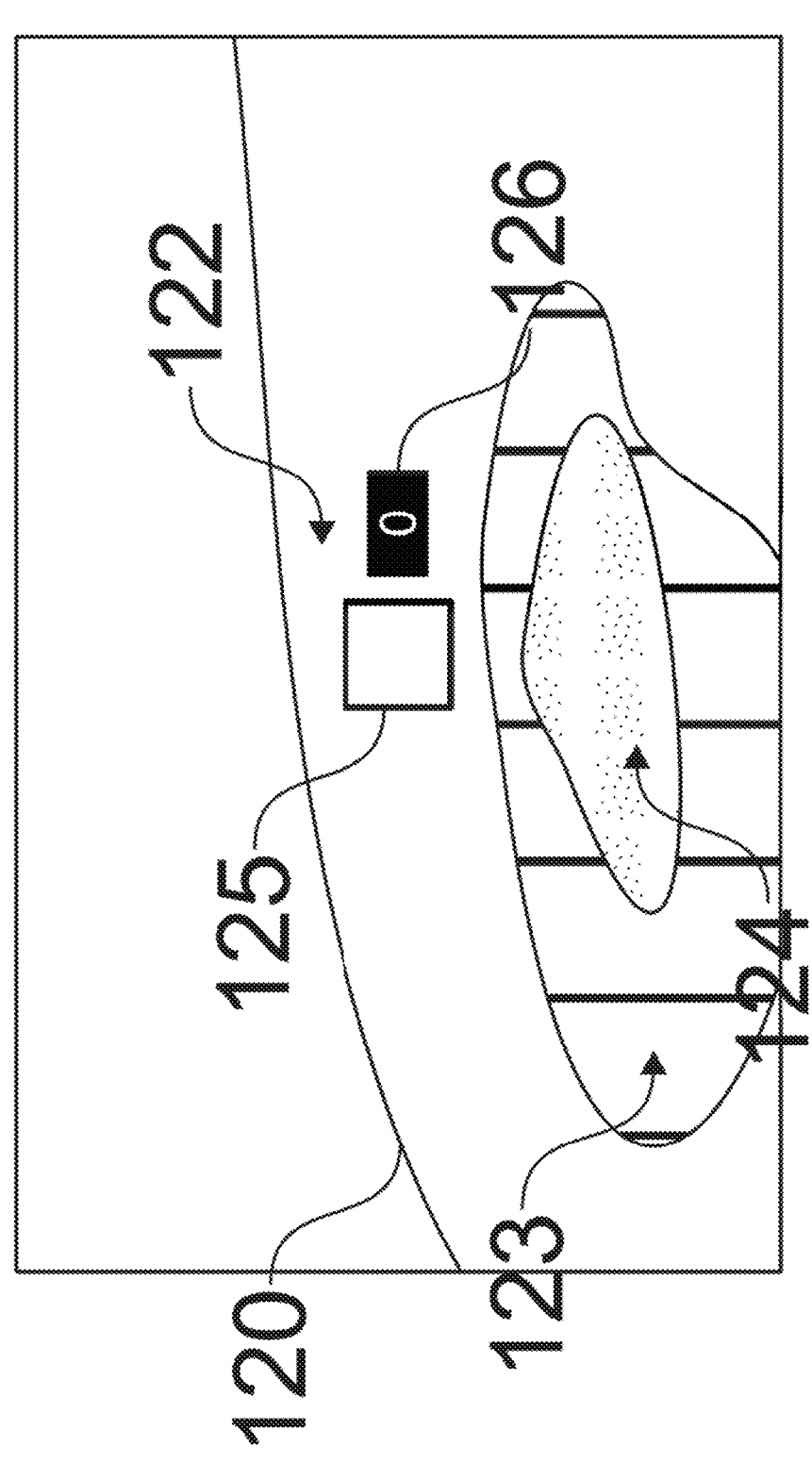
FIGS. 13A to 13C illustrate diagrams of an embodiment of a display method output when a target reticle is placed over regions of no normalized fluorescence intensity, high relative normalized fluorescence intensity, and moderate relative normalized fluorescence intensity, respectively.
Figure 13B:
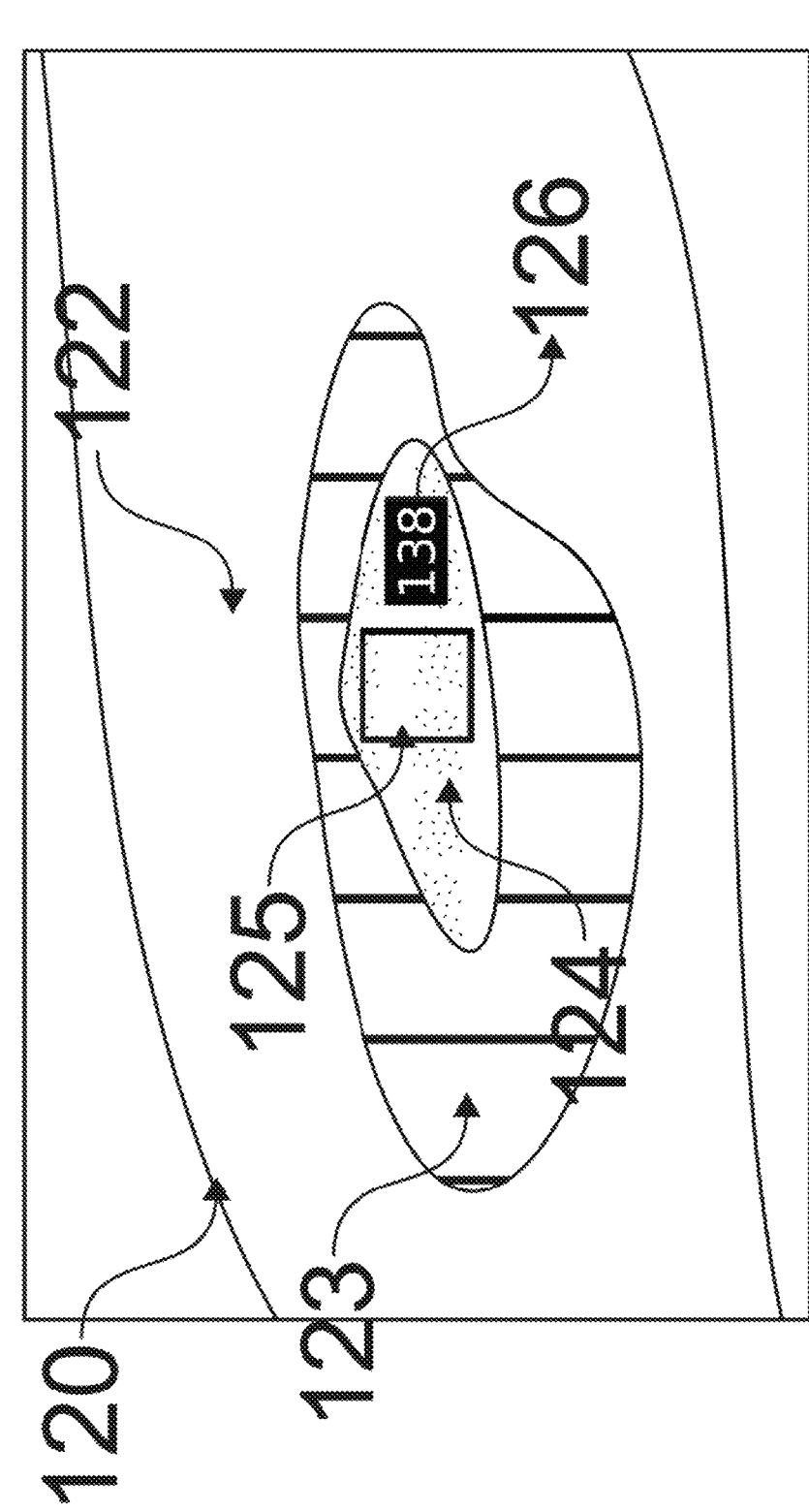
Figure 13C:
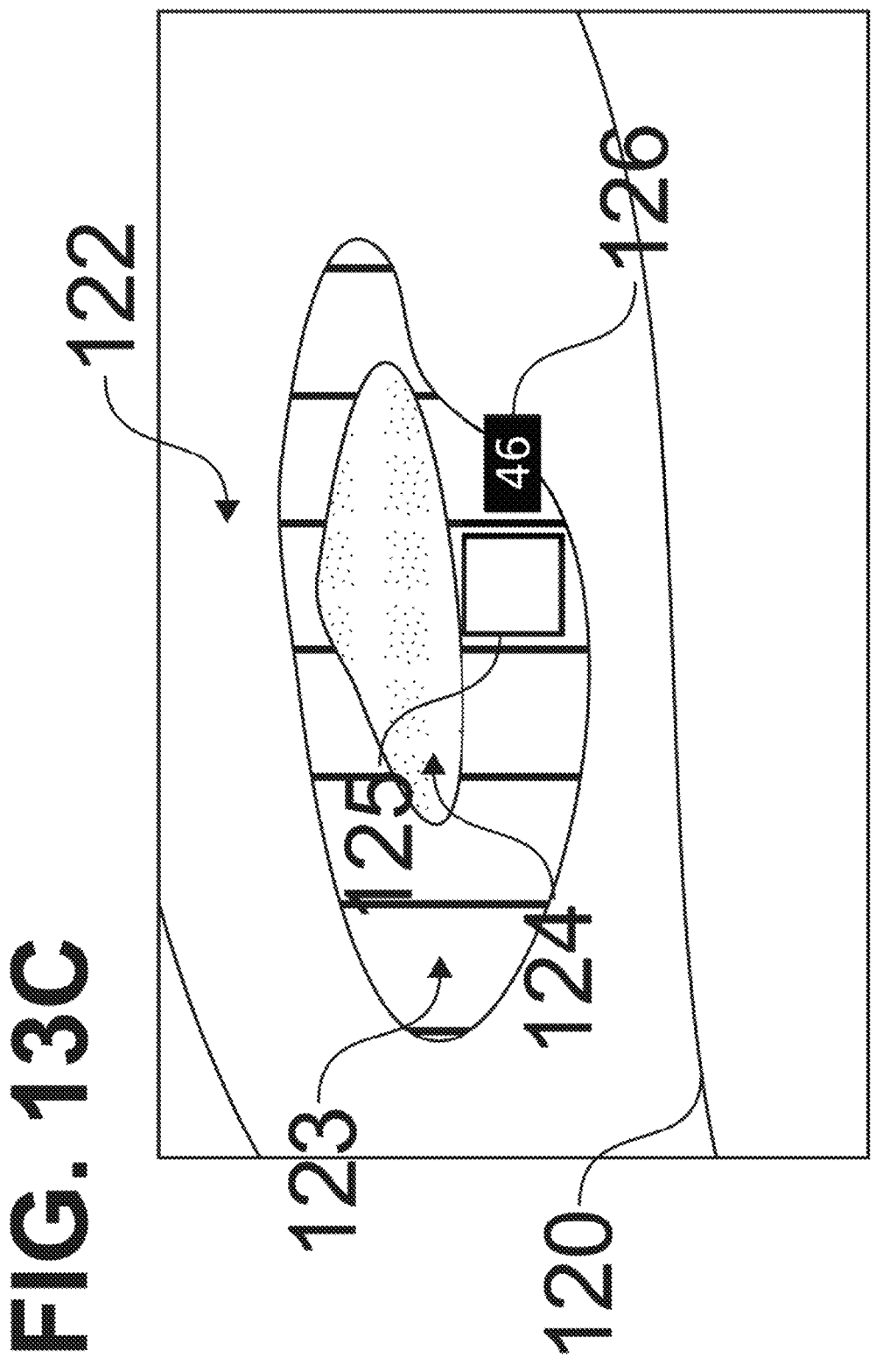
Figure 13D:
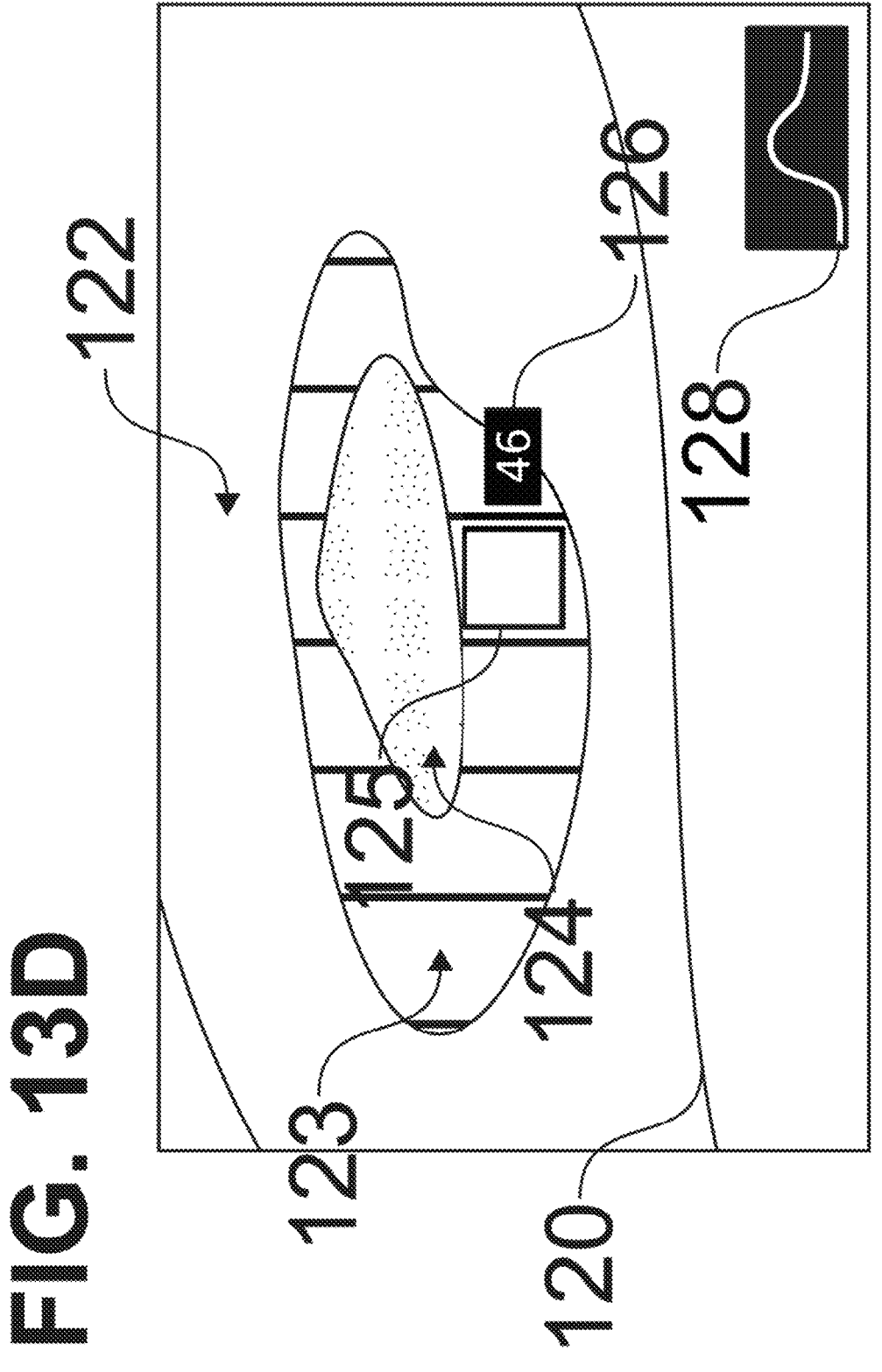
FIG. 13D illustrates a diagram of an embodiment of a display method output that includes a signal time history plot of normalized fluorescence intensity values on the display.

FIG. 13A illustrates a diagram of a sample display output
from an embodiment of the display method, wherein the
target reticle 125 is positioned over a region of no fluores-
cence intensity 122 on the imaged anatomy 120, and the
numerical representation of the fluorescence intensity 126 is
displayed near the target reticle 125. FIG. 13B illustrates a
diagram of another sample display output, wherein the target
reticle 125 is positioned over a region of high relative
normalized fluorescence intensity 124, and showing a cor-
responding numerical representation 126 of relatively high
fluorescence intensity. FIG. 13C illustrates a diagram of
another sample display output, wherein the target reticle 125
is positioned over a region of moderate relative normalized
fluorescence intensity 124, and showing a corresponding
numerical representation 126 of relatively moderate fluo-
rescence intensity. FIG. 13D illustrates a diagram of a
sample display output, wherein the target reticle 125 is
positioned over a region of moderate relative normalized
fluorescence intensity 124, and showing a time history plot
128 of the numerical representation of normalized fluores-
cence intensity that would be consistent with sequential
imaging of regions of zero, high, and moderate relative
normalized fluorescence intensity. Alternatively or addition-
ally to displaying the numerical representation and/or his-
torical plot on the target, a display region associated with the
target reticle, e.g., on the device itself or some other display,
may display this information.

Figure 14:
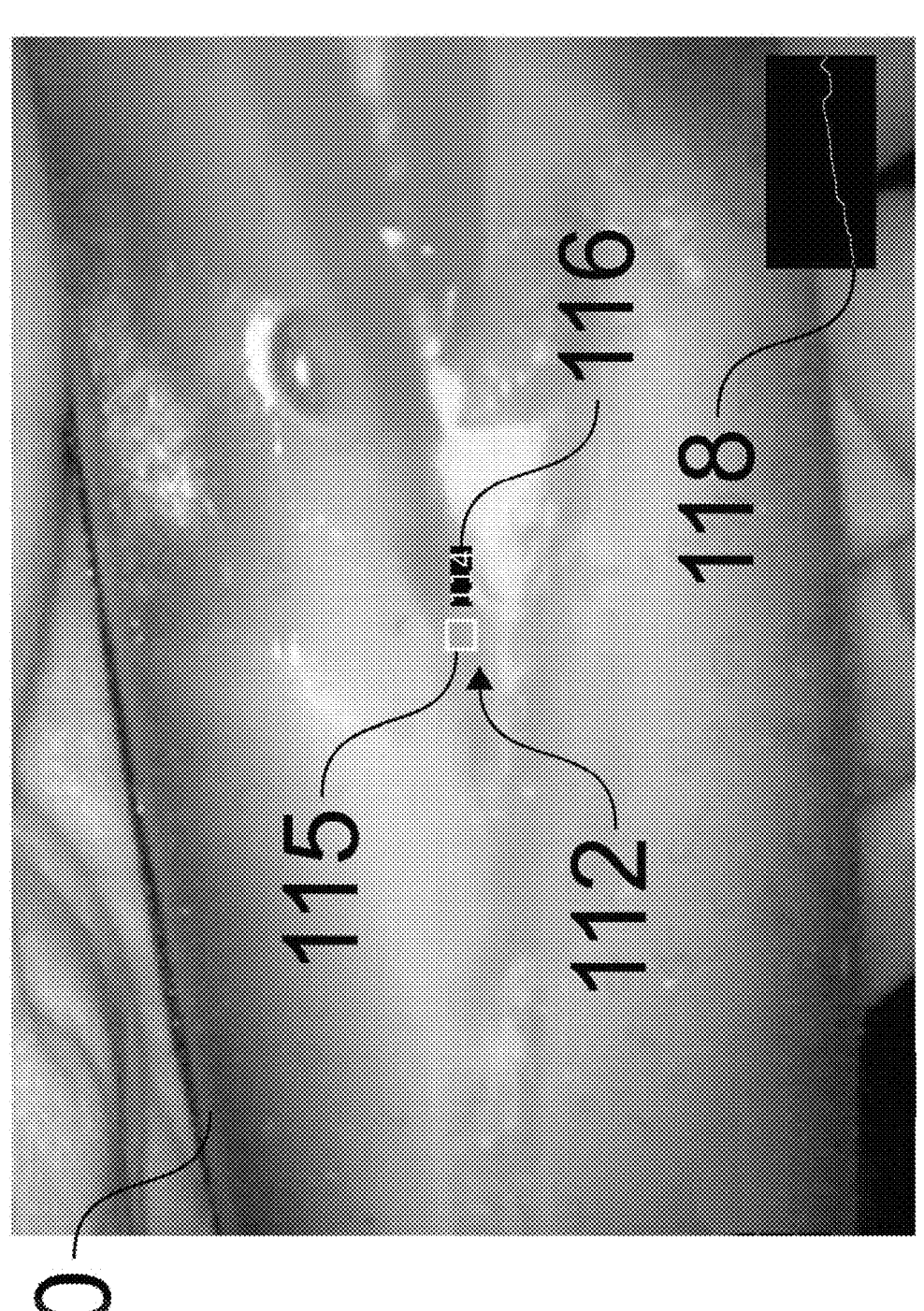
FIG. 14 illustrates a recorded image of an anatomical fluorescence imaging phantom, featuring an embodiment of a display method output that displays normalized fluorescence intensity.

FIG. 14 illustrates a recorded image of an anatomical
fluorescence imaging phantom, featuring an embodiment of
a display method output that displays normalized fluores-
cence intensity. In particular, a target 110 is illuminated by
excitation light in accordance with an embodiment and a
target reticle 115 is positioned over a region of fluorescence
intensity 112. A numerical representation of the target reticle
115 is displayed in a region 116 associated with the target
reticle 115. A time history plot 118 of the numerical repre-
sentation of normalized fluorescence intensity due to imag-
ing of different positions of the reticle 115 may be displayed.

Such a display method may be useful for a variety of
fluorescence imaging systems, including an endoscopic or
laparoscopic fluorescence imaging system, an open field
fluorescence imaging system, or a combination thereof.
Such normalization and display of the fluorescence intensity
values can allow useful quantitative comparisons of relative
fluorescence intensity between image data from various time
points within an imaging session. Combined with appropri-
ate standardized fluorescent agent administration and imag-
ing protocols, and standardized calibration of imaging
devices, such normalization and display of the fluorescence
intensity values can further allow useful quantitative com-
parisons of relative fluorescence intensity between image
data from different imaging sessions.

EXAMPLES

A Fluorescence Medical Imaging System for Acquisition of
Image Data

In some embodiments, a system for illumination and
imaging of a subject may be used with or as a component of
a medical imaging system such as, for example, a fluores-
cence medical imaging system for acquiring fluorescence
medical image data. An example of such a fluorescence
medical imaging system is the fluorescence imaging system
10 schematically illustrated in FIG. 1. In this embodiment,
the fluorescence imaging system 10 is configured to acquire
a time series of fluorescence signal intensity data (e.g.,
images, video) capturing the transit of a fluorescence imag-
ing agent through the tissue.

The fluorescence imaging system 10 (FIG. 1) comprises
an illumination source 15 and illumination module 11 to
illuminate the tissue of the subject to induce fluorescence
emission from a fluorescence imaging agent 17 in the tissue
of the subject (e.g., in blood), an imaging module 13
configured to acquire the time series of fluorescence images
from the fluorescence emission, and a processor assembly
16 configured to utilize the acquired time series of fluores-
cence images (fluorescence signal intensity data) according
to the various embodiments described herein.

In various embodiments, the illumination source 15 (FIG.
1) comprises, for example, a light source 200 (FIG. 15)
comprising a fluorescence excitation source configured to
generate an excitation light having a suitable intensity and a
suitable wavelength for exciting the fluorescence imaging
agent 17. The light source 200 in FIG. 15 comprises a laser
diode 202 (e.g., which may comprise, for example, one or
more fiber-coupled diode lasers) configured to provide exci-
tation light to excite the fluorescence imaging agent 17 (not
shown). Examples of other sources of the excitation light
which may be used in various embodiments include one or
more LEDs, arc lamps, or other illuminant technologies of
sufficient intensity and appropriate wavelength to excite the
fluorescence imaging agent 17 in the tissue (e.g., in blood).
For example, excitation of the fluorescence imaging agent
17 in blood, wherein the fluorescence imaging agent 17 is a
fluorescent dye with near infra-red excitation characteristics,
may be performed using one or more 793 nm, conduction-
cooled, single bar, fiber-coupled laser diode modules from
DILAS Diode Laser Co, Germany.

Figure 15:
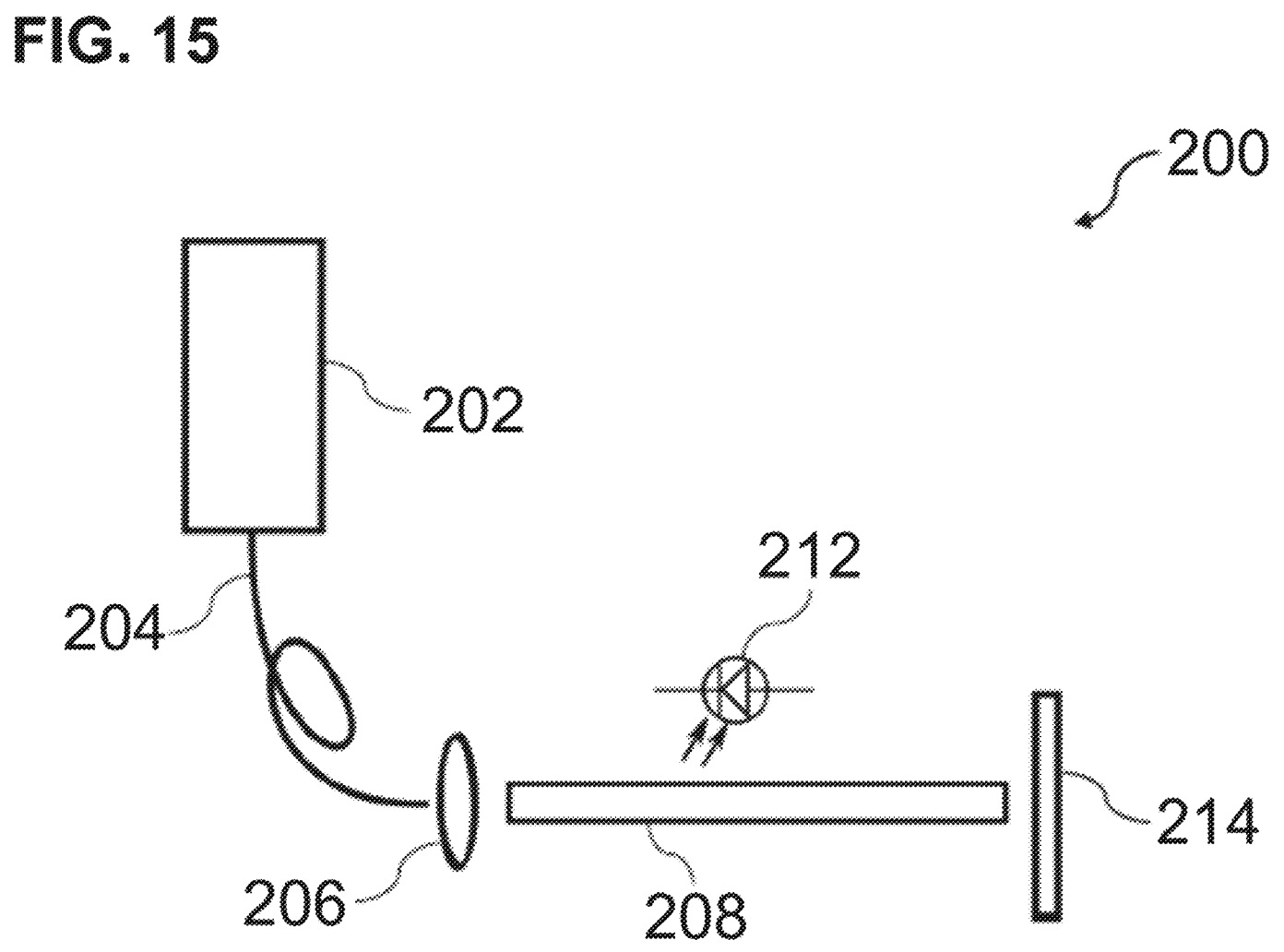

In various embodiments, the light output from the light
source 200 in FIG. 15 may be projected through an optical
element (e.g., one or more optical elements) to shape and
guide the output being used to illuminate the tissue area of
interest. The shaping optics may consist of one or more
lenses, light guides, and/or diffractive elements so as to
ensure a flat field over substantially the entire field of view
of the imaging module 13. In particular embodiments, the
fluorescence excitation source is selected to emit at a wave-
length close to the absorption maximum of the fluorescence
imaging agent 17 (e.g., ICG). For example, referring to the
embodiment of the light source 200 in FIG. 15, the output
204 from the laser diode 202 is passed through one or more
focusing lenses 206, and then through a homogenizing light
pipe 208 such as, for example, light pipes commonly avail-
able from Newport Corporation, USA. Finally, the light is
passed through an optical diffractive element 214 (e.g., one
or more optical diffusers) such as, for example, ground glass
diffractive elements also available from Newport Corpora-
tion, USA. Power to the laser diode 202 itself is provided by,
for example, a high-current laser driver such as those
available from Lumina Power Inc. USA. The laser may optionally be operated in a pulsed mode during the image acquisition process. In this embodiment, an optical sensor such as a solid state photodiode 212 is incorporated into the light source 200 and samples the illumination intensity produced by the light source 200 via scattered or diffuse reflections from the various optical elements. In various embodiments, additional illumination sources may be used to provide guidance when aligning and positioning the module over the area of interest. In various embodiments, at least one of the components of light source 200 depicted in FIG. 15 may be components comprising the illumination source 15 and/or comprising the illumination module 11.

Figure 16:
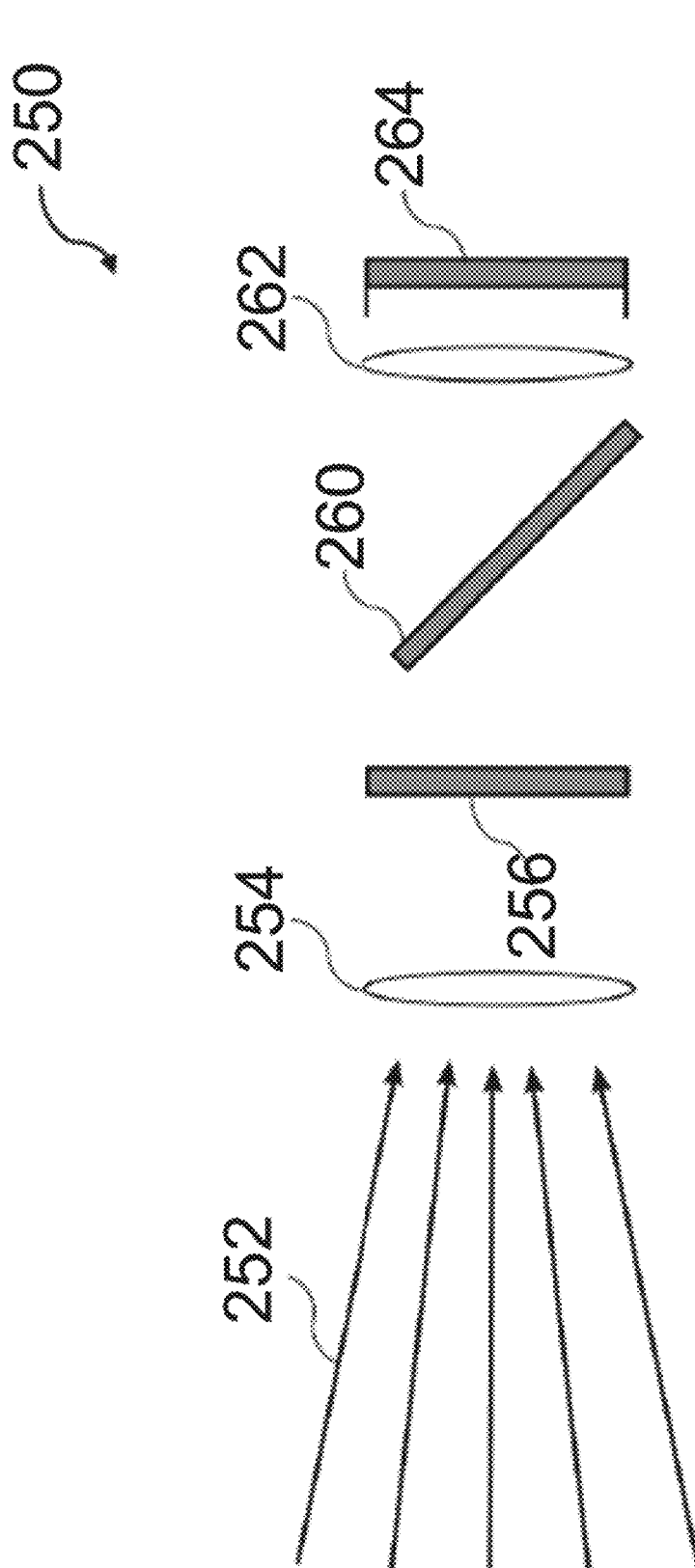
FIG. 16 illustrates an exemplary imaging module of the fluorescence imaging system in FIG. 1, the imaging module comprising a camera module.

Referring back to FIG. 1, in various embodiments, the imaging module 13 may be a component of, for example, the fluorescence imaging system 10 configured to acquire the time series of fluorescence images (e.g., video) from the fluorescence emission from the fluorescence imaging agent 17. Referring to FIG. 16, there is shown an exemplary embodiment of an imaging module 13 comprising a camera module 250. As is shown in FIG. 16, the camera module 250 acquires images of the fluorescence emission 252 from the fluorescence imaging agent 17 in the tissue (e.g., in blood) (not shown) by using a system of imaging optics (e.g., front element 254, rejection filter 256, dichroic 260 and rear element 262) to collect and focus the fluorescence emission onto an image sensor assembly 264 comprising at least one 2D solid state image sensor. A rejection filter 256 may be, for example, a notch filter used to reject a band of wavelengths corresponding to the excitation light. A dichroic 260 may be, for example, a dichroic mirror used to selectively pass one subset of the incoming light wavelength spectrum and redirect remaining wavelengths off of the optical path for rejection or towards a separate image sensor. The solid state image sensor may be a charge coupled device (CCD), a CMOS sensor, a CID or similar 2D sensor technology. The charge that results from the optical signal transduced by the image sensor assembly 264 is converted to an electrical video signal, which includes both digital and analog video signals, by the appropriate read-out and amplification electronics in the camera module 250.

According to some embodiments, excitation wavelength of about 800 nm+/−10 nm and emission wavelengths of >820 nm are used along with NIR compatible optics for ICG fluorescence imaging. A skilled person will appreciate that other excitation and emission wavelengths may be used for other imaging agents.

Referring back to FIG. 1, in various embodiments, the processor assembly 16 comprises, for example, a processor module (not shown) configured to perform various processing operations, including executing instructions stored on computer-readable medium, wherein the instructions cause one or more of the systems described herein to execute the methods and techniques described herein, and a data storage module (not shown) to record and store the data from the operations, as well as to store, in some embodiments, instructions executable by the processor module to implement the methods and techniques disclosed herein.

In various embodiments, the processor module comprises any computer or computing means such as, for example, a tablet, laptop, desktop, networked computer, or dedicated standalone microprocessor. Inputs are taken, for example, from the image sensor 264 of the camera module 250 shown in FIG. 16, from the solid state photodiode in the light source 200 in FIG. 15, and from any external control hardware such as a footswitch or remote-control. Output is provided to the laser diode driver, and optical alignment aids. In various embodiments, the processor assembly 16 (FIG. 1) may have a data storage module with the capability to save the time series of input data (e.g., image data) to a tangible non-transitory computer readable medium such as, for example, internal memory (e.g. a hard disk or flash memory), so as to enable recording and processing of data. In various embodiments, the processor module may have an internal clock to enable control of the various elements and ensure correct timing of illumination and sensor shutters. In various other embodiments, the processor module may also provide user input and graphical display of outputs. The fluorescence imaging system may optionally be configured with a video display (not shown) to display the images as they are being acquired or played back after recording, or further to visualize the data generated at various stages of the method as was described above.

In operation, and with continuing reference to the exemplary embodiments in FIGS. 1, 15 and 16, the subject is in a position for imaging where the anatomical area of interest of the subject is located beneath both the illumination module 11 and the imaging module 13 such that a substantially uniform field of illumination is produced across substantially the entire area of interest. In various embodiments, prior to the administration of the fluorescence imaging agent 17 to the subject, an image may be acquired of the area of interest for the purposes of background deduction. For example, in order to do this, the operator of the fluorescence imaging system 10 in FIG. 1 may initiate the acquisition of the time series of fluorescence images (e.g., video) by depressing a remote switch or foot-control, or via a keyboard (not shown) connected to the processor assembly 16. As a result, the illumination source 15 is turned on and the processor assembly 16 begins recording the fluorescence image data provided by the image acquisition assembly 13. In lieu of the pulsed mode discussed above, it will be understood that, in some embodiments, the illumination source 15 can comprise an emission source which is continuously on during the image acquisition sequence. When operating in the pulsed mode of the embodiment, the image sensor 264 in the camera module 250 (FIG. 16) is synchronized to collect fluorescence emission following the laser pulse produced by the diode laser 202 in the light source 200 (FIG. 15). In this way, maximum fluorescence emission intensity is recorded, and signal-to-noise ratio is optimized. In this embodiment, the fluorescence imaging agent 17 is administered to the subject and delivered to the area of interest via arterial flow. Acquisition of the time series of fluorescence images is initiated, for example, shortly after administration of the fluorescence imaging agent 17, and the time series of fluorescence images from substantially the entire area of interest are acquired throughout the ingress of the fluorescence imaging agent 17. The fluorescence emission from the region of interest is collected by the collection optics of the camera module 250. Residual ambient and reflected excitation light is attenuated by subsequent optical elements (e.g., optical element 256 in FIG. 16 which may be a filter) in the camera module 250 so that the fluorescence emission can be acquired by the image sensor assembly 264 with minimal interference by light from other sources.

In various embodiments, the processor is in communication with the imaging system or is a component of the imaging system. The program code or other computer-readable instructions, according to the various embodiments, can be written and/or stored in any appropriate programming language and delivered to the processor in various forms, including, for example, but not limited to information permanently stored on non-writeable storage media (e.g., read-only memory devices such as ROMs or CD-ROM disks), information alterably stored on writeable storage media (e.g., hard drives), information conveyed to the processor via transitory mediums (e.g., signals), information conveyed to the processor through communication media, such as a local area network, a public network such as the Internet, or any type of media suitable for storing electronic instruction. In various embodiments, the tangible non-transitory computer readable medium comprises all computer-readable media. In some embodiments, computer-readable instructions for performing one or more of the methods or techniques discussed herein may be stored solely on non-transitory computer readable media.

In some embodiments, the illumination and imaging system may be a component of a medical imaging system such as the fluorescence medical imaging system 10, which acquires medical image data. In embodiments where the illumination and imaging system is a component of the imaging system, such as the fluorescence imaging system described above, the light source, illumination module, imaging module and the processor of the medical imaging system may function as the camera assembly and the processor of the illumination and imaging system. A skilled person will appreciate that imaging systems other than fluorescence imaging systems may be employed for use with illumination and/or imaging systems such as those described herein, depending on the type of imaging being performed. Example Imaging Agents for Use in Generating Image Data According to some embodiments, in fluorescence medical imaging applications, the imaging agent is a fluorescence imaging agent such as, for example, indocyanine green (ICG) dye. ICG, when administered to the subject, binds with blood proteins and circulates with the blood in the tissue. The fluorescence imaging agent (e.g., ICG) may be administered to the subject as a bolus injection (e.g., into a vein or an artery) in a concentration suitable for imaging such that the bolus circulates in the vasculature and traverses the microvasculature. In other embodiments in which multiple fluorescence imaging agents are used, such agents may be administered simultaneously, e.g. in a single bolus, or sequentially in separate boluses. In some embodiments, the fluorescence imaging agent may be administered by a catheter. In certain embodiments, the fluorescence imaging agent may be administered less than an hour in advance of performing the measurement of signal intensity arising from the fluorescence imaging agent. For example, the fluorescence imaging agent may be administered to the subject less than 30 minutes in advance of the measurement. In yet other embodiments, the fluorescence imaging agent may be administered at least 30 seconds in advance of performing the measurement. In still other embodiments, the fluorescence imaging agent may be administered contemporaneously with performing the measurement.

According to some embodiments, the fluorescence imaging agent may be administered in various concentrations to achieve a desired circulating concentration in the blood. For example, in embodiments where the fluorescence imaging agent is ICG, it may be administered at a concentration of about 2.5 mg/mL to achieve a circulating concentration of about 5 μM to about 10 μM in blood. In various embodiments, the upper concentration limit for the administration of the fluorescence imaging agent is the concentration at which the fluorescence imaging agent becomes clinically toxic in circulating blood, and the lower concentration limit is the instrumental limit for acquiring the signal intensity data arising from the fluorescence imaging agent circulating with blood to detect the fluorescence imaging agent. In various other embodiments, the upper concentration limit for the administration of the fluorescence imaging agent is the concentration at which the fluorescence imaging agent becomes self-quenching. For example, the circulating concentration of ICG may range from about 2 μM to about 10 mM. Thus, in one aspect, the method comprises the step of administration of the imaging agent (e.g., a fluorescence imaging agent) to the subject and acquisition of the signal intensity data (e.g., video) prior to processing the signal intensity data according to the various embodiments. In another aspect, the method excludes any step of administering the imaging agent to the subject.

According to some embodiments, a suitable fluorescence imaging agent for use in fluorescence imaging applications to generate fluorescence image data is an imaging agent which can circulate with the blood (e.g., a fluorescence dye which can circulate with, for example, a component of the blood such as lipoproteins or serum plasma in the blood) and transit vasculature of the tissue (i.e., large vessels and microvasculature), and from which a signal intensity arises when the imaging agent is exposed to appropriate light energy (e.g., excitation light energy, or absorption light energy). In various embodiments, the fluorescence imaging agent comprises a fluorescence dye, an analogue thereof, a derivative thereof, or a combination of these. A fluorescence dye includes any non-toxic fluorescence dye. In certain embodiments, the fluorescence dye optimally emits fluorescence in the near-infrared spectrum. In certain embodiments, the fluorescence dye is or comprises a tricarbocyanine dye. In certain embodiments, the fluorescence dye is or comprises indocyanine green (ICG), methylene blue, or a combination thereof. In other embodiments, the fluorescence dye is or comprises fluorescein isothiocyanate, rhodamine, phycoerythrin, phycocyanin, allophycocyanin, o-phthaldehyde, fluorescamine, rose Bengal, trypan blue, fluoro-gold, or a combination thereof, excitable using excitation light wavelengths appropriate to each dye. In some embodiments, an analogue or a derivative of the fluorescence dye may be used. For example, a fluorescence dye analog or a derivative includes a fluorescence dye that has been chemically modified, but still retains its ability to fluoresce when exposed to light energy of an appropriate wavelength.

In various embodiments, the fluorescence imaging agent may be provided as a lyophilized powder, solid, or liquid. In certain embodiments, the fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. In various embodiments, any diluent or carrier which will maintain the fluorescence imaging agent in solution may be used. As an example, ICG may be reconstituted with water. In some embodiments, once the fluorescence imaging agent is reconstituted, it may be mixed with additional diluents and carriers. In some embodiments, the fluorescence imaging agent may be conjugated to another molecule, such as a protein, a peptide, an amino acid, a synthetic polymer, or a sugar, for example to enhance solubility, stability, imaging properties, or a combination thereof. Additional buffering agents may optionally be added including Tris, HCl, NaOH, phosphate buffer, and/or HEPES.

A person of skill in the art will appreciate that, although a fluorescence imaging agent was described above in detail, other imaging agents may be used in connection with the systems, methods, and techniques described herein, depending on the optical imaging modality.

In some embodiments, the fluorescence imaging agent used in combination with the methods and systems described herein may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva). In some embodiments, the fluorescence imaging agent may be administered in sufficient concentrations and in a suitable manner so as to effect lymphatic imaging.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

By way of summation and review, one or more embodiments may accommodate varied working distances while providing a flat illumination field and matching an illumination field to a target imaging field, thus allowing accurate quantitative imaging applications. An imaging element that focuses light from a target onto a sensor may be moved in synchrony with steering of the illumination field. Additionally or alternatively, a drape may be used that insures a close fit between a drape lens and a window frame of the device. Additionally or alternatively, one or more embodiments may allow ambient light to be subtracted from light to be imaged using a single sensor and controlled timing of illumination and exposure or detection. Additionally or alternatively, one or more embodiments may allow the display of a normalized fluorescence intensity measured within a target reticle region of an image frame.

In contrast, when illumination and imaging devices do not conform illumination to the target imaging field of view or provide a flat, i.e., even or substantially uniform, illumination field, illumination and image quality may suffer. An uneven illumination field can cause distracting and inaccurate imaging artifacts, especially for hand held imaging devices and when used at varied working distances, while excess light outside the imaging field of view reduces device efficiency and can distract the user when positioning the device.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments, however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. An imaging device for imaging target tissue of a subject comprising:

at least one imaging sensor; and a wavelength-dependent aperture upstream of the at least one imaging sensor, the wavelength-dependent aperture comprising:

a first aperture portion configured to permit transmission of visible light and fluorescence light, and a second aperture portion surrounding the first aperture portion and configured to permit transmission of the fluorescence light and block transmission of the visible light, wherein the second aperture portion is configured to block transmission of the visible light through absorption, wherein the first and second aperture portions are sized such that a depth of field for visible light at the at least one imaging sensor is substantially similar to a depth of field for fluorescence light at the at least one imaging sensor.

2. The imaging device of claim 1, wherein the fluorescence light is near infrared (NIR) light.

3. The imaging device of claim 1, further comprising a third aperture portion surrounding the first and second aperture portions, wherein the third aperture portion blocks transmission of both the visible and fluorescence light.

4. The imaging device of claim 1, wherein the second aperture portion comprises a film and the first aperture portion comprises an opening in the film.

5. The imaging device of claim 1, wherein the first aperture portion comprises a first film and the second aperture portion comprises a second film.

6. The imaging device of claim 5, wherein the first and second films are disposed on a single substrate.

7. The imaging device of claim 1, further comprising at least one lens located downstream of the wavelength dependent aperture.

8. The imaging device of claim 7, wherein the wavelength-dependent aperture is located in at least one pupil plane of the at least one lens.

9. The imaging device of claim 1, wherein the imaging device comprises a plurality of wavelength-dependent apertures.

10. The imaging device of claim 1, wherein the imaging device is an open-field imaging device configured for imaging the target tissue of the subject from outside of the subject.

11. The imaging device of claim 1, wherein the visible light comprises ambient light.

12. A method for imaging target tissue of a subject comprising:

receiving visible light and fluorescence light at a wavelength dependent aperture of an imaging device, at least a portion of the visible and fluorescence light being received from the target tissue of the subject;

transmitting the visible and fluorescence light through a first aperture portion of the wavelength dependent aperture;

transmitting the fluorescence light through a second aperture portion of the wavelength dependent aperture while blocking transmission of the visible light through the second aperture portion of the wavelength dependent aperture through absorption; and sensing by at least one image sensor the visible and fluorescence light transmitted through the wavelength dependent aperture, wherein the first and second aperture portions are sized such that a depth of field for visible light at the at least one imaging sensor is substantially similar to a depth of field for fluorescence light at the at least one imaging sensor.

13. The method of claim 12, wherein the fluorescence light is near infrared (NIR) light.

14. The method of claim 12, further comprising blocking transmission of both visible and fluorescence light through a third aperture portion of the wavelength dependent aperture.

15. The method of claim 12, wherein the second aperture portion comprises a film and the first aperture portion comprises an opening in the film.

16. The method of claim 12, wherein the first aperture portion comprises a first film and the second aperture portion comprises a second film.

17. The method of claim 16, wherein the first and second films are disposed on a single substrate.

18. The method of claim 12, wherein the imaging device comprises at least one lens located downstream of the wavelength dependent aperture.

19. The method of claim 18, wherein the wavelength-dependent aperture is located in at least one pupil plane of the at least one lens.

20. The method of claim 12, wherein the imaging device comprises a plurality of wavelength-dependent apertures.

21. The method of claim 12, wherein the visible light and fluorescence light are received by the imaging device outside of the subject.

22. The method of claim 12, wherein the visible light comprises ambient light.

* * * * *